US006692966B2

(12) United States Patent
Fallaux et al.

(10) Patent No.: US 6,692,966 B2
(45) Date of Patent: *Feb. 17, 2004

(54) PACKAGING SYSTEMS FOR HUMAN RECOMBINANT ADENOVIRUS TO BE USED IN GENE THERAPY

(75) Inventors: Frits J. Fallaux, Leiderdorp (NL); Robert C. Hoeben, Leiden (NL); Abraham Bout, Moerkapelle (NL); Domenico Valerio, Oegstgeest (NL); Alex J. van der Eb, Oegstgeest (NL)

(73) Assignee: Crucell Holland B.V., Leiden (NL)

( * ) Notice: Subject to any disclaimer, the term of this patent is extended or adjusted under 35 U.S.C. 154(b) by 0 days.

This patent is subject to a terminal disclaimer.

(21) Appl. No.: 09/912,552

(22) Filed: Jul. 23, 2001

(65) Prior Publication Data

US 2002/0187553 A1 Dec. 12, 2002

Related U.S. Application Data

(60) Division of application No. 09/356,575, filed on Jul. 19, 1999, now Pat. No. 6,265,212, which is a continuation-in-part of application No. 08/793,170, filed as application No. PCT/NL96/00244 on Jun. 14, 1996, now Pat. No. 5,994,128.

(30) Foreign Application Priority Data

Jun. 15, 1995 (EP) .......................................... 95201611
Jun. 26, 1995 (EP) .......................................... 95201728

(51) Int. Cl.⁷ ..................... C12N 15/861; C12N 15/64; A61K 48/00
(52) U.S. Cl. ..................... 435/456; 435/320.1; 435/325; 435/455; 424/93.2
(58) Field of Search ............................ 435/325, 320.1, 435/455, 456, 457, 91.4; 424/93.2

(56) References Cited

U.S. PATENT DOCUMENTS

| | | | | |
|---|---|---|---|---|
| 4,405,712 | A | 9/1983 | Vande Woude et al. | 435/5 |
| 4,497,796 | A | 2/1985 | Salser et al. | 514/44 |
| 4,727,028 | A | 2/1988 | Santerre et al. | 435/320.1 |
| 4,740,463 | A | 4/1988 | Weinberg et al. | 435/456 |
| 5,190,931 | A | 3/1993 | Inouye | 435/91.32 |
| 5,208,149 | A | 5/1993 | Inouye | 435/471 |
| 5,378,618 | A | 1/1995 | Sternberg et al. | 435/472 |
| 5,518,913 | A | 5/1996 | Massie et al. | 435/235.1 |
| 5,545,522 | A | 8/1996 | Van Gelder et al. | 435/6 |
| 5,585,362 | A | * 12/1996 | Wilson et al. | 514/44 |
| 5,652,224 | A | 7/1997 | Wilson et al. | 514/44 |
| 5,670,488 | A | 9/1997 | Gregory et al. | 514/44 |
| 5,707,618 | A | 1/1998 | Armentano et al. | 424/93.21 |
| 5,753,500 | A | 5/1998 | Shenk et al. | 435/320.1 |
| 5,837,511 | A | 11/1998 | Falck-Pedersen et al. | 435/456 |
| 5,994,106 | A | * 11/1999 | Kovesdi et al. | 435/91.4 |
| 5,994,128 | A | * 11/1999 | Fallaux et al. | 435/325 |
| 6,033,908 | A | * 3/2000 | Bout et al. | 435/325 |
| 6,040,174 | A | * 3/2000 | Imler et al. | 435/325 |
| 6,265,212 | B1 | * 7/2001 | Fallaux et al. | 435/320.1 |
| 6,306,652 | B1 | * 10/2001 | Fallaux et al. | 435/325 |
| 6,395,519 | B1 | * 5/2002 | Fallaux et al. | 435/91.42 |

FOREIGN PATENT DOCUMENTS

| | | |
|---|---|---|
| AU | A-28533/95 | 3/1996 |
| CA | 2053187 | 4/1993 |
| CA | 2117668 | 9/1995 |
| EP | 95201611.1 | 6/1995 |
| EP | 95201728.3 | 6/1995 |
| WO | WO 94/23582 | 10/1994 |
| WO | WO 94/26914 | 11/1994 |
| WO | WO 94/28152 | 12/1994 |
| WO | WO 95/00655 | 1/1995 |
| WO | WO 95/02697 | 1/1995 |
| WO | WO 95/27071 | 10/1995 |
| WO | WO 96/16676 | 6/1996 |
| WO | WO 96/18418 | 6/1996 |
| WO | WO 96/33280 | 10/1996 |
| WO | WO 96/40955 | 12/1996 |
| WO | WO 97/00326 | 1/1997 |
| WO | WO 97/00947 | 1/1997 |
| WO | WO 97/04119 | 2/1997 |
| WO | WO 97/05255 | 2/1997 |

OTHER PUBLICATIONS

Amalfitano et al., "Improved adenovirus packaging cell lines to support the growth of replication–defective gene–delivery vectors", *Proc. Natl. Acad. Sci. USA*, 93:3352–3356, Apr. 1996.

Amalfitano et al., "Isolation and characterization of packaging cell lines that coexpress the adenovirus E1, DNA polymerase, and preterminal proteins: implications for gene therapy", *Gene Therapy*, 4:258–263, 1997.

Armentano et al., "Characterization of an Adenovirus Gene Transfer Vector Containing an E4 Deletion", *Human Gene Therapy*, 6:1343–1353, Oct. 1995.

Brough et al., "A Gene Transfer Vector–Cell Line System for Complete Functional Complementation of Adenovirus Early Regions E1 and E4", *Journal of Virology*, 70(9):6497–6501, Sep. 1996.

(List continued on next page.)

*Primary Examiner*—Scott D. Priebe
(74) *Attorney, Agent, or Firm*—TraskBritt

(57) ABSTRACT

The problem of replication-competent adenovirus in virus production is solved in that we have developed packaging cells that have no overlapping sequences with a new basic vector and thus, are suited for safe large scale production of recombinant adenoviruses. One of the additional problems associated with the use of recombinant adenovirus vectors is the host-defense reaction against treatment with adenovirus. Another aspect of the invention involves screening recombinant adenovirus vector lots, especially those intended for clinical use, for the presence of adenovirus E1 sequences, as this will reveal replication-competent adenovirus, as well as revertant E1 adenoviruses. It is also an aspect of the present invention to molecularly characterize the revertants that are generated in the newer helper/vector combinations.

12 Claims, 20 Drawing Sheets

OTHER PUBLICATIONS

Brough et al., "Construction, Characterization, and Utilization of Cell Lines Which Inducibly Express the Adenovirus DNA–Binding Protein", *Virology*, 190:624–634, 1992.

Brough et al., Stable Cell Lines for Complementation of Adenovirus Early Regions E1, E2A and E4; *Abstract Book CSH Conference On Gene Therapy*, 42, 1996.

Caravokyri et al., "Constitutive Episomal Expression of Polypeptide IX (plX) in a 293–Based Cell Line Complements the Deficiency of plX Mutant Adenovirus Type 5", *Journal of Virology*, 69(11):6627–6633, Nov. 1995.

Fallaux et al., "Characterization of 911: A New Helper Cell Line for the Titration and Propagation of Early Region 1–Deleted Adenoviral Vectors", *Human Gene Therapy*, 7:215–222, 1996.

Fisher et al., "Recombinant Adenovirus Deleted of All Viral Genes for Gene Therapy of Cystic Fibrosis", *Virology*, 217:11–22, 1996.

Gao et al., "Biology of Adenovirus Vectors with E1 and E4 Deletions for Liver–Directed Gene Therapy", *Journal of Virology*, 70(12):8943–8943, Dec. 1996.

Gorziglia et al., "Elimination of both E1 and E2a from Adenovirus Vectors Further Improves Prospects for in Vivo Human Gene Therapy", *Journal of Virology*, 70(6):4173–4178, Jun. 1996.

Hardy et al., "Construction of Adenovirus Vectors through Cre–lox Recombination", *Journal of Virology*, 71(3):1842–1849, Mar. 1997.

Hehir et al., "Molecular Characterization of Replication–Competent Variants of Adenovirus Vectors and Genome Modifications To Prevent Their Occurence", *Journal of Virology*, 70(12):8459–8467, Dec. 1996.

Imler et al., "Novel complementation cell lines derived from human lung carcinoma A549 cells support the growth of E1–deleted adenovirus vectors", *Gene Therapy*, 3:75–84, 1996.

Kornberg, Arthur, "DNA Replication", W.H. Freeman and Company, San Francisco, 8 pages.

Krougliak et al., "Development of Cell Lines Capable of Complementing E1, E4, and Protein IX Defective Adenovirus Type 5 Mutants", *Human Gene Therapy*, 6:1575–1586, Dec. 1995.

Lieber et al., "Recombinant Adenoviruses with Large Deletions Generated by Cre–Mediated Excision Exhibit Different Biological Properties Compared with First–Generation Vectors In Vitro and In Vivo", *Journal of Virology*, 70:8944–8960, Dec. 1996.

Ngo et al., "in The Protein Folding Problem and Tertiary Structure Prediction", Merz et al., (ed.), Birkhauser, Boston, MA, pp. 433 and 492–495, 1994.

Sabatie et al., "Process Development for the Production of Second Generation Adenovirus Vectors for Gene Transfer in Clinical Protocols", *Abstract Book 14th Meeting on Animal Cell Technology*, Bl–3, 1996.

Schaack et al., "Adenovirus Type 5 Precursor Terminal Protein–Expressing 293 and HeLa Cell Lines", *Journal of Virology*, 69(7):4079–4085, Jul. 1995.

Vanhaesebroeck et al., *Virology*, 176(2), pp. 362–368, Jun. 1990.

Wang et al., "A packaging cell line for propagation of recombinant adenovirus vectors containing two lethal gene–region deletions", *Gene Therapy*, 2:775–783, 1995.

Yeh et al., "Efficient Dual Transcomplementation of Adenovirus E1 and E4 Regions from a 293–Derived Cell Line Expressing a Minimal E4 Functional Unit", *Journal of Virology*, 70(1):559–565, Jan. 1996.

Zhou et al., "Development of a Complementing Cell Line and a System for Construction of Adenovirus Vectors with E1 and E2a Deleted", *Journal of Virology*, 70(1):7030–7038, Oct. 1996.

\* cited by examiner

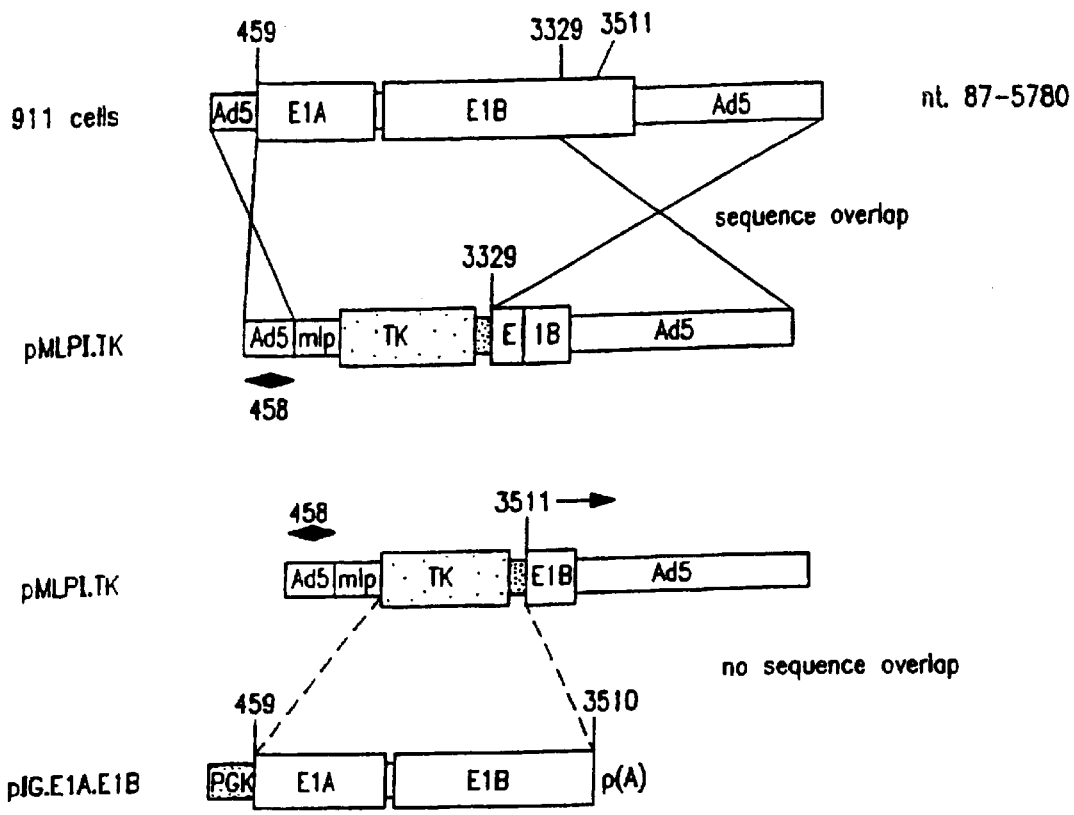
FIG. IIA
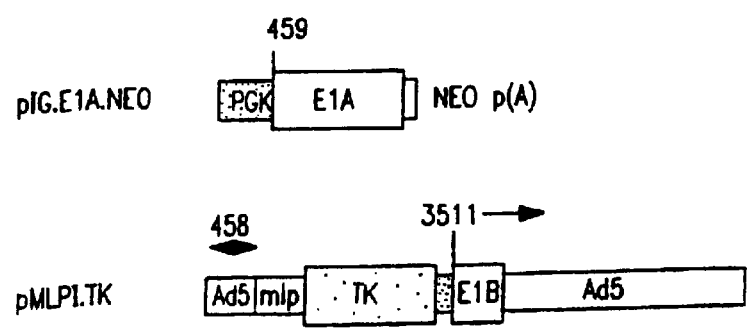
FIG. IIB

```
5'-GTACACTGACCTAGTGCCGCCCGGGCA
    |||||||||||||||||| A
      GATCACGGCGGGCCCGA
```

SEQ ID NO:22

FIG.15

SEQUENCE LISTING

```
<160> NUMBER OF SEQ ID NOS: 22

<210> SEQ ID NO 1
<211> LENGTH: 21
<212> TYPE: DNA
<213> ORGANISM: Unknown
<220> FEATURE:
<223> OTHER INFORMATION: Derived from Adenovirus

<400> SEQUENCE: 1
cgtgtagtgt atttataccc g                                              21

<210> SEQ ID NO 2
<211> LENGTH: 21
<212> TYPE: DNA
<213> ORGANISM: Unknown
<220> FEATURE:
<223> OTHER INFORMATION: Derived from Adenovirus

<400> SEQUENCE: 2
tcgtcactgg gtggaaagcc a                                              21

<210> SEQ ID NO 3
<211> LENGTH: 21
<212> TYPE: DNA
<213> ORGANISM: Unknown
<220> FEATURE:
<223> OTHER INFORMATION: Derived from Adenovirus

<400> SEQUENCE: 3
tacccgccgt cctaaaatgg c                                              21

<210> SEQ ID NO 4
<211> LENGTH: 20
<212> TYPE: DNA
<213> ORGANISM: Unknown
<220> FEATURE:
<223> OTHER INFORMATION: Derived from Adenovirus

<400> SEQUENCE: 4
tggacttgag ctgtaaacgc                                                20

<210> SEQ ID NO 5
<211> LENGTH: 21
<212> TYPE: DNA
```

-continued

```
<213> ORGANISM: Unknown
<220> FEATURE:
<223> OTHER INFORMATION: Derived from Adenovirus

<400> SEQUENCE: 5
gcctccatgg aggtcagatg t                                               21

<210> SEQ ID NO 6
<211> LENGTH: 20
<212> TYPE: DNA
<213> ORGANISM: Unknown
<220> FEATURE:
<223> OTHER INFORMATION: Derived from Adenovirus

<400> SEQUENCE: 6
gcttgagccc gagacatgtc                                                 20

<210> SEQ ID NO 7
<211> LENGTH: 24
<212> TYPE: DNA
<213> ORGANISM: Unknown
<220> FEATURE:
<223> OTHER INFORMATION: Derived from Adenovirus

<400> SEQUENCE: 7
cccctcgagc tcaatctgta tctt                                            24

<210> SEQ ID NO 8
<211> LENGTH: 27
<212> TYPE: DNA
<213> ORGANISM: Unknown
<220> FEATURE:
<223> OTHER INFORMATION: Derived from Adenovirus

<400> SEQUENCE: 8
gggggatccg aacttgttta ttgcagc                                         27

<210> SEQ ID NO 9
<211> LENGTH: 25
<212> TYPE: DNA
<213> ORGANISM: Unknown
<220> FEATURE:
<223> OTHER INFORMATION: Derived from Adenovirus

<400> SEQUENCE: 9
gggagatcta gacatgataa gatac                                           25

<210> SEQ ID NO 10
<211> LENGTH: 27
<212> TYPE: DNA
<213> ORGANISM: Unknown
<220> FEATURE:
<223> OTHER INFORMATION: Derived from Adenovirus

<400> SEQUENCE: 10
gggagatctg tactgaaatg tgtgggc                                         27

<210> SEQ ID NO 11
<211> LENGTH: 24
<212> TYPE: DNA
<213> ORGANISM: Unknown
<220> FEATURE:
<223> OTHER INFORMATION: Derived from Adenovirus

<400> SEQUENCE: 11
ggaggctgca gtctccaacg gcgt                                            24
```

<210> SEQ ID NO 12
<211> LENGTH: 27
<212> TYPE: DNA
<213> ORGANISM: Unknown
<220> FEATURE:
<223> OTHER INFORMATION: Derived from Adenovirus

<400> SEQUENCE: 12 ggggatcct caaatcgtca cttccgt                                27

<210> SEQ ID NO 13
<211> LENGTH: 27
<212> TYPE: DNA
<213> ORGANISM: Unknown
<220> FEATURE:
<223> OTHER INFORMATION: Derived from Adenovirus

<400> SEQUENCE: 13
ggggtctaga catcatcaat aatatac                               27

<210> SEQ ID NO 14
<211> LENGTH: 32
<212> TYPE: DNA
<213> ORGANISM: Unknown
<220> FEATURE:
<223> OTHER INFORMATION: Derived from Adenovirus

<400> SEQUENCE: 14
ggcgaattcg tcgacatcat caataatata cc                         32

<210> SEQ ID NO 15
<211> LENGTH: 32
<212> TYPE: DNA
<213> ORGANISM: Unknown
<220> FEATURE:
<223> OTHER INFORMATION: Derived from Adenovirus

<400> SEQUENCE: 15
ggcgaattcg gtaccatcat caataatata cc                         32

<210> SEQ ID NO 16
<211> LENGTH: 17
<212> TYPE: DNA
<213> ORGANISM: Unknown
<220> FEATURE:
<223> OTHER INFORMATION: Derived from Adenovirus

<400> SEQUENCE: 16
ctgtgtacac cggcgca                                          17

<210> SEQ ID NO 17
<211> LENGTH: 50
<212> TYPE: DNA
<213> ORGANISM: Unknown
<220> FEATURE:
<223> OTHER INFORMATION: Derived from Adenovirus

<400> SEQUENCE: 17
gtacactgac ctagtgccgc ccgggcaaag cccgggcggc actaggtcag      50

<210> SEQ ID NO 18
<211> LENGTH: 50
<212> TYPE: DNA
<213> ORGANISM: Unknown
<220> FEATURE:

-continued

```
<223> OTHER INFORMATION: Derived from Adenovirus

<400> SEQUENCE: 18
gtacctgacc tagtgccgcc cgggctttgc ccgggcggca ctaggtcagt              50

<210> SEQ ID NO 19
<211> LENGTH: 55
<212> TYPE: DNA
<213> ORGANISM: Unknown
<220> FEATURE:
<223> OTHER INFORMATION: Derived from Adenovirus

<400> SEQUENCE: 19
gtacattgac ctagtgccgc ccgggcaaag cccgggcggc actaggtcaa tcgat        55

<210> SEQ ID NO 20
<211> LENGTH: 55
<212> TYPE: DNA
<213> ORGANISM: Unknown
<220> FEATURE:
<223> OTHER INFORMATION: Derived from Adenovirus

<400> SEQUENCE: 20
gtacatcgat tgacctagtg ccgcccgggc tttgcccggg cggcactagg tcaat        55

<210> SEQ ID NO 21
<211> LENGTH: 5620
<212> TYPE: DNA
<213> ORGANISM: Unknown
<220> FEATURE:
<223> OTHER INFORMATION: Derived from Adenovirus

<400> SEQUENCE: 21
catcatcaat aatatacctt attttggatt gaagccaata tgataatgag ggggtggagt    60
ttgtgacgtg gcgcggggcg tgggaacggg gcgggtgacg tagtagtgtg gcggaagtgt   120
gatgttgcaa gtgtggcgga acacatgtaa gcgacggatg tggcaaaagt gacgttttg    180 gtgtgcgccg tgtacacag gaagtgacaa ttttcgcgcg gttttaggcg gatgttgtag    240
taaatttggg cgtaaccgag taagatttgg ccattttcgc gggaaaactg aataagagga   300
agtgaaatct gaataatttt tgttactca tagcgcgtaa tatttgtcta gggccgcggg    360
gactttgacc gtttacgtgg agactcgccc aggtgttttt ctcaggtgtt ttccgcgttc   420
cgggtcaaag ttggcgtttt attattatag tcaggggctg caggtcgtta cataacttac   480
ggtaaatggc ccgcctggct gaccgcccaa cgaccccgc ccattgacgt caataatgac    540
gtatgttccc atagtaacgc caatagggac tttccattga cgtcaatggg tggagtattt   600
acggtaaact gcccacttgg cagtacatca agtgtatcat atgccaagta cgccccctat   660
tgacgtcaat gacggtaaat ggcccgcctg gcattatgcc cagtacatga ccttatggga   720
ctttcctact tggcagtaca tctacgtatt agtcatcgct attaccatgg tgatgcggtt   780
ttggcagtac atcaatgggc gtggatagcg gtttgactca cggggatttc caagtctcca   840
ccccattgac gtcaatggga gtttgtttg gcaccaaaat caacgggact ttccaaaatg   900
tcgtaacaac tccgccccat tgacgcaaat gggcggtagg cgtgtacggt gggaggtcta   960
tataagcaga gctcgtttag tgaaccgtca gatcgcctgg agacgccatc cacgctgttt  1020
tgacctccat agaagacacc gggaccgatc agcctccgg actctagagg atccggtact  1080
cgaggaactg aaaaaccaga aagttaactg gtaagtttag tctttttgtc ttttatttca  1140
ggtcccggat ccggtggtgg tgcaaatcaa agaactgctc ctcagtggat gttgccttta  1200
```

-continued

```
cttctagtat caagcttgaa ttcctttgtg ttacattctt gaatgtcgct cgcagtgaca    1260
ttagcattcc ggtactgttg gtaaaatgga agacgccaaa aacataaaga aaggcccggc    1320
gccattctat cctctagagg atggaaccgc tggagagcaa ctgcataagg ctatgaagaa    1380
atacgccctg gttcctggaa caattgcttt tacagatgca catatcgagg tgaacatcac    1440
gtacgcggaa tacttcgaaa tgtccgttcg gttggcagaa gctatgaaac gatatgggct    1500
gaatacaaat cacagaatcg tcgtatgcag tgaaaactct cttcaattct ttatgccggt    1560
gttgggcgcg ttatttatcg gagttgcagt tgcgcccgcg aacgacattt ataatgaacg    1620
tgaattgctc aacagtatga acatttcgca gcctaccgta gtgtttgttt ccaaaaaggg    1680
gttgcaaaaa attttgaacg tgcaaaaaaa attaccaata atccagaaaa ttattatcat    1740
ggattctaaa acggattacc agggatttca gtcgatgtac acgttcgtca catctcatct    1800
acctcccggt tttaatgaat acgattttgt accagagtcc tttgatcgtg acaaaacaat    1860
tgcactgata atgaattcct ctggatctac tgggttacct aagggtgtgg cccttccgca    1920
tagaactgcc tgcgtcagat tctcgcatgc cagagatcct attttttggca atcaaatcat    1980 tccggatact gcgattttaa gtgttgttcc attccatcac ggttttggaa tgtttactac    2040
actcggatat ttgatatgtg gatttcgagt cgtcttaatg tatagatttg aagaagagct    2100 gttttttacga tcccttcagg attacaaaat tcaaagtgcg ttgctagtac aaccctatt    2160 ttcattcttc gccaaaagca ctctgattga caaatacgat ttatctaatt tacacgaaat    2220
tgcttctggg ggcgcacctc tttcgaaaga agtcgggaa gcggttgcaa aacgcttcca    2280
tcttccaggg atacgacaag gatatgggct cactgagact acatcagcta ttctgattac    2340
acccgagggg gatgataaac cgggcgcggt cggtaaagtt gttccatttt ttgaagcgaa    2400
ggttgtggat ctggataccg ggaaaacgct gggcgttaat cagagaggcg aattatgtgt    2460
cagaggacct atgattatgt ccggttatgt aaacaatccg gaagcgacca acgccttgat    2520
tgacaaggat ggatggctac attctggaga catagcttac tgggacgaag acgaacactt    2580
cttcatagtt gaccgcttga agtctttaat taaatacaaa ggatatcagg tggcccccgc    2640
tgaattggaa tcgatattgt tacaacaccc caacatcttc gacgcgggcg tggcaggtct    2700
tcccgacgat gacgccggtg aacttcccgc cgccgttgtt gttttggagc acggaaagac    2760
gatgacggaa aaagagatcg tggattacgt cgccagtcaa gtaacaaccg cgaaaaagtt    2820
gcgcggagga gttgtgtttg tggacgaagt accgaaaggt cttaccggaa aactcgacgc    2880
aagaaaaatc agagagatcc tcataaaggc caagaagggc ggaaagtcca aattgtaaaa    2940
tgtaactgta ttcagcgatg acgaaattct tagctattgt aatgggggat ccccaacttg    3000
tttattgcag cttataatgg ttacaaataa agcaatagca tcacaaattt cacaaataaa    3060
gcattttttt cactgcattc tagttgtggt ttgtccaaac tcatcaatgt atcttatcat    3120
gtctggatcg gatcgatccc cgggtaccga gctcgaattc gtaatcatgg tcatagctgt    3180
ttcctgtgtg aaattgttat ccgctcacaa ttccacacaa catacgagcc ggaagcataa    3240
agtgtaaagc ctggggtgcc taatgagtga gctaactcac attaattgcg ttgcgctcac    3300
tgcccgcttt ccagtcggga aacctgtcgt gccagctgca ttaatgaatc ggccaacgcg    3360
cggggagagg cggtttgcgt attgggcgct cttccgcttc ctcgctcact gactcgctgc    3420
gctcggtcgt tcggctgcgg cgagcggtat cagctcactc aaaggcggta atacggttat    3480
ccacagaatc aggggataac gcaggaaaga acatgtgagc aaaaggccag caaaaggcca    3540
```

```
ggaaccgtaa aaaggccgcg ttgctggcgt ttttccatag gctccgcccc cctgacgagc    3600
atcacaaaaa tcgacgctca agtcagaggt ggcgaaaccc gacaggacta taaagatacc    3660
aggcgtttcc ccctggaagc tccctcgtgc gctctcctgt tccgaccctg ccgcttaccg    3720
gatacctgtc cgcctttctc ccttcgggaa gcgtggcgct ttctcatagc tcacgctgta    3780
ggtatctcag ttcggtgtag gtcgttcgct ccaagctggg ctgtgtgcac gaaccccccg    3840
ttcagcccga ccgctgcgcc ttatccggta actatcgtct tgagtccaac ccggtaagac    3900
acgacttatc gccactggca gcagccactg gtaacaggat tagcagagcg aggtatgtag    3960
gcggtgctac agagttcttg aagtggtggc ctaactacgg ctacactaga aggacagtat    4020
ttggtatctg cgctctgctg aagccagtta ccttcggaaa aagagttggt agctcttgat    4080
ccggcaaaca aaccaccgct ggtagcggtg gttttttttgt ttgcaagcag cagattacgc    4140
gcagaaaaaa aggatctcaa gaagatcctt tgatcttttc tacggggtct gacgctcagt    4200
ggaacgaaaa ctcacgttaa gggattttgg tcatgagatt atcaaaaagg atcttcacct    4260 agatccttt aaattaaaaa tgaagtttta atcaatcta agtatatat gagtaaactt    4320 ggtctgacag ttaccaatgc ttaatcagtg aggcacctat ctcagcgatc tgtctatttc    4380
gttcatccat agttgcctga ctccccgtcg tgtagataac tacgatacgg gagggcttac    4440
catctggccc cagtgctgca atgataccgc gagacccacg ctcaccggct ccagatttat    4500
cagcaataaa ccagccagcc ggaagggccg agcgcagaag tggtcctgca actttatccg    4560
cctccatcca gtctattaat tgtttgccgg aagctagagt aagtagttcg ccagttaata    4620
gtttgcgcaa cgttgttgcc attgctacag gcatcgtggt gtcacgctcg tcgtttggta    4680
tggcttcatt cagctccggt tcccaacgat caaggcgagt tacatgatcc cccatgttgt    4740
gcaaaaaagc ggttagctcc ttcggtcctc cgatcgttgt cagaagtaag ttggccgcag    4800
tgttatcact catggttatg gcagcactgc ataattctct tactgtcatg ccatccgtaa    4860
gatgcttttc tgtgactggt gagtactcaa ccaagtcatt ctgagaatag tgtatgcggc    4920
gaccgagttg ctcttgcccg gcgtcaatac gggataatac cgcgccacat agcagaactt    4980
taaaagtgct catcattgga aaacgttctt cggggcgaaa actctcaagg atcttaccgc    5040
tgttgagatc cagttcgatg taacccactc gtgcacccaa ctgatcttca gcatctttta    5100
ctttcaccag cgtttctggg tgagcaaaaa caggaaggca aaatgccgca aaaaagggaa    5160
taagggcgac acggaaatgt tgaatactca tactcttcct ttttcaatat tattgaagca    5220
tttatcaggg ttattgtctc atgagcggat acatatttga atgtatttag aaaaataaac    5280
aaataggggt tccgcgcaca tttccccgaa aagtgccacc tgacgtctaa gaaaccatta    5340
ttatcatgac attaacctat aaaaataggc gtatcacgag gccctatgcgg tgtgaaatag    5400 cgcacagatg cgtaaggaga aaataccgca tcaggcgcca ttcgccattc aggctgcgca    5460
actgttggga agggcgatcg gtgcgggcct cttcgctatt acgccagctg gcgaaagggg    5520
gatgtgctgc aaggcgatta agttgggtaa cgccagggtt ttcccagtca cgacgttgta    5580
aaacgacggc cagtgccaag cttgcatgcc tgcaggtcga                          5620
```

<210> SEQ ID NO 22
<211> LENGTH: 45
<212> TYPE: DNA
<213> ORGANISM: Unknown
<220> FEATURE:
<223> OTHER INFORMATION: Derived from Adenovirus -continued

```
<400> SEQUENCE: 22
gtacactgac ctagtgccgc ccgggcaaag cccccgcggc actag                    45
```

PACKAGING SYSTEMS FOR HUMAN RECOMBINANT ADENOVIRUS TO BE USED IN GENE THERAPY

CROSS-REFERENCE TO RELATED APPLICATIONS

This application is a divisional of co-owned U.S. patent application Ser. No. 09/356,575, filed on Jul. 19, 1999, U.S. Pat. No. 6,265,212, the contents of which are incorporated by this reference, which is a continuation-in-part of U.S. application Ser. No. 08/793,170 filed Mar. 25, 1997, now U.S. Pat. No. 5,994,128, issued Nov. 30, 1999, incorporated herein by reference, which is the national stage filing of PCT/NL96/00244 filed Jun. 14, 1996.

TECHNICAL FIELD

The present invention relates to the field of recombinant DNA technology, more in particular to the field of gene therapy. Specifically, the present invention relates to gene therapy using materials derived from adenovirus, in particular human recombinant adenovirus, and relates to novel virus-derived vectors and novel packaging cell lines for vectors based on adenoviruses. Furthermore, this invention also pertains to the screening of replication-competent and revertant E1 adenoviruses from recombinant adenoviruses used in gene therapy.

BACKGROUND

Gene therapy is a recently developed concept for which a wide range of applications can be and have been envisaged. In gene therapy, a molecule carrying specific genetic information is introduced into some or all cells of a host. This results in the specific genetic information being padded to the host in a functional format. The specific genetic information added may be a gene or a derivative of a gene, such as a cDNA (which encodes a protein), or the like. In the case where cDNA is added, the encoded protein can be expressed by the machinery of the host cell.

The genetic information can also be a sequence of nucleotides complementary to a sequence of nucleotides (be it DNA or RNA) present in the host cell. With this functional format, the added DNA molecule or copies made thereof in situ are capable of base pairing with the complementary sequence present in the host cell.

Applications of such gene therapy techniques include, but are not limited to, the treatment of genetic disorders by supplementing a protein or other substance which is, through the genetic disorder, not present or at least present in insufficient amounts in the host, the treatment of tumors or other such non-acquired diseases, and the treatment of acquired diseases such as immune diseases, autoimmune diseases, infections, and the like.

As may be clear from the above, there are basically three different approaches in gene therapy. The first approach is directed toward compensating for a deficiency present in a host (such as a mammalian host). The second approach is directed toward the removal or elimination of unwanted substances (organisms or cells). The third approach is directed toward the application of a recombinant vaccine (e.g., directed against tumors or foreign micro-organisms).

Adenoviruses carrying deletions have been proposed as suitable vehicles for the purpose of gene therapy. Adenoviruses are essentially non-enveloped DNA viruses. Gene-transfer vectors derived from such adenoviruses (known as "adenoviral vectors") have several features that make them particularly useful for gene transfer. These features include, but are not limited to: 1) the fact that the biology of the adenoviruses is characterized in detail, 2) that the adenovirus is not associated with severe human pathology, 3) that the adenovirus is extremely efficient in introducing its DNA into the host cell, 4) that the adenovirus can infect a wide variety of cells and has a broad host-range, 5) that the adenovirus can be produced in large quantities with relative ease, and 6) that the adenovirus can be rendered replication defective by deletions in the early-region 1 ("E1") of the viral genome, thus providing an important safety feature.

The adenovirus genome is a linear double-stranded DNA molecule of approximately 36000 base pairs with the 55 kiloDalton ("kD") terminal protein covalently bound to the 5' terminus of each strand. The adenovirus DNA contains identical Inverted Terminal Repeats (ITR) of about 100 base pairs with the exact length depending on the serotype. The viral origins of replication are located within the ITRs at the genome ends. The synthesis of the DNA occurs in two stages. First, the replication proceeds by strand displacement, generating a daughter duplex molecule and a parental displaced strand. The displaced strand is single stranded and can form a structure known as a "panhandle" intermediate, which allows replication initiation and generation of a daughter duplex molecule. Alternatively, replication may proceed from both ends of the genome simultaneously, obviating the need to form the panhandle intermediate structure. The replication is summarized in FIG. 14 (adapted from Lechner, R. L. and Kelly Jr., T. J., "The Structure of Replicating Adenovirus 2 DNA Molecules. *J. Mol. Biol.* 174, pp. 493–510 (1977), hereby incorporated herein by reference).

During the productive infection cycle, the viral genes are expressed in two phases: an early phase and a late phase. The early phase is the period up to viral DNA replication, and the late phase is the period which coincides with the initiation of viral DNA replication. During the early phase, only the early gene products encoded by regions E1, E2, E3 and E4 are expressed, which carry out a number of functions that prepare the cell for synthesis of viral structural proteins (see Berk, A. J., *Ann. Rev. Genet.* 20, pp. 45–79 (1986), hereby incorporated herein by reference). During the late phase, the late viral gene products are expressed in addition to the early gene products and host cell DNA and protein synthesis are shut off. Consequently, the cell becomes dedicated to the production of viral DNA and of viral structural proteins (see Tooze, J., *DNA Tumor Viruses* (revised), Cold Spring Harbor Laboratory, Cold Spring Harbor, N.Y. (1981), hereby incorporated herein by reference).

The E1 region of adenovirus is the first region of adenovirus expressed after infection of the target cell. This region consists of two transcriptional units, the E1A and E1B genes. Both the E1A and E1B are required for oncogenic transformation of primary (embryonal) rodent cultures. The main functions of the E1A gene products are:

i) to induce quiescent cells to enter the cell cycle and resume cellular DNA synthesis, and ii) to transcriptionally activate the E1B gene and the other early regions (E2, E3, E4).

Transfection of primary cells with the E1A gene alone can induce unlimited proliferation (known as "immortalization"), but does not result in complete transformation. However, the expression of E1A in most cases results in the induction of programmed cell death (apoptosis), and only occasionally immortalization is obtained (see Jochemsen, et al., *EMBO J.* 6, pp. 3399–3405

(1987), hereby incorporated herein by reference). Co-expression of the E1B gene is required to prevent induction of apoptosis and for complete morphological transformation to occur. In established immortal cell lines, high level expression of E1A can cause complete transformation in the absence of E1B (see Roberts et al., *J. Virol.* 56, pp. 404–413 (1985), hereby incorporated herein by reference).

The E1B-encoded proteins assist E1A in redirecting the cellular functions to allow viral replication. The E1B 55 kD and E4 33 kD proteins, which form a complex that is essentially localized in the nucleus, function to inhibit the synthesis of host proteins and to facilitate the expression of viral genes. Their main influence is to establish selective transport of viral mRNAs from the nucleus to the cytoplasm, concomitantly with the onset of the late phase of infection. The E1B 21 kD protein is important for correct temporal control of the productive infection cycle, thereby preventing premature death of the host cell before the virus life cycle has been completed. Mutant viruses incapable of expressing the E1B 21 kD gene-product exhibit a shortened infection cycle that is accompanied by excessive degradation of host cell chromosomal DNA (deg-phenotype) and in an enhanced cytopathic effect (cyt-phenotype) (see Telling et al., "Absence of an Essential Regulatory Influence of the Adenovirus E1B 19-kiloDalton Protein on Viral Growth and Early Gene Expression in Human Diploid W138, HeLa, and A549 cells," *J. Virol.* 68, pp. 541–547 (1994), hereby incorporated herein by reference). The deg and cyt phenotypes are suppressed when the E1A gene is mutated, thus indicating that these phenotypes are a function of E1A (see White et al., *J. Virol.* 62, pp. 3445–3454 (1988), hereby incorporated herein by reference). Furthermore, the E1B 21 kD protein slows down the rate by which E1A switches on the other viral genes. It is not presently known through which mechanisms E1B 21 kD quenches these E1A dependent functions.

The vectors derived from human adenoviruses, in which at least the E1 region has been deleted and replaced by a gene of interest, have been used extensively for gene therapy experiments in the pre-clinical and clinical phase. As stated before, all adenovirus vectors currently used in gene therapy have a deletion in the E1 region, where novel genetic information can be introduced. The E1 deletion renders the recombinant virus replication defective (see Stratford-Perricaudet, L. D. and Perricaudet, M., "Gene Transfer into Animals: The Promise of Adenovirus", *Human Gene Transfer*, Cohen-Adenauer, and M. Boiron (Eds.), John Libbey Eurotext, pp. 51–61 (1991), hereby incorporated herein by reference). It has been demonstrated that recombinant adenoviruses are able to efficiently transfer recombinant genes to a rat liver and to airway epithelium of rhesus monkeys (see Bout et al., "In vivo Adenovirus-Mediated Transfer of Human CFTR cDNA to Rhesus Monkey Airway Epithelium: Efficacy, Toxicity and Safety", *Gene Therapy* 1, pp. 385–394 (1994) and Bout et al., "Lung Gene Therapy: In Vivo Adenovirus Mediated Gene Transfer to Rhesus Monkey Airway Epithelium", *Human Gene Therapy* 5, pp. 3–10 (1994), both hereby incorporated herein by reference). Additionally, researchers have observed a very efficient in vivo adenovirus mediated gene transfer to a variety of tumor cells in vitro and to solid tumors in animal models (lung tumors, glioma) and to human xenografts in immunodeficient mice (lung) in vivo (see Vincent et al., "Treatment of Lepto-Meningeal Metastasis in a Rat Model Using a Recombinant Adenovirus Containing the HSV-tk Gene", *J. Neurosurgery* in press (1996), Vincent, et al., "Herpes Simplex Virus Thymidine Kinase Gene Therapy for Rat Malignant Brain Tumors", *Human Gene Therapy* 7, pp. 197–205 (1996), and Blaese et al., "Vectors in Cancer Therapy: How Will They Deliver?", *Cancer Gene Therapy* 2, pp. 291–297 (1995), all of which are hereby incorporated herein by reference).

For example, in contrast to retroviruses, adenoviruses 1) do not integrate into the host cell genome, 2) are able to infect non-dividing cells, and 3) are able to efficiently transfer recombinant genes in vivo (see Brody, S. L., and Crystal, R. G., "Adenovirus-Mediated In Vivo Gene Transfer", *Ann. N. Y. Acad. Sci.* 716, pp. 90–101 (1994), hereby incorporated herein by reference). Those features make adenoviruses attractive candidates for in vivo gene transfer of, for instance, suicide or cytokine genes into tumor cells.

However, a problem associated with current recombinant adenovirus technology is the possibility of unwanted generation of replication-competent adenovirus ("RCA") during the production of recombinant adenovirus (see Lochmüller et al., "Emergence of Early Region 1-Containing Replication-Competent Adenovirus in Stocks of Replication-Defective Adenovirus Recombinants (DE1+ DE3) During Multiple Passages in 293 Cells", *Human Gene Therapy* 5, pp. 1485–1492 (1994) (hereinafter "the Lochmüller article") and Imler et al., "Novel Complementation Cell Lines Derived from Human Lung Carcinoma A549 Cells Support the Growth of E1-Deleted Adenovirus Vectors", *Gene Therapy* 3, pp. 75–84 (1996), both hereby incorporated herein by reference). This is caused by homologous recombination between overlapping sequences from the recombinant vector and the adenovirus constructs present in the complementing cell line, such as the 293 cells (see Graham et al., "Characteristics of a Human Cell Line Transformed by DNA from Adenovirus Type 5", *J. Gen. Virol.* 36, pp. 59–72 (1977) (hereinafter "the Graham article"), hereby incorporated herein by reference). RCA in batches to be used in clinical trials is undesirable because 1) RCA will replicate in an uncontrolled fashion, 2) RCA can complement replication-defective recombinant adenovirus, causing uncontrolled multiplication of the recombinant adenovirus, and 3) batches containing RCA induce significant tissue damage and hence strong pathological side effects (see the Lochmüller article). Therefore, batches to be used in clinical trials should be proven free of RCA (see Ostrove, J. M., "Safety Testing Programs for Gene Therapy Viral Vectors", *Cancer Gene Therapy* 1, pp. 125–131 (1994), hereby incorporated herein by reference).

As previously discussed, recombinant adenoviruses are deleted for the E1 region. The adenovirus E1 products trigger the transcription of the other early genes (E2, E3, E4), which consequently activate expression of the late virus genes. Therefore, it was generally thought that E1-deleted vectors would not express any other adenovirus genes. However, recently it has been demonstrated that some cell types are able to express adenovirus genes in the absence of E1 sequences. This indicates, that some cell types possess the machinery to drive transcription of adenovirus genes. In particular, it was demonstrated that such cells synthesize E2A and late adenovirus proteins.

In a gene therapy setting, this means that the transfer of the therapeutic recombinant gene to somatic cells not only results in expression of the therapeutic protein, but may also result in the synthesis of viral proteins. Cells that express adenoviral proteins are recognized and killed by Cytotoxic T Lymphocytes, which both eradicates the transduced cells and causes inflammations (see Bout et al., "In Vivo Adenovirus-Mediated Transfer of Human CFTR cDNA to Rhesus Monkey Airway Epithelium: Efficacy, Toxicity and Safety", *Gene Therapy* 1, pp. 385–394 (1994); Engelhardt, et al., "Adenovirus-Mediated Transfer of the CFTR Gene to Lung of Nonhuman Primates: Biological Efficacy Study", *Human Gene Therapy* 4, pp. 759–769 (1993); and Simon et al., "Adenovirus-Mediated Transfer of the CFTR Gene to Lung of Nonhuman Primates: Toxicity Study", *Human Gene Therapy* 4, pp. 771–780 (1993), all of which are hereby incorporated herein by reference). As this adverse reaction is hampering gene therapy, several solutions to this problem have been suggested. These solutions include using immunosuppressive agents after treatment, retainment of the adenovirus E3 region in the recombinant vector (see patent application EP 95202213, hereby incorporated herein by reference), and using temperature sensitive ("ts") mutants of human adenovirus, which have a point mutation in the E2A region (see WIPO patent application WO/28938, hereby incorporated herein by reference).

However, the strategies which circumvent the immune response have their limitations. For example, the use of ts mutant recombinant adenovirus diminishes the immune response to some extent, but was less effective in preventing pathological responses in the lungs (see Engelhardt et al., "Prolonged Transgene Expression in Cotton Rat Lung with Recombinant Adenoviruses Defective in E2A", *Human Gene Therapy* 5, pp. 1217–1229 (1994) (hereinafter "the Engelhardt 1994a article"), hereby incorporated herein by reference).

The E2A protein may induce an immune response by itself and it plays a pivotal role in the switch to the synthesis of late adenovirus proteins. Therefore, it is advantageous to make recombinant adenoviruses which are mutated in the E2 region, rendering it temperature sensitive, as has been claimed in WIPO patent application WO/28938. However, a major drawback of this system is the fact that, although the E2A protein is unstable at the non-permissive temperature, the immunogenic protein is still being synthesized. In addition, it is expected that the unstable protein activates late gene expression, albeit to a low extent. ts125 mutant recombinant adenoviruses have been tested, and prolonged recombinant gene expression has been reported (see Yang et al., "Inactivation of E2A in Recombinant Adenoviruses Improves the Prospect for Gene Therapy in Cystic Fibrosis", *Nat. Genet.* 7, pp. 362–369 (hereinafter "the Yang 1994a article"); the Engelhardt 1994a article; Engelhardt et al., "Ablation of E2A in Recombinant Adenoviruses Improves Transgene Persistence and Decreases Inflammatory Response in Mouse Liver", *Proc. Nat'l. Acad. Sci.* 91, pp. 6196–6200 (1994); Yang et al., "Cellular and Humoral Immune Responses to Viral Antigens Create Barriers to Lung-Directed Gene Therapy with Recombinant Adenoviruses", *J. Virol.* 69, pp. 2004–2015 (1995) (hereinafter "the Yang 1994b article"), all of which are hereby incorporated herein by reference). However, pathology in the lungs of cotton rats was still high (see the Engelhardt 1994a article), indicating that the use of ts mutants results in only a partial improvement in recombinant adenovirus technology. Others did not observe prolonged gene expression in mice and dogs using ts125 recombinant adenovirus (see Fang et al., "Lack of Persistence of E1-Recombinant Adenoviral Vectors Containing a Temperature Sensitive E2A Mutation in Immunocompetent Mice and Hemophilia Dogs", *Gene Therapy* 3, pp. 217–222 (1996), hereby incorporated herein by reference). An additional difficulty associated with the use of ts125 mutant adenoviruses is that a high frequency of reversion is observed. These revertants are either real revertants or the result of second site mutations (see Kruijer et al., "Structure and Function of DNA Binding Proteins from Revertants of Adenovirus Type 5 Mutants with a Temperature-Sensitive DNA Replication", *Virology* 124, pp. 425–433 (1983), and Nicolas et al., "Temperature-Independent Revertants of Adenovirus H5ts125 and H5ts107 Mutants in the DNA Binding Protein: Isolation of a New Class of Host Range Temperature Conditional Revertants", *Virology* 108, pp. 521–524 (1981), both of which are hereby incorporated herein by reference). Both types of revertants have an E2A protein that functions at normal temperature and have, therefore, similar toxicity as the wild-type virus.

E1-deleted recombinant adenovirus vectors ("rAV") can be propagated on dedicated helper cells. Dedicated helper cells are specialized cells that provide the E1 functions in trans, such as cell lines 293 and 911. Although encouraging results have been obtained with rAV, two major problems are associated with the use of rAVs. First, the host immune response against the adenovirus particles and the transduced cells and, second, the generation of replication-competent adenovirus ("RCA") during manufacture of rAV lots. RCA include revertant vectors that reacquired the E1 region as a result of homologous recombination with E1 sequences integrated in the helper cells. An aspect of the present invention which will be described below is a new helper cell line, PER.C6™, and non-overlapping E1-deleted adenoviral vectors which eliminates the problem of RCA generation by homologous recombination.

Cell line 293 has been the most frequently used cell line for the production of adenoviral vectors. This cell line was generated in the 1970s by transfection of diploid human embryonic kidney cells with sheared Adenoivrus serotype 5 ("Ad5") DNA in the course of a study on the transforming potential of the E1 genes of adenoviruses. Mapping of the Ad5 sequences in the genome of the 293 cells indicated the presence of contiguous Ad5 sequences from the left-hand end of the genome up to position 4137 (Evelegh et al., "Cloning and Sequencing of the Cellular-Viral Junctions from the Human Adenovirus Type 5 Transformed 293 Cell Line", *Virology* 233, pp. 423–429 (1997), hereby incorporated herein by reference). Thus, when typical E1 replacement vectors are propagated on the 293 cells, there is sequence homology between vector and helper cell DNA of up to about 450 base pairs at the left-hand side of the transgene, and about 800 base pairs at the right-hand side.

Due to this sequence overlap, the replication of rAV on the 293 cells results in the generation of RCA. This replication was first reported in the Lochmüller article wherein an E1+E3-deleted rAV was passaged multiple times on 293 cells. RCA was detected that contained E1, but lacked E3. This finding suggested that a small fraction of the rAVs had regained E1 by homologous recombination between overlapping sequences in the rAV DNA and the adenovirus DNA that is present in the 293 cells. This was later confirmed in the article by Hehir K. M. et al., "Molecular Characterization of Replication-Competent Variants of Adenovirus Vectors and Genome Modifications to Prevent Their Occurrence", *J. Virol.* 70, pp. 8459–8467 (1996) (hereinafter "the Hehir article"), hereby incorporated herein by reference, which discloses the propagation of Ad2-based rAV on the Ad5-transformed 293 cells and the detection of RCA carrying the Ad5 E1 region, despite the presence of the entire left-hand end of the Ad5 genome in the 293 cells. All of the studied RCA isolates were found to be generated by two homologous recombination events upstream and downstream of the transgene, resulting in loss of the transgene and re-acquirement by the vector of the E1 region.

The appearance of RCA in rAV batches is a chance event and is, therefore, unpredictable and difficult to control. This is a significant problem for good manufacturing practices, particularly if large scale batches have to be prepared. A number of reports on the frequency of RCA formation during manufacture of rAVs have been published (Table 1). These data illustrate that with the conventional E1-deleted Ad5 (and adenoviruses serotype 2 ("AD2")) rAVs, RCA is generated with frequencies that frustrate the large-scale production of clinical lots of rAVs.

TABLE 1

Frequency of RCA formation on 293 cells

| Log titer | RCA frequency | Assay sensitivity | Reference |
|---|---|---|---|
| <7.0 (n=5) | 0% | 1 RCA in 1 × 10$^9$ PFU* | REF. A |
| 7.0–7.9 (n=11) | 18% | " | " |
| 8.0–8.9 (n=58) | 24% | " | " |
| ≧9.0 (n=59) | 37% | " | " |
| ≧9.0 (n=14) | 36% | (not mentioned) | REF. B |
| ≧9.0 (n=21) | 56% | 1 RCA in 1 × 10$^9$ PFU | REF. C |
| ≧9.0 (n=20) | 55% | 1 RCA in 2.5 × 10$^9$ PFU | REF. D |

*PFU: plaque-forming units
a. Morgan et al., "Safety Considerations in the Development of New Retroviral and Adenoviral Vectors for Gene Therapy", New Developments and New Applications in Animal Cell Technology, Merten, O. W., Perrin, P., Griffiths, B. (Eds.), Kluwer Academic Publishers, pp 523–529 (1998), hereby incorporated herein by reference.
b. Imler et al., "Novel Complementation Cell Lines Derived from Human Lung Carcinoma A549 Cells Support the Growth of E1-Deleted Adenovirus Vectors", Gene Therapy 3, pp. 75–84 (1996), hereby incorporated herein by reference.
c. Hughes J. V., "Production Issues in a National Gene Vector Lab: Adenovirus and AAV Vector Development", Williamsburg Bioprocessing Conference, Williamsburg, Virginia, November 3–7, 1997, hereby incorporated herein by reference.
d. Fallaux et al., "New Helper Cells and Matched Early Region-1 Deleted Adenovirus Vectors Prevent Generation of Replication-Competent Adenoviruses, Human Gene Therapy 9, pp. 1909–1917 (1998) (hereinafter "the Fallaux 1998 article"), hereby incorporated herein by reference.

It should be noted that homologous recombination is not the only source of RCA. During the generation of rAV, RCAs can also be introduced into the system from outside. An exemplary method of rAV construction is to co-transfect the large ClaI-fragment of Ad5 together with an adapter plasmid that carries the gene of interest into the helper cells. Incomplete restriction-enzyme digestion of the adenovirus DNA can also be responsible for RCA production (i.e., wild-type Ad5, in this example).

The use of Ad genomes cloned in bacterial plasmids eliminates this risk. In addition, inadvertent cross-contamination can occur in laboratories where replication-competent adenoviruses are propagated.

Replication-competent adenoviruses derived from rAV that are currently known are very similar to wild-type adenoviruses, except that in most cases the E3 region is deleted, which has not been observed in wild-type isolates (see the Lochmüller article and the Hehir article). Most of the rAVs used to date are derived from human adenovirus serotype 2 or 5 (i.e., Ad2 and Ad5, respectively). Ad2 and Ad5 are mainly associated with mild respiratory infections, and these viruses have a tropism mainly for epithelial cells. RCA derived from such vectors can be expected to cause disease similar to that caused by wild-type Ad5 and Ad2.

The presence of RCA in rAV batches to be used in human patients is clearly undesirable, as the RCA may replicate in an uncontrolled manner in the patient. Although the replication of the RCA is limited by the recipient's immune system, it is a potential hazard, especially in immuno-comprised patients. In addition, RCA can rescue the vector, increasing the amount of vector shed by the patient. Rescue of the vector by RCA has been observed in cotton rats, a rodent species that is permissive for human adenovirus replication (see Imler et al., "Novel Complementation Cell Lines Derived from Human Lung Carcinoma A549 Cells Support the Growth of E1-Deleted Adenovirus Vectors", Gene Therapy 3, pp. 75–84 (1996) (hereinafter "the Imler reference"), hereby incorporated herein by reference). Furthermore, the presence of RCA is associated with inflammatory responses (see Hermens et al., "Adenoviral Vector-Mediated Gene Expression in the Nervous System of Immunocompetent Wistar and T Cell-Deficient Nude Rats: Preferential Survival of Transduced Astroglial Cells in Nude Rats", Human Gene Therapy 8, pp. 1049–1063 (1997), hereby incorporated herein by reference). Such inflammatory responses may be caused by the fact that multiplication of the adenovirus causes tissue damage, or by the fact that large amounts of adenovirus proteins are synthesized that are toxic for cells (e.g., hexon and penton), and are very immunogenic. Thus, the presence of RCA in rAV batches to be used in, for example, clinical trials is undesirable, as it may induce significant pathological side effects. This is also recognized by regulatory bodies, such as the Food and Drug Administration ("FDA"). Therefore, labor-intensive and expensive RCA screening tests such as the tissue culture method, the supernatant rescue assay, and PCR assay are required (see Dion et al., "Supernatant Rescue Assay Versus Polymerase Chain Reaction for Detection of Wild-Type Adenovirus-Contaminating Recombinant Adenovirus Stocks", J. Virol. Methods 56(1), pp. 99–107 (1996), hereby incorporated herein by reference). Although there are now options available that enable RCA-free production of rAV, screening for RCA is still required by the FDA. Screening for RCA has significantly increased the manufacturing costs of clinical rAV lots, and has led to delays in onsets of clinical studies.

Currently, intensive research efforts are focusing on the development of adenoviral vectors that have an altered tissue tropism. This is achieved by changing the genes encoding the capsid proteins, such as fiber, hexon, and penton. In these cases, the targets may be endothelium or smooth muscle cells, which are refractory to infection by wild-type Ad2 and Ad5. Thus, the presence of RCA in preparations of adenoviral vectors with altered tropism constitutes a potential safety risk. In this respect, it is noteworthy that adenoviruses with a tropism for endothelium have been shown to cause lethal infections in deer and mice (see Woods et al., "Systemic Adenovirus Infection Associated with High Mortality in Mule Deer (*Dolocoileus hemionus*) in California, Vet. Pathol. 33(2), pp. 125–132 (1996) (hereinafter "the Woods article") and Charles et al., "Mouse Adenovirus Type-1 Replication is Restricted to Vascular Endothelium in the CNS of Susceptible Strains of Mice", Virology 245(2), pp. 216–228 (1998) (hereinafter "the Charles article"), both of which are hereby incorporated herein by reference). The Woods article reported on very high mortality rates in deer upon infection with adenovirus. Mortality was caused by replication of the virus in endothelium of the animal, causing severe vasculitis. In mice, mouse adenovirus ("MAV") can cause lethal infections by targeting the vascular endothelium of the brain, as discussed in the Charles article. Also, in infants with an intact immune system, adenovirus infections can cause severe health problems and even death (see Munoz et al., "Disseminated Adenovirus Disease in Immunocompromised and Immunocompetent Children", Clin. Infect. Dis. 27(5), pp.

1194–1200 (1998), hereby incorporated herein by reference). Therefore, batches of rAV with an altered tropism, to be used in clinical trials, should be free of contaminating RCA.

To reduce the immunogenicity of the rAV, and to increase the insert capacity, several groups are developing strategies to produce rAVs that are deleted of all Ad genes (so-called "gutless" adenoviruses). Gutless rAVs can be propagated using a helper virus. In the most efficient system to date, an E1-deleted helper virus is used with a packaging signal that is flanked by bacteriophage P1 loxP sites ("floxed"). Infection of the helper cells that express Cre recombinase with the gutless virus together with the helper virus with a floxed packaging signal should only yield gutless rAV, as the packaging signal is deleted from the DNA of the helper virus. However, if 293-based helper cells are used, the helper virus DNA can recombine with the Ad5 DNA that is integrated in the helper cell DNA. As a result, a wild-type packaging signal, as well as the E1 region, is regained. Thus, also production of gutless rAV on 293- (or 911-) based helper cells can result in the generation of RCA, if an E1-deleted helper virus is used.

Considering the magnitude of the problem, considerable research and effort has been devoted to solving the RCA problem. Strategies to circumvent RCA generation during rAV production have been focused at reducing or eliminating the sequence homology between the vector and the packaging cell line (see the Hehir article, the Imler article, and the Fallaux 1998 article). The present inventors have shown that the combination of PER.C6™ helper cells (available from IntroGene of Leiden, The Netherlands) and matched vectors that do not share homologous sequences eliminates the generation of RCA by homologous recombination (see the Fallaux 1998 article). Note that in such a system, homology can also be provided by plasmid-derived sequences, as the PER.C6™ cell line has been generated by transfection with a cloned adenovirus E1 region. Hehir demonstrated that deletion or relocation of the gene encoding the minor capsid protein IX resulted in a reduction of the frequency of RCA formation (see the Hehir article).

Another strategy that could prevent the formation of RCA is to delete additional essential genes from the vector backbone. Several of such strategies have been developed aiming at reducing the immunogenicity of the rAV. In most cases, rAVs are constructed with an additional deletion in the adenoviral E2 or E4 region. These rAVs are propagated on cell lines that complement both E1 as well as the other gene. Production of such rAVs on appropriate helper cell lines is expected to reduce or eliminate the risk of generating RCA, as multiple recombinations would be required. However, a potential problem associated with the use of 293-based cell lines is that homologous recombination in the E1 region of adenovirus will generate adenoviruses which have reacquired the E1 region, but still have defects in their E2 or E4 genes. Such as adenovirus revertant is not an RCA in the strict sense, as it is not able to replicate independently in human cells. However, the presence of the E1 region in such E1 revertants (designated "REA": revertant E1 adenoviruses) poses another risk; that being the Ad E1 region having the potential to transform and immortalize rodent cells, and, albeit with much lower frequency, some human cell types. E1-containing adenoviruses that are deleted in either E2A or E4 are able to transform primary baby-rat kidney (BRK) cells (see Table 2). In contrast, none of the vectors that are deleted in E1 were able to transform such primary cells (see Table 2).

TABLE 2

Cell transformation by E1-containing adenoviruses

| | Number of transformed foci[a] | |
|---|---|---|
| Virus | m.o.i.[b] 10 | m.o.i.[b] 100 |
| wild-type Ad5 | 1 | 0 |
| DE1: AdCMV-LacZ | 0 | 0 |
| DE4: H5dl355[c] | 1 | 1 |
| DE4: H5dl1014[d] | 3 | 14 |
| DE2A: IG.Ad.DE2A | 0 | 1 |
| DE1DE2A: IG.Ad.LacZ.DE2A | 0 | 0 |

The transformation assay was performed as described previously (see Fallaux 1998 article). Briefly, primary cultures of kidney cells isolated from 6-day old WagRij rats (BRK) in 6-cm culture dishes were infected with a multiplicity of infection of 10 (5 × 10$^6$ particles) or 100 (5 × 10$^7$ particles). Infection of BRK cells with AdCMV-LacZ resulted in 40% (5 × 10$^6$ virus particles) or 80% (5 × 10$^7$ virus particles) blue cells.
As a positive control for focus-formation, BRK cells were transfected with 5 mg pIG.E1A.E1B (see the Fallaux 1998 article). This resulted in the formation of 18 foci per culture dish on average.
[a]Average of four dishes.
[b]m.o.i.: multiplicity of infection.
[c]H5dl355 has a 16-base pair deletion in E4 open reading frame (ORF) 6.
[d]H5dl1014 has a deletion in E4 that affects expression of all E4 ORFs except ORF4.

Ads that carry lethal deletions have in fact been shown to transform cells more efficiently than wild-type Ad5. For example, H5ts125 encodes temperature-sensitive DNA-binding proteins, due to a defect in the E2A region. This adenovirus mutant exhibits a higher transformation frequency at the non-permissive temperature than it does at the permissive temperature. It is speculated that E2- or E4-deleted Ads, in contrast to wild-type Ad, do not contain sequences that are toxic for BRK cells. Although the number of foci obtained by infection with E1-containing Ads was slightly lower compared to the amount of foci that arose upon transfection with an Ad5 E1 plasmid (see Table 2), one should bear in mind that 5×10$^7$ virus particles carry approximately 2 ng DNA, whereas present experimentation used 5 mg plasmid DNA for transfection.

Whether REAs are able to induce tumors in humans is unknown. On the one hand, given the fact that the E1A and E1B proteins contain strong CTL epitopes, the risk may be only theoretical for immunocompetent individuals. On the other hand, REAs may be harmful for immunocomprised patients.

Therefore, it is clear that there is a need to develop novel virus derived vectors and novel packaging cell lines for vectors based on adenoviruses. Furthermore, there is a need to develop methods to screen replication-competent and revertant E1 adenoviruses from recombinant adenoviruses used in gene therapy.

SUMMARY OF THE INVENTION

One embodiment of the present invention relates to a recombinant nucleic acid molecule based on or derived from an adenovirus having at least a functional encapsidating signal and at least one functional Inverted Terminal Repeat or a functional fragment or derivative thereof and having no overlapping sequences which allow for homologous recombination leading to replication-competent virus in a cell into which it is transferred. Preferably, the recombinant nucleic acid molecule is in a linear form and has an Inverted Terminal Repeat at or near both termini. Additionally, it is preferred that the linear form recombinant nucleic acid molecule be essentially in a single stranded form and have at the 3' terminus a sequence complementary to an upstream part of the same strand of the nucleic acid molecule, wherein the sequence is capable of base pairing with the upstream part in a way to be able to function as a start-site for a nucleic acid polymerase, and may include all adenovirus derived genetic information necessary for replication, except for a functional encapsidation signal, preferably resulting from the action of a nucleic acid polymerase on the nucleic acid molecule. The recombinant nucleic acid of this embodiment may include functional E2A and E2B genes or functional fragments or derivatives thereof under control of an E1A independent promoter. The recombinant nucleic acid molecule may also include a host range mutation, and may further include a mutated E2 region rendering at least one of its products temperature sensitive and/or under the control of an inducible promoter. The recombinant nucleic acid molecule may, of course, by a DNA molecule. It is, of course, understood that adenovirus-like particles and packaging cells can be fabricated using the recombinant nucleic acid molecule described in this embodiment.

Another embodiment of the present invention relates to a packaging cell for packaging adenovirus derived nucleic acid molecules, wherein the packaging cell has been provided with one or more recombinant nucleic acid molecules which provide the cell with the ability to express adenoviral gene products derived from at least the E1A region and, preferably, does not have the ability to express E1B products. Preferably, the packaging cell of the present embodiment does not have the ability to express the 21 kD E1B product, which may be the result of the genetic information encoding the 21 kD E1B product not being present. The packaging cells of the present embodiment may be diploid cells, and may be of non-human origin, such as of monkey origin which, preferably, includes a host range mutated E2A region of an adenovirus.

Established cell lines (and not human diploid cells of which 293 and 911 cells are derived) are able to express E1A to high levels without undergoing apoptotic cell death, as occurs in human diploid cells that express E1A in the absence of E1B. Such cell lines are able to trans-complement E1B-defective recombinant adenoviruses, because viruses mutated for E1B 21 kD protein are able to complete viral replication even faster than wild-type adenoviruses (see Telling et. al., "Absence of an Essential Regulatory Influence of the Adenovirus E1B 19-kiloDalton Protein on Viral Growth and Early Gene Expression in Human Diploid W138, HeLa, and A549 cells", *J. Virol* 68, pp. 541–547 (1994), hereby incorporated herein by reference). The constructs are described in detail below and graphically represented in FIGS. 1–5. The constructs are transfected into the different established cell lines and are selected for high expression of E1A. This is done by operatively linking a selectable marker gene (e.g., NEO gene) directly to the E1B promoter. The E1B promoter is transcriptionally activated by the E1A gene product and, therefore, resistance to the selective agent (e.g., G418 in the case NEO is used as the selection marker) results in direct selection for desired expression of the E1A gene.

Yet another embodiment of the present invention relates to a packaging cell for packaging adenovirus derived nucleic acid molecules, wherein the packaging cell has been provided with one or more recombinant nucleic acid molecules which provide the cell with the ability to express adenoviral gene products derived from at least both the E1A and the E2A region and, preferably, does not have the ability to express E1B products. The recombinant nucleic acid molecule encoding the E2A region is, preferably, under the control of an inducible promoter and/or is mutated so that at least one of its products is temperature sensitive. The packaging cell of this embodiment preferably does not have the ability to express E1B products, generally resulting from the genetic information encoding E1B products not being present. The packaging cell of this embodiment may further include the region coding for E1B and/or a marker gene, wherein the marker gene is preferably under the control of the E1B responsive promoter. Furthermore, the packaging cell of the present embodiment, preferably, does not have the ability to express the 21 kD E1B product, which may be the result of the genetic information encoding the 21 kD E1B product not being present. The packaging cells of the present embodiment may be diploid cells, and may be of non-human origin, such as of monkey origin which, preferably, includes a host range mutated E2A region of an adenovirus.

A further embodiment of the present invention relates to a packaging cell harboring nucleotides 80–5788 of the human Adenovirus 5 genome. Preferably, the packaging cell line is derived from diploid human embryonic retinoblasts (HER) that harbors nt. 80–5788 of the Ad5 genome. This cell line, named 911, deposited under no. 95062101 at the ECACC, has many characteristics that make it superior to the commonly used 293 cells (see Fallaux et al., "Characterization of 911: a new helper cell line for the titration and propagation of early-region- 1-deleted adenoviral vectors", *Human Gene Therapy* 7, pp. 215–222 (1996) (hereinafter "the Fallaux 1996 article), hereby incorporated herein by reference).

Still other embodiments of the present invention include a packaging cell harboring nucleotides 459–1713 of the human Adenovirus 5 genome and a packaging cell harboring nucleotides 459–3510 of the human Adenovirus 5 genome. The packaging cells of these two embodiments may be diploid cells, and may be of non-human origin, such as of monkey origin which, preferably, includes a host range mutated E2A region of an adenovirus.

Yet still further embodiments of the present invention include a recombinant nucleic acid molecule based on or derived from an adenovirus, having at least a deletion of nucleotides 459–3510 of the E1 region, and a recombinant nucleic acid molecule based on or derived from an adenovirus, having a deletion of nucleotides 459–1713 of the E1 region.

Yet still another embodiment of the present invention includes a method for intracellular amplification comprising the steps of providing a cell with a linear DNA fragment to be amplified, which fragment is provided with at least a functional part or derivative of an Inverted Terminal Repeat at one terminus and providing the cell with functional E2-derived products necessary for replication of the fragment and allowing the fragment to be acted upon by a DNA polymerase. Preferably, the cell can be provided with genetic material encoding both E2A and E2B products. Most preferably, the cell can be provided with a hairpin-like structure at the terminus of the DNA fragment opposite the Inverted Terminal Repeat.

In another aspect of the present invention, the E2A coding sequences from the recombinant adenovirus genome and transfect these E2A sequences into the (packaging) cell lines containing E1 sequences to complement recombinant adenovirus vectors have been deleted.

Major hurdles in this approach are a) that E2A should be expressed to very high levels and b) that E2A protein is very toxic to cells.

The current invention in yet another aspect, therefore, discloses use of the ts125 mutant E2A gene, which produces a protein that is not able to bind DNA sequences at the non-permissive temperature. High levels of this protein may be maintained in the cells (because it is not toxic at this temperature) until the switch to the permissive temperature is made. This can be combined with placing the mutant E2A gene under the direction of an inducible promoter, such as for instance tet, methallothionein, steroid inducible promoter, retinoic acid β-receptor or other inducible systems. However, in yet another aspect of the invention, the use of an inducible promoter to control the moment of production of toxic wild-type E2A is disclosed.

Two salient additional advantages of E2A-deleted recombinant adenovirus are the increased capacity to harbor heterologous sequences and the permanent selection for cells that express the mutant E2A. This second advantage relates to the high frequency of reversion of ts125 mutation. When reversion occurs in a cell line harboring ts125 E2A, this will be lethal to the cell. Therefore, there is a permanent selection for those cells that express the ts125 mutant E2A protein. Thus, one aspect of the present invention which relates to the generation of E2A-deleted recombinant adenovirus eliminates the problem of reversion in the adenoviruses.

In yet another aspect of the invention, a further improvement in the use of non-human cell lines as packaging cell lines is disclosed. For GMP production of clinical batches of recombinant viruses, it is desirable to use a cell line that has been used widely for production of other biotechnology products. Most of the latter cell lines are from monkey origin, which have been used to produce, for example, vaccines.

These cells cannot be used directly for the production of recombinant human adenovirus, as human adenovirus cannot replicate, or only replicate to low levels, in cells of monkey origin. A block in the switch of early to late phase of adenovirus lytic cycle is underlying defective replication. However, host range ("hr") mutations in the human adenovirus genome are described (hr 400–404) which allow replication of human viruses in monkey cells. These mutations reside in the gene encoding E2A protein (see Klessig and Grodzicker, "Mutations That Allow Human Ad2 and Ad5 to Express Late Genes in Monkey Cells Maps in the Viral Gene Encoding the 72 k DNA-binding Protein", Cell 17, pp. 957–966 (1979), Klessig et al., "Construction of Human Cell Lines Which Contain and Express the Adenovirus DNA Binding Protein Gene by Cotransformation with the HSV-1 tk Gene", Virus Res. 1, pp. 169–188 (1984), and Rice and Klessig, "Isolation and Analysis of Adenovirus Type 5 Mutants Containing Deletions in the Gene Encoding the DNA-Binding Protein", J. Virol. 56, pp. 767–778 (1985) (hereinafter "the Rice and Klessing article"), all of which are hereby incorporated herein by reference). Moreover, mutant viruses have been described that harbor both the hr and temperature-sensitive ts125 phenotype (see Brough et al., "Restricted Changes in the Adenovirus DNA-Binding Protein that Lead to Extended Host Range or Temperature-Sensitive Phenotypes", J. Virol. 55, pp. 206–212 (1985) (hereinafter "the Brough article"), hereby incorporated herein by reference, and the Rice and Klessig article).

Therefore, the present invention includes the generation of packaging cell lines of monkey origin (e.g., VERO, CV1) that harbor:

a. E1 sequences, to allow replication of E1/E2-defective adenoviruses; and b. E2A sequences, containing the hr mutation and the ts125 mutation, names ts400 (see the Brough article and the Rice and Klessig article) to prevent cell death by E2A overexpression; and/or c. E2A sequences, just containing the hr mutation, under the control of an inducible promoter; and/or d. E2A sequences, containing the hr mutation and the ts125 mutation (ts400), under the control of an inducible promoter.

Furthermore, the present invention includes:

1. Packaging constructs that are mutated or deleted for E1B 21 kD, but just express the 55 kD protein.

2. Packaging constructs to be used for generation of complementing packaging cell lines from diploid cells (not exclusively of human origin) without the need of selection with marker genes. These cells are immortalized by expression of E1A. However, in this particular case, expression of E1B is essential to prevent apoptosis induced by E1A proteins. Selection of E1-expressing cells is achieved by selection for focus formation (immortalization), as described for 293 cells (see the Graham article) and 911 cells (see the Fallaux 1996 article), that are E1-transformed human embryonic kidney (HEK) cells and human embryonic retinoblasts (HER), respectively.

3. After transfection of HER cells with construct pIG.E1B (FIG. 4), seven independent cell lines could be established. These cell lines were designated PER.C1, PER.C3, PER.C4, PER.C5, PER.C6™, PER.C8 and PER.C9. PER denotes PGK-E1-Retinoblasts. These cell lines express E1A and E1B proteins, are stable (e.g., PER.C6™ for more than 57 passages) and complement E1-defective adenovirus vectors. Yields of recombinant adenovirus obtained on PER cells are a little higher than obtained on 293 cells. One of these cell lines (PER.C6™) has been deposited at the ECACC under number 96022940.

4. New adenovirus vectors with extended E1 deletions (deletion nt. 459–3510). Those viral vectors lack sequences homologous to E1 sequences in the packaging cell lines. These adenoviral vectors contain pIX promoter sequences and the pIX gene, as pIX (from its natural promoter sequences) can only be expressed from the vector and not by packaging cells (see Matsui et al., Adenovirus 2 Peptide IX is Expressed Only on Replicated DNA Molecules", Mol. Cell Biol. 6, pp. 4149–4154 (1986), hereby incorporated herein by reference, and the Imler article).

5. E2A-expressing packaging cell lines preferably based on either E1A-expressing established cell lines or E1A–E1B-expressing diploid cells. E2A expression is either under the control of an inducible promoter or the E2A ts125 mutant is driven by either an inducible or a constitutive promoter.

6. Recombinant adenovirus vectors as described before (see 4 above) but carrying an additional deletion of E2A sequences.

7. Adenovirus packaging cells from monkey origin that are able to trans-complement E1-defective recombinant adenoviruses. They are preferably co-transfected with pIG E1AE1B and pIG.NEO, and selected for NEO resistance. Such cells expressing E1A and E1B are able to transcomplement E1-defective recombinant human adenoviruses, but will do so inefficiently because of a block of the synthesis of late adenovirus proteins in cells of monkey origin (Klessig and Grodzicker, 1979). To overcome this problem, the present invention relates to generating recombinant adenoviruses that harbor a host-range mutation in the E2A gene, allowing human adenoviruses to replicate in monkey cells. Such viruses are generated as described in FIG. 12, except DNA from a hr-mutant is used for homologous recombination.

8. Adenovirus packaging cells from monkey origin as described under 7, except that they will also be co-transfected with E2A sequences harboring the hr mutation. This allows replication of human adenoviruses lacking E1 and E2A (see under 6). E2A in these cell lines is either under the control of an inducible promoter or the tsE2A mutant is used. In the latter case, the E2A gene will thus carry both the ts mutation and the hr mutation (derived from ts400). Replication-competent human adenoviruses have been described that harbor both mutations (see the Brough article and the Rice and Klessig article).

A further aspect of the invention provides otherwise improved adenovirus vectors, as well as novel strategies for generation and application of such vectors and a method for the intracellular amplification of linear DNA fragments in mammalian cells.

The so-called "minimal" adenovirus vectors according to the present invention retain at least a portion of the viral genome that is required for encapsidation of the genome into virus particles (the encapsidation signal), as well as at least one copy of at least a functional part or a derivative of the Inverted Terminal Repeat (ITR), that is, DNA sequences derived from the termini of the linear adenovirus genome. The vectors according to the present invention will also contain a transgene linked to a promoter sequence to govern expression of the transgene. Packaging of the so-called minimal adenovirus vector can be achieved by co-infection with a helper virus or, alternatively, with a packaging-deficient replicating helper system as described below.

Adenovirus-derived DNA fragments that can replicate in suitable cell lines and that may serve as a packaging-deficient replicating helper system are generated as follows. These DNA fragments retain at least a portion of the transcribed region of the "late" transcription unit of the adenovirus genome and carry deletions in at least a portion of the E1 region and deletion in at least a portion of the encapsidation signal. In addition, these DNA fragments contain at least one copy of an inverted terminal repeat (ITR). At one terminus of the transfected DNA molecule an ITR is located. The other end may contain an ITR, or alternatively, a DNA sequence that is complementary to a portion of the same strand of the DNA molecule other than the ITR. If, in the latter case, the two complementary sequences anneal, the free 3'-hydroxyl group of the 3' terminal nucleotide of the hairpin-structure can serve as a primer for DNA synthesis by cellular and/or adenovirus-encoded DNA polymerases, resulting in conversion into a double-stranded form of at least a portion of the DNA molecule. Further replication initiating at the ITR will result in a linear double-stranded DNA molecule, that is flanked by two ITR's, and is larger than the original transfected DNA molecule (see FIG. 13). This molecule can replicate itself in the transfected cell by virtue of the adenovirus proteins encoded by the DNA molecule and the adenoviral and cellular proteins encoded by genes in the host-cell genome. This DNA molecule cannot be encapsidated due to its large size (greater than 39000 base pairs) or due to the absence of a functional encapsidation signal. This DNA molecule is intended to serve as a helper for the production of defective adenovirus vectors in suitable cell lines.

The present invention also comprises a method for the amplification of linear DNA fragments of variable size in suitable mammalian cells. These DNA fragments contain at least one copy of the ITR at one of the termini of the fragment. The other end may contain an ITR, or alternatively, a DNA sequence that is complementary to a portion of the same strand of the DNA molecule other than the ITR. If, in the latter case, the two complementary sequences anneal, the free 3'-hydroxyl group of the 3' terminal nucleotide of the hairpin-structure can serve as a primer for DNA synthesis by cellular and/or adenovirus-encoded DNA polymerases, resulting in conversion of the displaced strand into a double stranded form of at least a portion of the DNA molecule. Further replication initiating at the ITR will result in a linear double-stranded DNA molecule that is flanked by two ITRs and which is larger than the original transfected DNA molecule. A DNA molecule that contains ITR sequences at both ends can replicate itself in transfected cells by virtue of the presence of at least the adenovirus E2 proteins (viz. the DNA-binding protein (DBP), the adenovirus DNA polymerase (Ad-pol), and the preterminal protein (pTP). The required proteins may be expressed from adenovirus genes on the DNA molecule itself, from adenovirus E2 genes integrated in the host-cell genome, or from a replicating helper fragment, as described above.

Several groups have shown that the presence of ITR sequences at the end of DNA molecules are sufficient to generate adenovirus minichromosomes that can replicate, if the adenovirus-proteins required for replication are provided in trans, such as by infection with a helper virus (Hu et al., "Symmetrical Adenovirus Minichromosomes Have Hairpin Replication Intermediates", *Gene* 110, pp. 145–150 (1992) (hereinafter "the Hu article"), Wang, K., and Pearson, G. D., "Adenovirus Sequences Required for Replication In Vivo", *Nucl. Acids Res.* 13, pp. 5173–5187 (1985), and Hay et al., "Replication of Adenovirus Minichromosomes", *J. Mol. Biol.* 174, pp. 493–510 (1984), all of which are incorporated herein by reference). The Hu article observed the presence and replication of symmetrical adenovirus minichromosome-dimers after transfection of plasmids containing a single ITR. The authors were able to demonstrate that these dimeric minichromosomes arise after tail-to-tail ligation of the single ITR DNA molecules. In DNA extracted from defective adenovirus type 2 particles, dimeric molecules of various sizes have also been observed using electron-microscopy (see Daniell, E. "Genome Structure of Incomplete Particles of Adenovirus", *J. Virol.* 19, pp. 685–708 (1976) (hereinafter "the Daniell article), hereby incorporated herein by reference). It was suggested that the incomplete genomes were formed by illegitimate recombination between different molecules and that variations in the position of the sequence at which the illegitimate base pairing occurred were responsible for the heterogeneous nature of the incomplete genomes. Based on this mechanism it was speculated that, in theory, defective molecules with a total length of up to two times the normal genome could be generated. Such molecules could contain duplicated sequences from either end of the genome. However, no DNA molecules larger than the full-length virus were found packaged in the defective particles (see the Daniell article). This can be explained by the size-limitations that apply to the packaging. In addition, it was observed that in the virus particles DNA-molecules with a duplicated left-end predominated over those containing the right-end terminus (see the Daniell article). This is fully explained by the presence of the encapsidation signal near that left-end of the genome (see Gräble, M., and Hearing, P., "Adenovirus Type 5 Packaging Domain is Composed of a Repeated Element That is Functionally Redundant", *J. Virol.* 64, pp. 2047–2056 (1990); Gräble, M., and Hearing, P., "cis and trans Requirements for the Selective Packaging of Adenovirus Type-5 DNA", *J Virol* 66, pp. 723–31 (1992); and Hearing et al., "Identification of a Repeated Sequence Element Required for Efficient Encapsidation of the Adenovirus Type 5 Chromosome", *J. Virol.* 61, pp. 2555–2558 (1987), all of which are hereby incorporated herein by reference).

The major problems associated with the current adenovirus-derived vectors are:

A) The strong immunogenicity of the virus particle.

B) The expression of adenovirus genes that reside in the adenoviral vectors, resulting in a Cytotoxic T-cell response against the transduced cells.

C) The low amount of heterologous sequences that can be accommodated in the current vectors (up to maximum of approximately 8000 bp. of heterologous DNA).

Ad A) The strong immunogenicity of the adenovirus particle results in an immunological response of the host, even after a single administration of the adenoviral vector. As a result of the development of neutralizing antibodies, a subsequent administration of the virus will be less effective or even completely ineffective. However, a prolonged or persistent expression of the transferred genes will reduce the number of administrations required and may bypass the problem.

Ad B) Experiments performed by Wilson and collaborators (see U.S. Pat. No. 5,652,224) have demonstrated that after adenovirus-mediated gene transfer into immunocompetent animals, the expression of the transgene gradually decreases and disappears approximately 2–4 weeks post-infection (see the Yang 1994a article and the Yang 1994b article). This is caused by the development of a Cytotoxic T-Cell (CTL) response against the transduced cells. The CTLs were directed against adenovirus proteins expressed by the viral vectors. In the transduced cells synthesis of the adenovirus DNA-binding protein (the E2A-gene product), penton and fiber proteins (late-gene products) could be established. These adenovirus proteins, encoded by the viral vector, were expressed despite deletion of the E1 region. This demonstrates that deletion of the E1 region is not sufficient to completely prevent expression of the viral genes (see the Englehardt 1994a article).

Ad C) Studies by Graham and collaborators have demonstrated that adenoviruses are capable of encapsidating DNA of up to 105% of the normal genome size (see Bett et al., "Packaging Capacity and Stability of Human Adenovirus Type-5 Vectors", *J. Virol.* 67, pp. 5911–5921 (1993), hereby incorporated herein by reference). Larger genomes tend to be unstable resulting in loss of DNA sequences during propagation of the virus. Combining deletions in the E1 and E3 regions of the viral genomes increases the maximum size of the foreign DNA that can be encapsidated to approx. 8.3 kb. In addition, some sequences of the E4 region appear to be dispensable for virus growth (adding another 1.8 kb to the maximum encapsidation capacity). Also the E2A region can be deleted from the vector, when the E2A gene product is provided in trans in the encapsidation cell line, adding another 1.6 kb. It is, however, unlikely that the maximum capacity of foreign DNA can be significantly increased further than 12 kb.

Thus, the present invention includes a new strategy for the generation and production of helper-free stocks of recombinant adenovirus vectors that can accommodate up to 38 kb of foreign DNA. Only two functional ITR sequences, and sequences that can function as an encapsidation signal need to be part of the vector genome. Such vectors are called minimal adenovectors. The helper functions for the minimal adenovectors are provided in trans by encapsidation-defective replication-competent DNA molecules that contain all the viral genes encoding the required gene products, with the exception of those genes that are present in the host-cell genome, or genes that reside in the vector genome.

With the development of new generations of rAVs, the RCA problem has become more complex using conventional cell lines like 293 and 911 because a rAV revertant can be the classical RCA (i.e., which lost the transgene, regained E1, and is replication-competent), or revertant E1 adenoviruses ("REA") (i.e., reacquired E1, but is still replication-defective). Thus, the present invention further involves screening rAV lots, especially those intended for clinical use, for the presence of adenovirus E1 sequences, as this will reveal RCAs, as well as REAs. Further, the present invention involves employing vector systems that prevent the formation of RCA and/or REA. Currently, adenoviral vectors are the most efficient vectors for gene-therapy applications. Adenoviral vectors are, therefore, being manipulated extensively to make them suitable for specific applications. Such developments should be accompanied by the parallel development of procedures to make rAV a safe pharmaceutical product: a manufacturing process that prevents contamination of the viral preparations with either RCA or replication-defective revertants. Despite the fact that no accidents have happened so far with RCA-contaminated rAV preparations in clinical trials, for improving the Ad vector system for gene therapy purposes, therapeutic potential and safety should be enhanced. The use of PER.C6™ cells and non-overlapping vectors eliminates this problem, and allows production of safe clinical grade batches of rAVs. Only safe production systems, developed in parallel with appropriate testing methods, will warrant safe clinical application of rAVs. It is also an aspect of the present invention to molecularly characterize the revertants that are generated in the newer helper/vector combinations.

The applications of the disclosed inventions are outlined below and will be illustrated in the experimental part, which is only intended for that purpose, and should not be used to reduce the scope of the present invention as understood by the person skilled in the art.

BRIEF DESCRIPTION OF THE DRAWINGS

While the specification concludes with claims particularly pointing out and distinctly claiming that which is regarded as the present invention, the advantages of this invention can be more readily ascertained from the following description of the invention when read in conjunction with the accompanying drawings in which:

FIGS. 11A and 11B illustrate new adenovirus packaging constructs do not have sequence overlap with new adenovirus vectors according to the present invention;

FIG. 15 illustrates a potential hairpin conformation of a single-stranded DNA molecule that contains the HP/asp sequence according to the present invention;

DETAILED DESCRIPTION OF THE PREFERRED EMBODIMENTS

Figure 1:
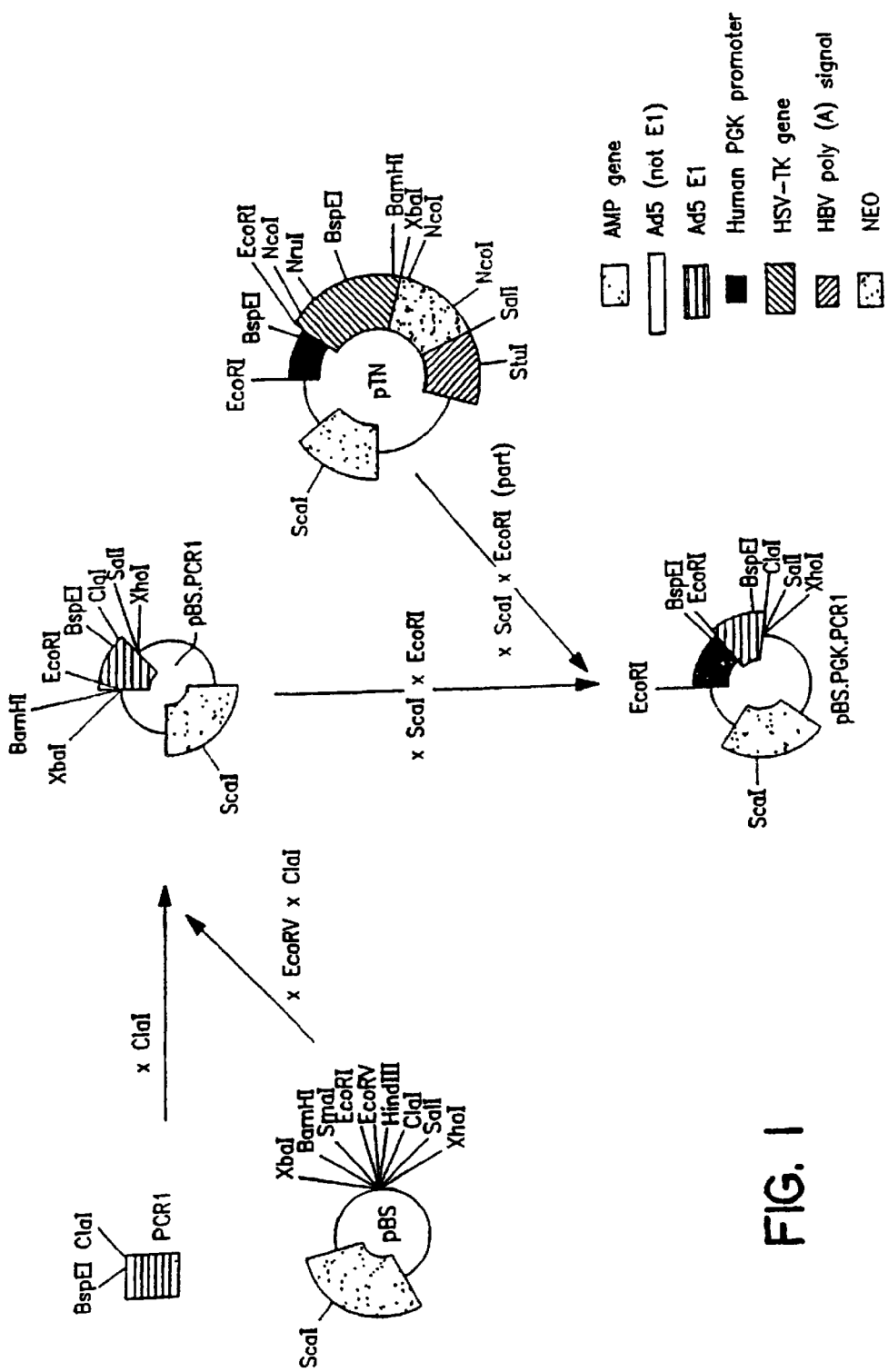
FIG. 1 illustrates the construction of pBS.PGK.PCRI according to the present invention.

The constructs of the present invention, in particular pIG.E1A.E1B, may be used to transfect diploid human cells, such as Human Embryonic Retinoblasts (HER), Human Embryonic Kidney cells (HEK), and Human Embryonic Lung cells (HEL). Transfected cells are preferably selected for transformed phenotype (focus formation) and tested for their ability to support propagation of E1-deleted recombinant adenovirus, such as IG.Ad.MLPI.TK. Such cell lines are preferably used for the generation and (large-scale) production of E1-deleted recombinant adenoviruses. Such cells, infected with recombinant adenovirus, are also intended to be used in vivo as a local producer of recombinant adenovirus, such as for the treatment of solid tumors. In the presently described embodiment, 911 cells are used for the titration, generation and production of recombinant adenovirus vectors (see the Fallaux 1996 article).

HER cells transfected with pIG.E1A.E1B have resulted in 7 independent clones (called PER cells). These clones may be used for the production of E1-deleted (including non-overlapping adenovirus vectors) or E1-defective recombinant adenovirus vectors and provide the basis for introduction of, for example, E2B or E2A constructs (e.g., ts125 E2A, see below), E4 etc., that will allow propagation of adenovirus vectors that have mutations in, for example, E2A or E4.

In addition, diploid cells of other species that are permissive for human adenovirus, such as the cotton rat (*Sigmodon hispidus*) (see Pacini et al., *J. Infect. Dis.* 150, pp. 92–97 (1984), hereby incorporated herein by reference), Syrian hamster (see Morin et al., "Recombinant Adenovirus Induces Antibody Response to Hepatitis B Virus Surface Antigens", *Proc. Natl. Acad. Sci. USA* 84, pp. 4626–4630 (1987), hereby incorporated herein by reference), or chimpanzee (see Levrero et al., "Defective and Nondefective Adenovirus Vectors for Expressing Foreign Genes In Vitro and In Vivo," *Gene* 101, pp. 195–202 (1991) (hereinafter "the Levrero article"), hereby incorporated herein by reference) can be immortalized with these constructs. Such cells, infected with recombinant adenovirus, are also intended to be used in vivo for the local production of recombinant adenovirus, such as for the treatment of solid tumors.

The constructs of the present invention, in particular pIG.E1A.NEO, can be used to transfect established cells, such as A549 (human bronchial carcinoma), KB (oral carcinoma), MRC-5 (human diploid lung cell line) or GLC cell lines (small cell lung cancer ) (see de Leij et al., "Characterization of Three New Variant Type Cell Lines Derived from Small Cell Carcinoma of the Lung", *Cancer Res.* 45, pp. 6024–6033 (1985) and Postmus et al., "Two Small Cell Lung Cancer Cell Lines Established from Rigid Bronchoscope Biopsies", *Eur. J. Clin. Oncol.* 24, pp. 753–763 (1988), both hereby incorporated herein by reference) and selected for NEO resistance. Individual colonies of resistant cells are isolated and tested for their capacity to support propagation of E1-deleted recombinant adenovirus, such as IG.Ad.MLPI.TK. When propagation of E1-deleted viruses on E1A-containing cells is possible, such cells can be used for the generation and production of E1-deleted recombinant adenovirus. They can also be used for the propagation of E1A-deleted/E1B-retained recombinant adenovirus.

Established cells can also be co-transfected with pIG.E1A.E1B and pIG.NEO (or another NEO-containing expression vector). Clones resistant to G418 are tested for their ability to support propagation of E1-deleted recombinant adenovirus, such as IG.Ad.MLPI.TK and used for the generation and production of E1-deleted recombinant adenovirus and will be applied in vivo for local production of recombinant virus, as described for the diploid cells (see above).

All cell lines, including transformed diploid cell lines or NEO-resistant established lines, can be used as the basis for the generation of 'next generation' packaging cells lines that support propagation of E1-defective recombinant adenoviruses, and that also carry deletions in other genes, such as E2A and E4. Moreover, they will provide the basis for the generation of minimal adenovirus vectors as disclosed herein.

Packaging cells expressing E2A sequences are preferably used for the generation and (large scale) production of E2A-deleted recombinant adenovirus. The newly generated human adenovirus packaging cell lines or cell lines derived from species permissive for human adenovirus (E2A or ts125E2A; E1A+E2A; E1A+E1B+E2A; E1A−E2A/ts125; E1A+E1B−E2A/ts125) or non-permissive cell lines, such as monkey cells (hrE2A or hr+ts125E2A; E1A+hrE2A; E1A+ E1B+hrE2A; E1A+hrE2A/ts125; E1A−E1B+hrE2A/ts125), are preferably used for the generation and (large scale) production of E2A deleted recombinant adenovirus vectors. In addition, they may be applied in vivo for local production of recombinant virus, as described for the diploid cells (see above).

The newly developed adenovirus vectors harboring an E1 deletion of nt. 459–3510 are preferably used for gene transfer purposes. These vectors may also be the basis for the development of further deleted adenovirus vectors that are mutated for E2A, E2B or E4, for example. Such vectors may be generated on the newly developed packaging cell lines described above.

Figure 13:
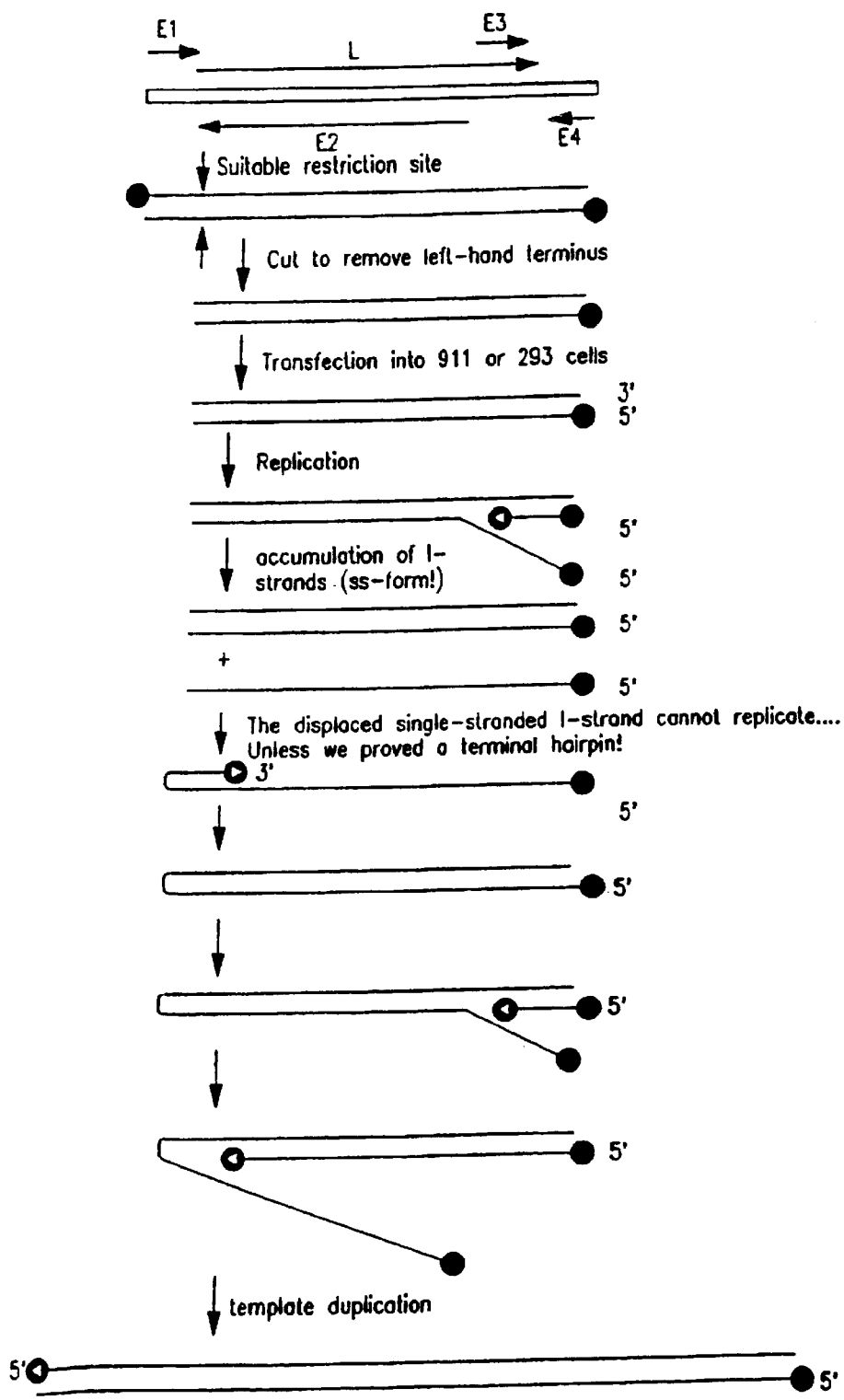
FIG. 13 illustrates the adenovirus double-stranded DNA genome indicating the approximate locations of E1, E2, E3, E4, and L regions according to the present invention.
Figure 14:
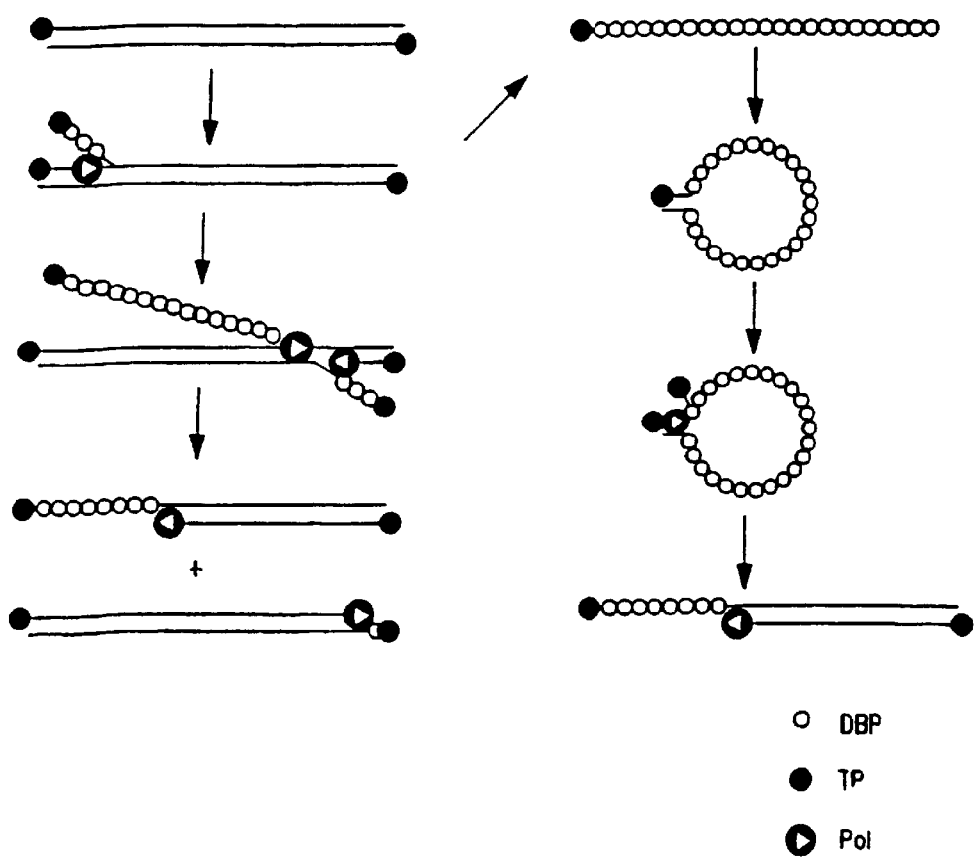
FIG. 14 illustrates the adenovirus genome as shown in the top left with the origins or replication located within the left and right ITRs at the genome ends.

One aspect of the present invention includes adenovirus packaging constructs to be used for the packaging of minimal adenovirus vectors which may have the following characteristics:

a. The packaging construct replicates.
b. The packaging construct cannot be packaged because the packaging signal is deleted.
c. The packaging construct contains an internal hairpin-forming sequence (see FIG. 15).
d. Because of the internal hairpin structure, the packaging construct is duplicated. In other words, the DNA of the packaging construct becomes twice as long as it was before transfection into the packaging cell (in our sample it duplicates from 35 kb to 70 kb). This duplication also prevents packaging. Note that this duplicated DNA molecule has ITR's at both termini (see e.g., FIG. 13).
e. This duplicated packaging molecule is able to replicate like a 'normal adenovirus' DNA molecule.
f. The duplication of the genome is a prerequisite for the production of sufficient levels of adenovirus proteins, required to package the minimal adenovirus vector.
g. The packaging construct has no overlapping sequences with the minimal vector or cellular sequences that may lead to generation of RCA by homologous recombination.

This packaging system can be used to product minimal adenovirus vectors. The advantages of minimal adenovirus vectors for gene therapy of vaccination purposes are well known (such as accommodation of up to 38 kb and gutting of all potentially toxic and immunogenic adenovirus genes).

Adenovirus vectors containing mutations in essential genes (including minimal adenovirus vectors) can also be propagated using this system.

Minimal adenovirus vectors may be generated using the helper functions provided in trans by packaging-deficient replicating helper molecules. The adenovirus-derived ITR sequences serve as origins of DNA replication in the presence of at least the E2-gene products. When the E2 gene products are expressed from genes in the vector genome (the gene(s) must be driven by an E1-independent promoter), the vector genome can replicate in the target cells. This will allow a significantly increased number of template molecules in the target cells and, as a result, an increased expression of the genes of interest encoded by the vector. This is of particular interest for approaches of gene therapy to treat cancer.

A similar approach could also be taken if amplification of linear DNA fragments is desired. DNA fragments of known or unknown sequence could be amplified in cells containing the E2-gene products if at least one ITR sequence is located near at its terminus. There are no apparent constraints on the size of the fragment. Even fragments much larger than the adenovirus genome (36 kb) could be amplified using this approach. It is thus possible to clone large fragments in mammalian cells without either shuttling the fragment into bacteria (such as *E. coli*) or use the polymerase chain reaction ("PCR"). At the end stage of a productive adenovirus infection, a single cell can contain over 100,000 copies of the viral genome. In an optimal situation, the linear DNA fragments can be amplified to similar levels. Thus, one should be able to extract more than 5 µg of DNA fragment per 10 million cells (for a 35-kbp fragment). This system can be used to express heterologous proteins equivalent to the Simian Virus 40-based COS-cell system for research or for therapeutic purposes. In addition, the system can be used to identify genes in large fragments of DNA. Random DNA fragments may be amplified (after addition of ITRs) and expressed during intracellular amplification. Election or selection of those cells with the desired phenotype can be used to enrich the fragment of interest and to isolate the gene.

EXAMPLE

A cell line was generated that harbors E1 sequences of adenovirus type 5, and was able to trans-complement E1-deleted recombinant adenovirus (see the Fallaux 1996 article). This cell line was obtained by transfection of human diplid human embryonic retinoblasts (HER) with pAd5XhoIC, that contains nt. 80–5788 of Ad5; one of the resulting transformants was designated 911. This cell line has been shown to be very useful in the propagation of E1-defective recombinant adenovirus. It was found to be superior to the 293 cells. Unlike 293 cells, 911 cells lack a fully transformed phenotype, which most likely is the cause of performing better as adenovirus packaging line. Further, plaque assays can be performed faster with 911 cells (4–5 days instead of 8–14 days on 293), monolayers of 911 cells survive better under agar overlay as required for plaque assays, and higher amplification of E1-deleted vectors is achieved with 911 cells. In addition, unlike 293 cells that were transfected with sheared adenoviral DNA, 911 cells were transfected using a defined construct. Transfection efficiencies of 911 cells are comparable to those of 293 cells.

Adenovirus sequences are derived either from pAd5.SalB, containing nt. 80–9460 of human adenovirus type 5 (see Bernards et al., "Role of Adenovirus Types 5 and 12 Early Region 1b Tumor Antigens in Oncogenic Transformation", *Virology* 127, pp. 45–53 (1983), hereby incorporated herein by reference) or from wild-type Ad5 DNA. pAd5.SalB was digested with SalI and XhoI and the large fragment was religated and this new clone was named pAd5.X/S. The pTN construct (constructed by Dr. R. Vogels, IntroGene, The Netherlands) was used as a source for the human PGK promoter and the NEO gene.

Transcription of E1A sequences in the new packaging constructs is driven by the human PGK promoter (see Michelson et al., "Isolation and DNA Sequence of a Full-Length cDNA Clone for Human X-Chromosome Encoded Phosphoglycerate Kinase", *Proc. Natl. Acad. Sci. USA* 80, pp. 472–476 (1983), and Singer-Sam et al., "Sequence of the Promoter Region of the Gene for X-Linked 3-Phosphoglycerate Kinase", *Gene* 32, pp. 409–417 (1984), both hereby incorporated herein by reference), derived from plasmid pTN, which uses pUC119 (see Vieira, J. and Messing, J., "Production of Single Stranded Plasmid DNA", pp. 3–11: *Methods in Enzymology*, Acad. Press Inc. (1987), hereby incorporated herein by reference) as a backbone. This plasmid was also used as a source for NEO gene fused to the Hepatitis B Virus (HBV) poly-adenylation signal.

FIG. 1 illustrates the construction of pBS.PGK.PCRI with encodes, the human phosphoglycerate kinase promoter (PGK) operatively linked to adenovirus 5 (Ad5) E1 nucleotides 459–916. In order to replace the E1 sequences of Ad5

(ITR, origin of replication and packaging signal) by heterologous sequences, E1 sequences (nt. 459 to nt. 960) of Ad5 were amplified by PCR, using primers Ea-1 (SEQ ID NO:1) and Ea-2 (SEQ ID NO:2) (see Table 3). The resulting PCR product was digested with ClaI and ligated into Bluescript (Stratagene), predigested with ClaI and EcoRV, resulting in construct pBS.PCRI.

Vector pTN was digested with restriction enzymes EcoRI (partially) and ScaI, and the DNA fragment containing the PGK promoter sequences was ligated into PBS.PCRI digested with ScaI and EcoRi. The resulting construct PBS.PGK.PCRI contains the human PGK promoter operatively linked to Ad5 E1 sequences from nt. 459 to nt. 916.

Table 3 lists the primers used for PCR amplification of DNA fragments used for generation of constructs (Group 1), the PCR primer sets used to create the SalI and Asp718 sites juxtaposed to the ITR sequences (Group 2), the synthetic oligonucleotide pair used to generate a synthetic hairpin, recreating as Asp718 site at one of the termini if inserted in the Asp718 site (Group 3), and the synthetic oligonucleotide pair used to generate a synthetic hairpin, containing the ClaI recognition site used for hairpin formation (Group 4).

TABLE 3

Group 1

| | | |
|---|---|---|
| Ea-1 | CGTGTAGTGTATTTATACCCG | SEQ ID NO:1<br>PCR amplification Ad5 nt459→ |
| Ea-2 | TCGTCACTGGGTGGAAAGCCA | SEQ ID NO:2<br>PCR amplification Ad5 nt960← |
| Ea-3 | TACCCGCCGTCCTAAAATGGC | SEQ ID NO:3<br>(nt. 1284–1304 of Ad5 genome) |
| Ea-5 | TGGACTTGAGCTGTAAACGC | SEQ ID NO:4<br>(nt. 1514–1533 of Ad5 genome) |
| Ep-2 | GCCTCCATGGAGGTCAGATGT | SEQ ID NO:5<br>(nt. 1721–1702 of Ad5 genome)<br>introduction of NcoI site |
| Eb-1 | GCTTGAGCCCGAGACATGTC | SEQ ID NO:6<br>(nt. 3269–3289 of Ad5 genome) |
| Eb-2 | CCCCTCGAGCTCAATCTGTATCTT | SEQ ID NO:7<br>(nt. 3508–3496 of Ad5 genome)<br>introduction of XhoI site |
| SV40-1 | GGGGGATCCGAACTTGTTTATTGCAGC | SEQ ID NO:8<br>Introduction BamHI site<br>(nt. 2182–2199 of pMLP.TK)<br>adaption of recombinant adenoviruses |
| SV40-2 | GGGAGATCTAGACATGATAAGATAC | SEQ ID NO:9<br>Introduction BglII site<br>(nt. 2312–2297 of pMLP.TK) |
| Ad5-1 | GGGAGATCTGTACTGAAATGTGTGGGC | SEQ ID NO:10<br>Introduction BglII site<br>(nt. 2496–2514 of pMLP.TK) |
| Ad5-2 | GGAGGCTGCAGTCTCCAACGGCGT | SEQ ID NO:11<br>(nt. 2779–2756 of pMLP.TK) |
| ITR1 | GGGGGATCCTCAAATCGTCACTTCCGT | SEQ ID NO:12<br>nt35737–35757 of Ad5<br>(introduction of BamHI site) |
| ITR2 | GGGGTCTAGACATCATCAATAATATAC | SEQ ID NO:13<br>nt35935–35919 of Ad5<br>(introduction of XbaI) |

Group 2

| | | |
|---|---|---|
| PCR/ML P1 | GGCGAATTCGTCGACATCATCAATAATATACC | SEQ ID NO:14<br>(Ad5 nt. 10–18) |
| PCR/ML P2 | GGCGAATTCGGTACCATCATCAATAATATACC | SEQ ID NO:15<br>(Ad5 nt. 10–18) |
| PCR/ML P3 | CTGTGTACACCGGCGCA | SEQ ID NO:16<br>(Ad5 nt. 200–184) |

Group 3

| | | |
|---|---|---|
| HP/asp1 | GTACACTGACCTAGTGCCGCCCGGGCAA<br>AGCCCGGGCGGCACTAGGTCAG | SEQ ID NO:17 |
| HP/asp2 | GTACCTGACCTAGTGCCGCCCGGGCTTT<br>GCCCGGGCGGCACTAGGTCAGT | SEQ ID NO:18 |

Group 4

| | | |
|---|---|---|
| HP/cla1 | GTACATTGACCTAGTGCCGCCCGGGCAA<br>AGCCCGGGCGGCACTAGGTCAATCGAT | SEQ ID NO:19 |
| HP/cla2 | GTACATCGATTGACCTAGTGCCGCCCGG<br>GCTTTGCCCGGGCGGCACTAGGTCAAT | SEQ ID NO:20 |

Figure 2:
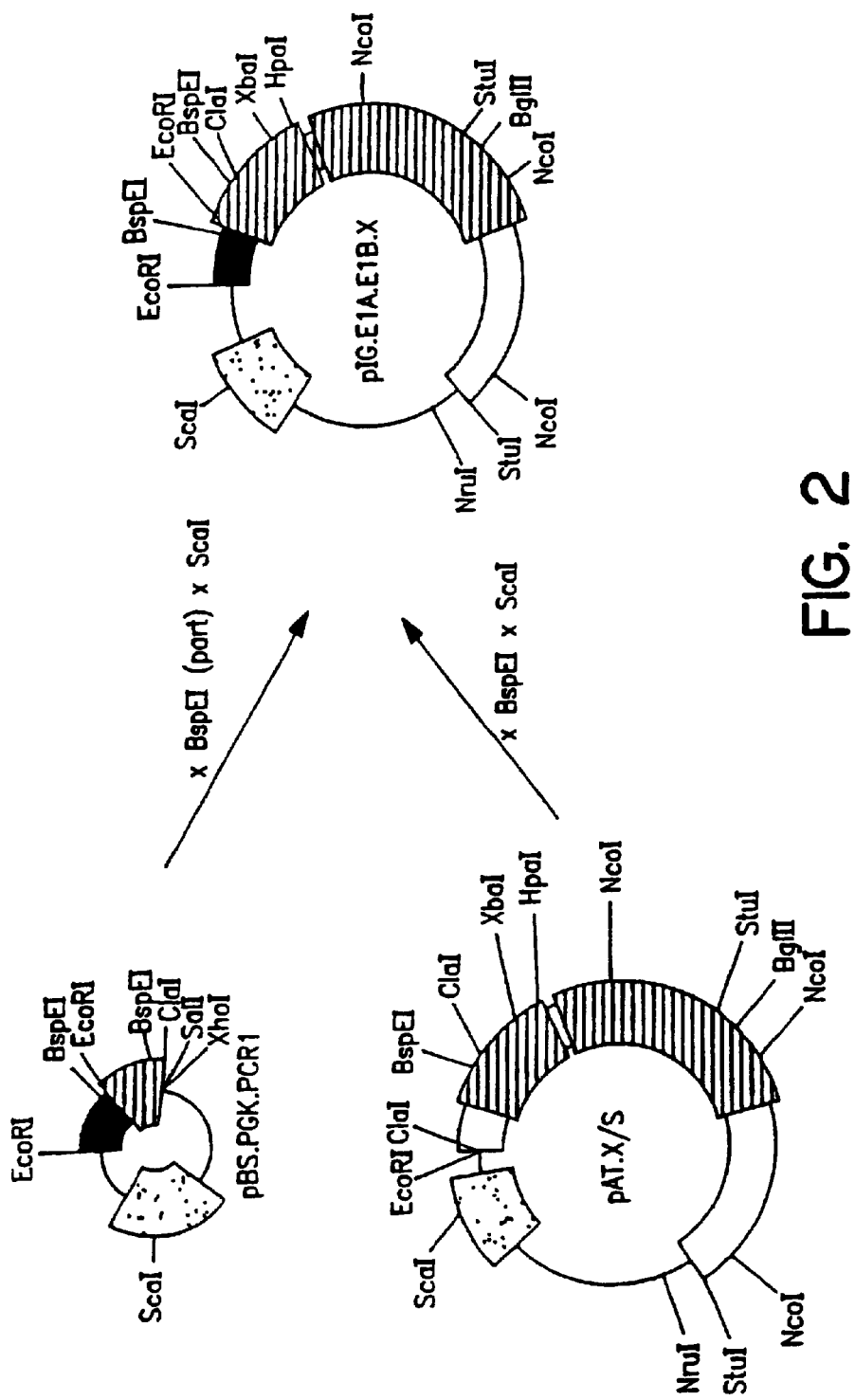
FIG. 2 illustrates the construction of pIG.E1A.E1B.X according to the present invention.

FIG. 2 illustrate the construction of pIG.E1A.E1B.X which was made by replacing the ScaI-BspEI fragment of pAT-X/S by the corresponding fragment from PBS.PGK-.PCRI (containing the PGK promoter linked to E1A sequences). pIG.E1A.E1B.X contains the E1A and E1B coding sequences under the direction of the PGK promoter. As Ad5 sequences from nt. 459 to nt. 5788 are present in this construct, also pIX protein of adenovirus is encoded by this plasmid.

Figure 3A:
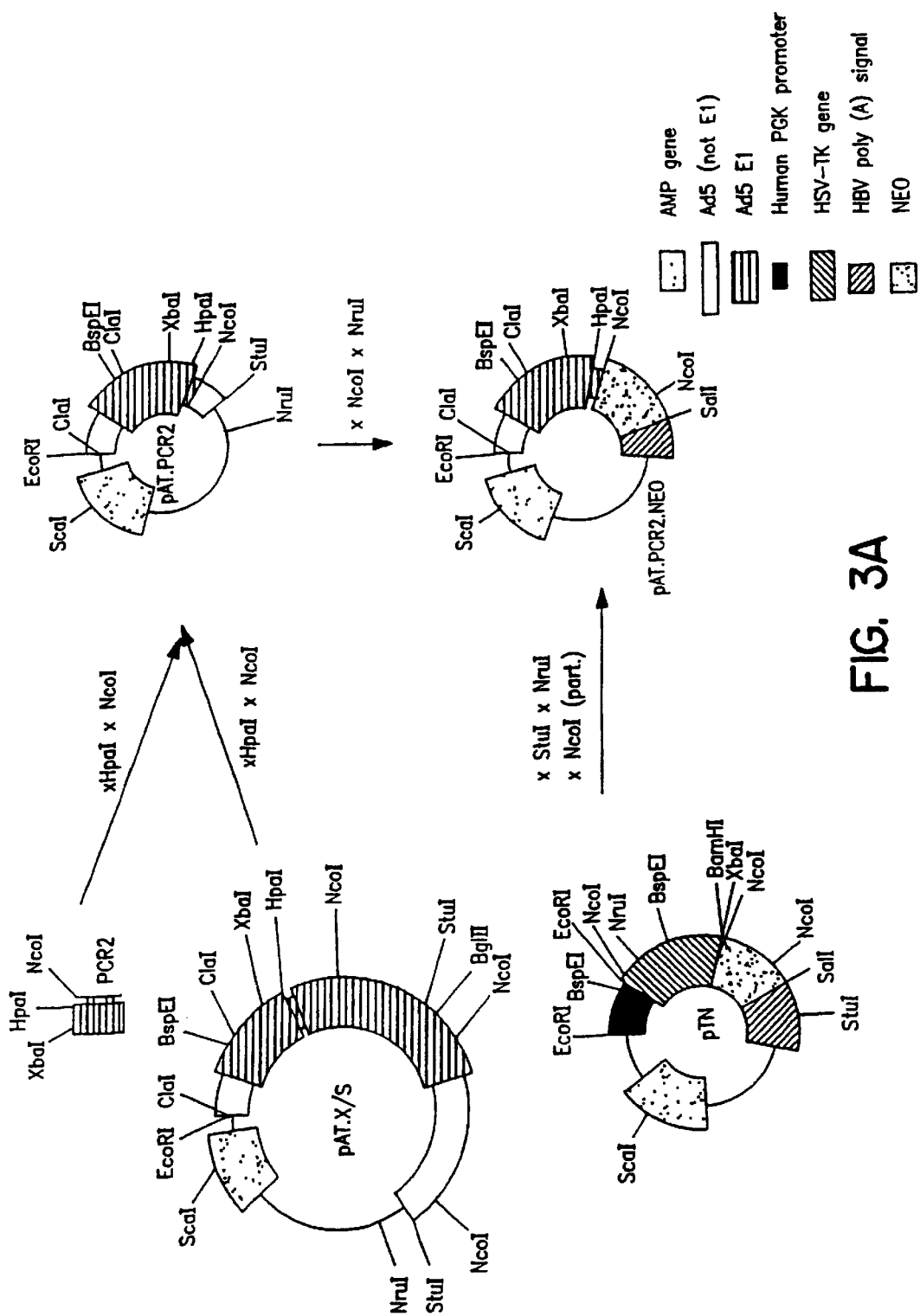
FIGS. 3A and 3B illustrate the construction of pIG.E1A.NEO according to the present invention.
Figure 3B:
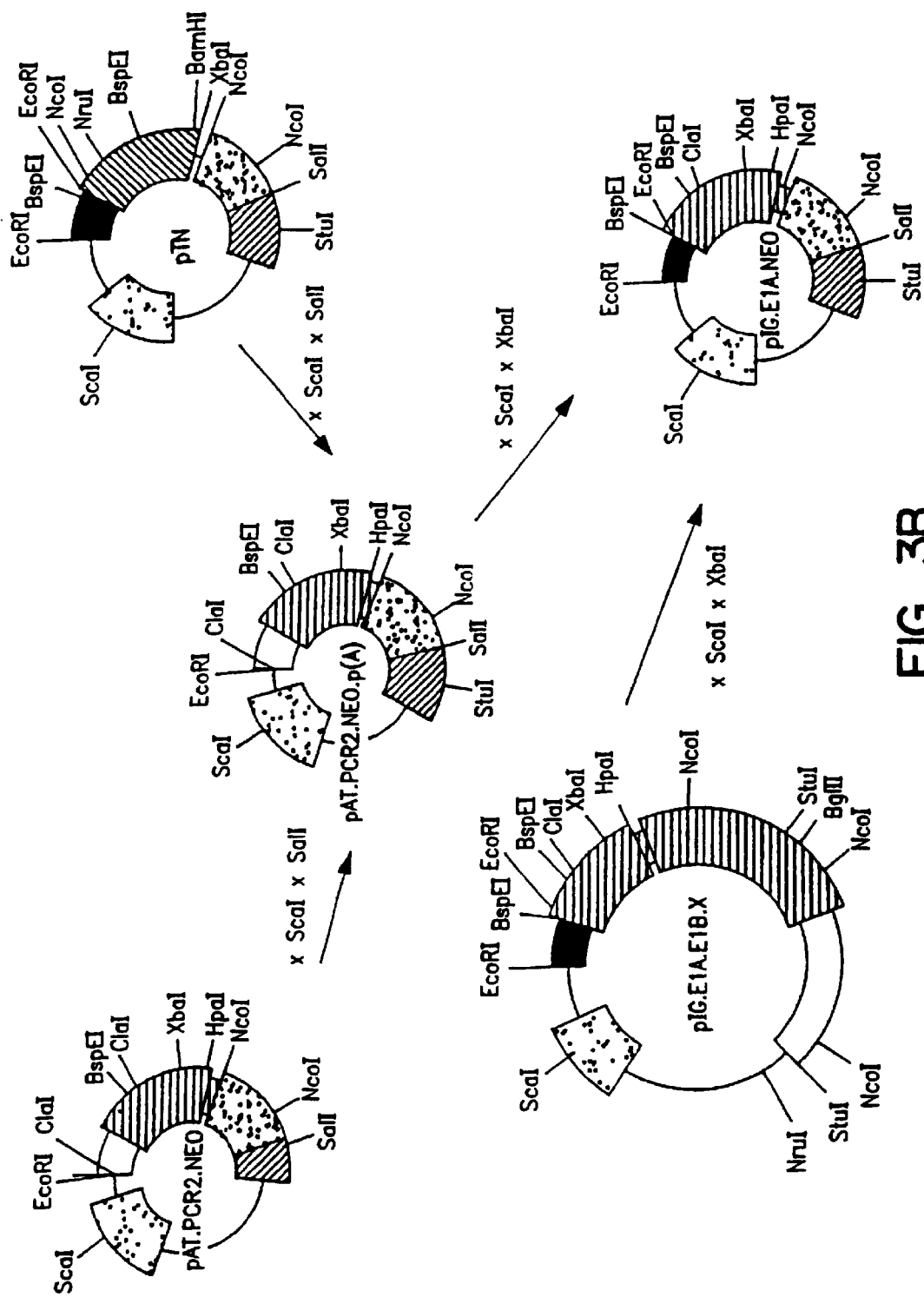

FIGS. 3A and 3B illustrates the construction of pIG.E1A.NEO. In order to introduce the complete E1B promoter and to fuse this promoter in such a way that the AUG codon of E1B 21 kD exactly functions as the AUG codon of NEO$^R$, the E1B promoter was amplified using primers Ea-3 (SEQ ID NO:3) and Ep2 (SEQ ID NO:5), where primer Ep-2 introduces an NcoI site in the PCR fragment. The resulting PCR fragment, named PCRII, was digested with HpaI and NcoI and ligated into pAT-X/S, which was predigested with HpaI and with NcoI. The resulting plasmid was designated pAT-X/S-PCR2. The NcoI-StuI fragment of pTN, containing the NEO gene and part of the Hepatitis B Virus (HBV) poly-adenylation signal, was cloned into pAT-X/S-PCR2 (digested with NcoI and NruI). The resulting construct: pAT-PCR2-NEO. The poly-adenylation signal was completed by replacing the ScaI-SalI fragment of pAT-PCR2-NEO by the corresponding fragment of pTN (resulting in pAT.PCR2.NEO.p(A)). The ScaI-XbaI of pAt.PCR2. NEO.p(A) was replaced by the corresponding fragment of pIG.E1A.E1B-X, containing the PGK promoter linked to E1A genes.

The resulting construct was named pIG.E1A.NEO, and thus contains Ad5 E1 sequences (nt. 459 to nt. 1713) under the control of the human PGK promoter.

Figure 4:
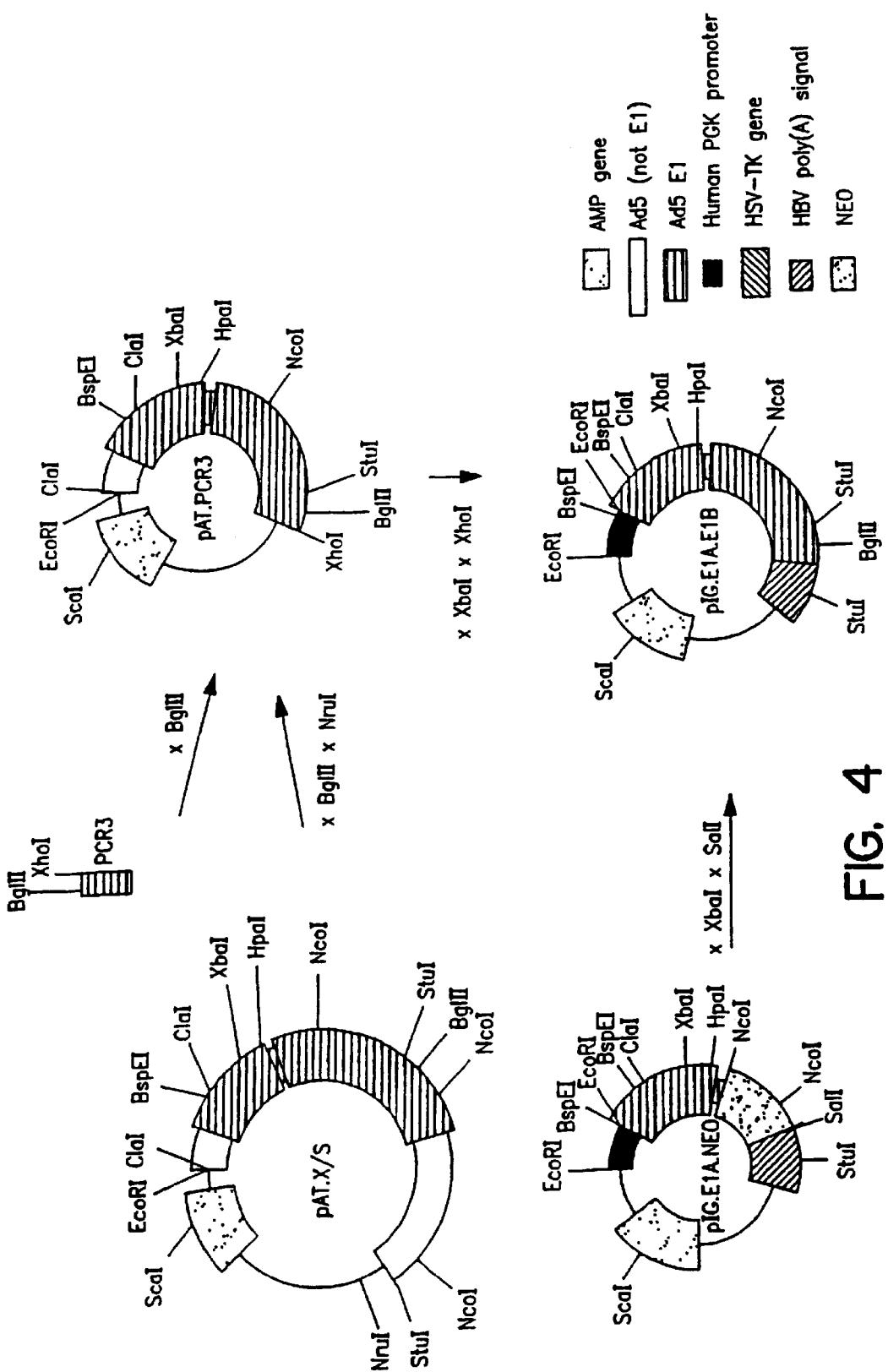
FIG. 4 illustrates the construction of pIG.E1A.E1B according to the present invention.

FIG. 4 illustrates the construction of pIG.E1A.E1B, which was made by amplifying the sequences encoding the N-terminal amino acids of E1B 55 kD using primers Eb-1 (SEQ ID NO:6) and Eb-2 (SEQ ID NO:7) (introduces a XhoI site). The resulting PCR fragment was digested with BglII and cloned into BglII/NruI of pAT-X/S, thereby obtaining pAT-PCR3.

pIG.E1A.E1B was constructed by introducing the HBV poly(A) sequences of pIG.E1A.NEO downstream of E1B sequences of pAT-PCR3 by exchange of XbaI-SalI fragment of pIg.E1A.NEO and the XbaI XhoI fragment of pAT.PCR3.

pIG.E1A.E1B contains nt. 459 to nt. 3510 of Ad5, that encode the E1A and E1B proteins. The E1B sequences are terminated at the splice acceptor at nt. 3511. No pIX sequences are present in this construct.

Figure 5:
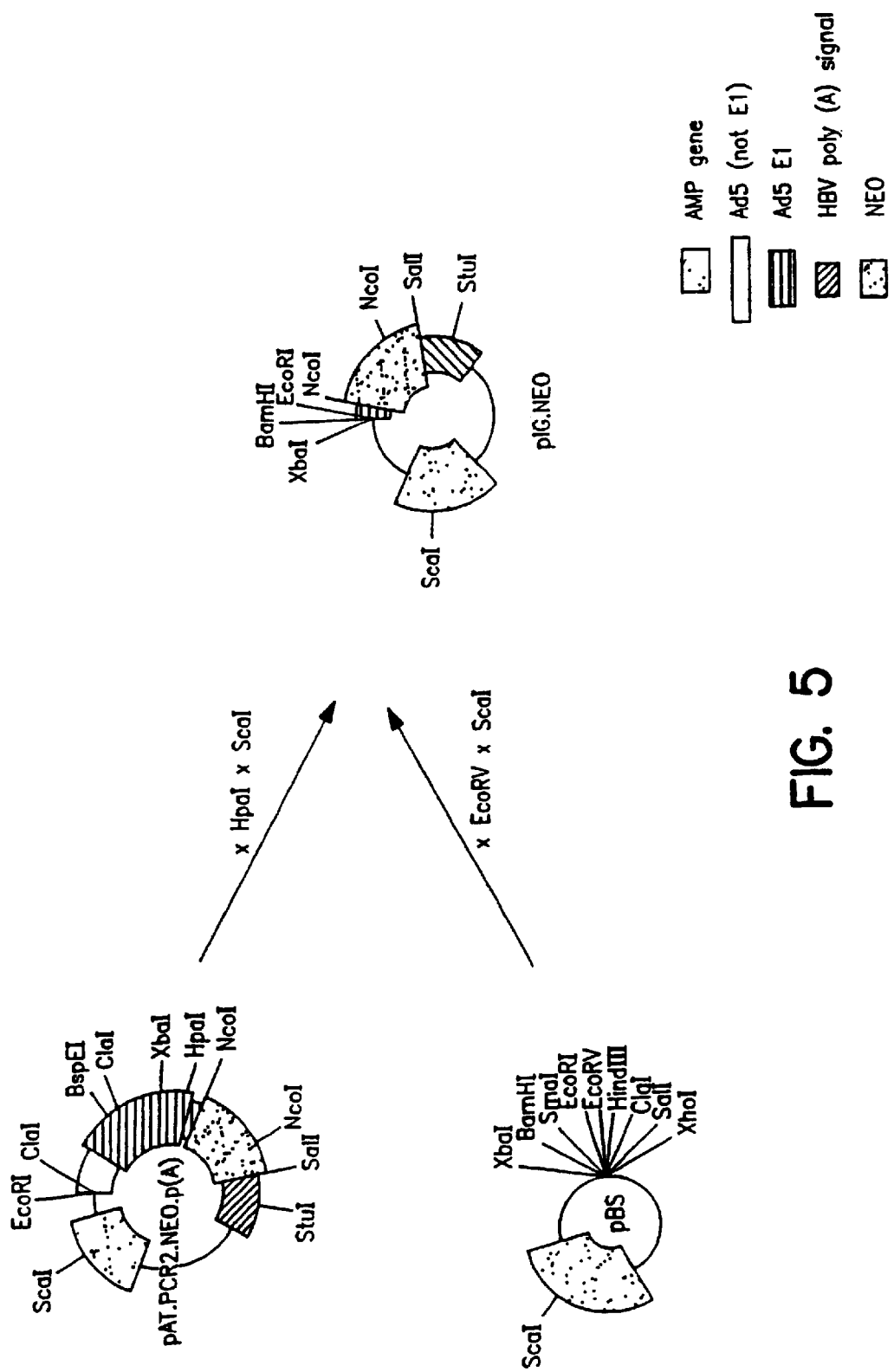
FIG. 5 illustrates the construction of pIG.NEO according to the present invention.

FIG. 5 illustrates the construction of pIG.NEO, which was generated by cloning the HpaI-ScaI fragment of pIG.E1A.NEO, containing the NEO gene under the control of the Ad.5 E1B promoter, into pBS digested with EcoRV and ScaI.

This construct is of use when established cells are transfected with E1A.E1B constructs and NEO selection is required. Because NEO expression is directed by the E1B promoter, NEO resistant cells are expected to co-express E1A, which also is advantageous for maintaining high levels of expression of E1A during long-term culture of the cells.

The integrity of the constructs pIG.E1A.NEO, pIG.E1A.E1B.X and pIG.E1A.E1B was assessed by restriction enzyme mapping; furthermore, parts of the constructs that were obtained by PCR analysis were confirmed by sequence analysis. No changes in the nucleotide sequence were found.

The constructs were transfected into primary BRK (Baby Rat Kidney) cells and tested for their ability to immortalize (pIG.E1A.NEC) or fully transform (pAd5.XhoIC, pIG.E1A.E1B.X and pIG.E1A.E1B) these cells.

Kidneys of 6-day old WAG-Rij rats were isolated, homogenized and trypsinized. Subconfluent dishes (diameter 5 cm) of the BRK cell cultures were transfected with 1 or 5 μg of pIG.NEO, pIG.E1A.NEO, pIG.E1A.E1B, pIG.E1A.E1B.X, pAd5XhoIC, or with pIG.E1A.NEO together with PDC26 (see Van der Elsen et al., "Expression of Region E1B of Human Adenoviruses in the Absence of Region E1A is not Sufficient for Complete Transformation", Virology 128, pp. 377–390 (1983), hereby incorporated herein by reference), carrying the Ad5.E1B gene under control of the SV40 early promoter. After three weeks post-transfection, when foci were visible, the dishes were fixed, Giemsa stained, and the foci counted.

Figure 6:
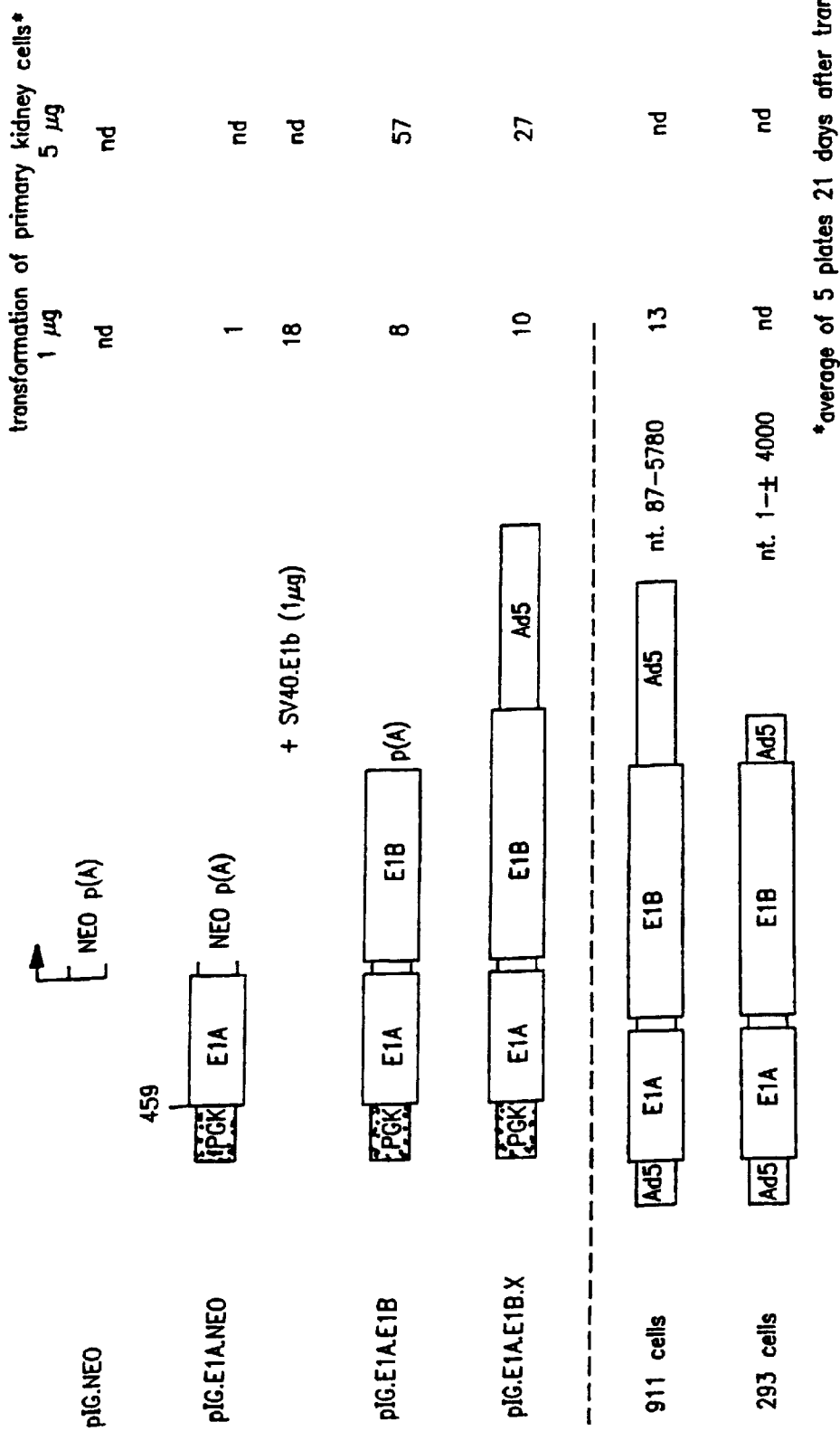
FIG. 6 illustrates the transformation of primary baby rat kidney (BRK) cells by adenovirus packaging constructs according to the present invention.

An overview of the generated adenovirus packaging constructs, and their ability to transform BRK, is presented in FIG. 6. The results indicate that the constructs pIG.E1A.E1B and pIG.E1A.E1B.X are able to transform BRK cells in a dose-dependent manner. The efficiency of transformation is similar for both constructs and is comparable to what was found with the construct that was used to make 911 cells, namely pAd5XhoIC.

As expected, pIG.E1A.NEO was hardly able to immortalize BRK. However, co-transfection of an E1B expression construct (PDC26) did result in a significant increase of the number of transformants (18 versus 1), indicating that E1A encoded by pIG.E1A.NEO is functional. Therefore, the newly generated packaging constructs are suited for the generation of new adenovirus packaging lines.

Human A549 bronchial carcinoma cells (see Shapiro et al., "Phospholipid Biosynthesis and Secretion by a Cell Line (A549) Which Resembles Type II Alveolar Epithelial Cells", Biochem. Biophys. Acta 530, pp. 197–207 (1978), hereby incorporated herein by reference), human embryonic retinoblasts (HER), Ad5-E1-transformed human embryonic kidney (HEK) cells, (293) (see the Graham article) cells and Ad5-transformed HER cells (911; see the Fallaux 1996 article)) and PER cells were grown in Dulbecco's Modified Eagle Medium (DMEM) supplemented with 10% Fetal Calf Serum (FCS) and antibiotics in a 5% $CO_2$ atmosphere at 37° C. Cell culture media, reagents and sera were purchased from Gibco Laboratories (Grand Island, N.Y.). Culture plastics were purchased from Greiner (Nürtingen, Germany) and Corning (Corning, N.Y.).

The construction of adenoviral vectors IG.Ad.MLP.nls.lacZ, IG.Ad.MLP.luc, IG.Ad.MLP.TK and IG.Ad.CMV.TK is described in detail in patent application EP 95202213. The recombinant adenoviral vector IG.Ad-.MLP.nls.lacZ contains the E. coli lacZ gene, encoding β-galactosidase, under control of the Ad2 major late promoter (MLP).IG.Ad.MLP.luc and contains the firefly luciferase gene driven by the Ad2 MLP. Adenoviral vectors IG.Ad.MLP.TK and IG.Ad.CMV.TR contain the Herpes Simplex Virus thymidine kinase (TK) gene under the control of the Ad2 MLP and the Cytomegalovirus (CMV) enhancer/promoter, respectively.

All transfections were performed by calcium-phosphate precipitation DNA (see Graham, F. L., and van der Eb, A. J., "A New Technique for the Assay of Infectivity of Human Adenovirus 5 DNA", Virology 52, pp. 456–467 (1973), hereby incorporated herein by reference) with the GIBCO Calcium Phosphate Transfection System (GIBCO BRL Life Technologies Inc., Gaithersburg, Md., USA), according to the manufacturer's protocol.

Subconfluent cultures of exponentially growing 293,911 and Ad5-E1-transformed A549 and PER cells were washed with PBS and scraped in Fos-RIPA buffer (10 mM Tris (pH 7.5), 150 mM NaCl, 1% NP40 (a detergent available from Sigma, St. Louis, Mo., USA), 0.1% sodium dodecyl sulphate (SDS), 1% NA-DOC, 0.5 mM phenyl methyl sulphonyl fluoride ("PMSF"), 0.5 mM trypsin inhibitor, 50 mM NaF and 1 mM sodium vanadate). After 10 minutes at room temperature, lysates were cleared by certification. Protein concentrations were measured with the Biorad protein assay kit, and 25 µg total cellular protein was loaded on a 12.5% SDS-PAA gel. After electrophoresis, proteins were transferred to nitrocellulose (1 h at 300 mA). Prestained standards (Sigma, USA) were run in parallel. Filters were blocked with 1% bovine serum albumin (BSA) in TBST (10 mM Tris, pH 8, 15 mM NaCl, and 0.05% Tween-20) for 1 hour. The first antibodies were the mouse monoclonal anti-Ad5-E1B-55-kD antibody A1C6, and the rat monoclonal anti-Ad5-E1B-221-kD antibody C1G11 (see Zantema et al., "Localization of the E1B Proteins of Adenovirus 5 in Transformed Cells, as Revealed by Interaction with Monoclonal Antibodies", *Virology* 142, pp. 44–58 (1985), hereby incorporated herein by reference). The second antibody was a horseradish peroxidase-labeled goat anti-mouse antibody (Promega). Signals were visualized by enhanced chemoluminescence (Amersham Corp, UK).

High molecular weight DNA was isolated and 10 µg was digested to completion and fractionated on a 0.7% agarose gel. Southern blot transfer to Hybond N+ (Amersham, UK) was performed with a 0.4 M NaOH, 0.6 M NaCl transfer solution (see G. M. Church and W. Gilbert, "Genomic Sequencing", Proc. Nat'l. Acad. Sci., USA, 81(7), pp. 1991–1995(1984)). Hybridization was performed with a 2463-nt SspI-HindIII fragment from pAd5.SalB (see Bernards et al., "Role of Adenovirus Types 5 and 12 Early Region 1b Tumor Antigens in Oncogenic Transformation", *Virology* 127, pp. 45–53 (1983), hereby incorporated herein by reference). This fragment consists of Ad5 bp. 342–2805. The fragment was radiolabeled with $\alpha$-$^{32}$P-dCTP with the use of random hexanucleotide primers and Klenow DNA polymerase. The southern blots were exposed to a Kodak XAR-5 film at about −80° C. and to a Phospho-Imager screen which was analyzed by B&L systems Molecular Dynamics software.

Ad5-E1-transformed A549 human bronchial carcinoma cell lines were generated by transfection with pIG.E1A.NEO and selection for G418 resistance. Thirty-one G418-resistant clones were established. Co-transfection of pIG.E1A.E1B with pIG.NEO yielded seven G418-resistant cell lines.

Ad5-E1-transformed human embryonic retina (HER) cells were generated by transfection of primary HER cells with plasmid pIG.E1A.E1B. The transformed cell lines were established from well-separated foci. We were able to establish seven clonal cell lines which we called PER.C1, PER.C3, PER.C4, PER.C5, PER.C6™, PER.C8 and PER.C9.

Expression of the Ad5 E1A and the 55-kD and 21 kD E1B proteins in the established A549 and PER cells was studied by means of Western blotting with the use of monoclonal antibodies (mAb). Mab M73 recognizes the E1A products, whereas Mabls AIC6 and C1G11 are directed against the 55 kD and 21 kD E1B proteins, respectively.

Figure 7:
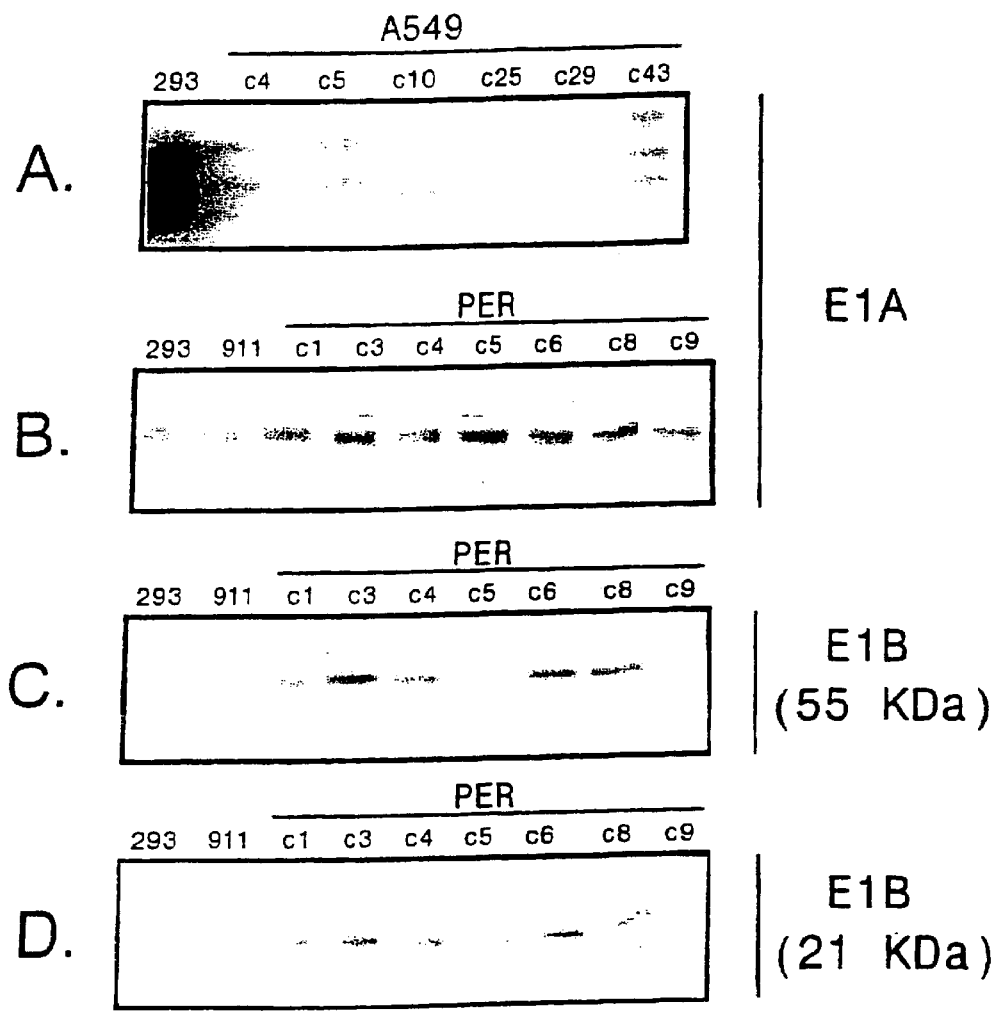
FIG. 7 illustrates a Western blot analysis of A549 clones transfected with pIG.E1A.NEO and human embryonic retinoblasts (HER cells) transfected with pIG.E1A.E1B (PER clones) according to the present invention.

The antibodies did not recognize proteins in extracts from the parental A549 or the primary HER cells (data not shown). None of the A549 clones that were generated by co-transfection of pIG.NEO and pIG.E1A.E1B expressed detectable levels of E1A or E1B proteins (not shown). Some of the A549 clones that were generated by transfection with pIG.E1A.NEO expressed the Ad5 E1A proteins (see FIG. 7), but the levels were much lower than those detected in protein lysates from 293 cells. The steady state E1A levels detected in protein extracts from PER cells were much higher than those detected in extracts from A549-derived cells. All PER cell lines expressed similar levels of E1A proteins (see FIG. 7). The expression of the E1B proteins, particularly in the case of E1B 55 kD, was mote variable. Compared to 911 and 293, the majority of the PER clones express high levels of E1B 55 kD and 21 kD. The steady state level of E1B 21 kD was the highest in PER.C3. None of the PER clones lost expression of the Ad5 E1 genes upon serial passage of the cells (not shown). We found that the level of E1 expression in PER cells remained stable for at least 100 population doublings.

Figure 8:
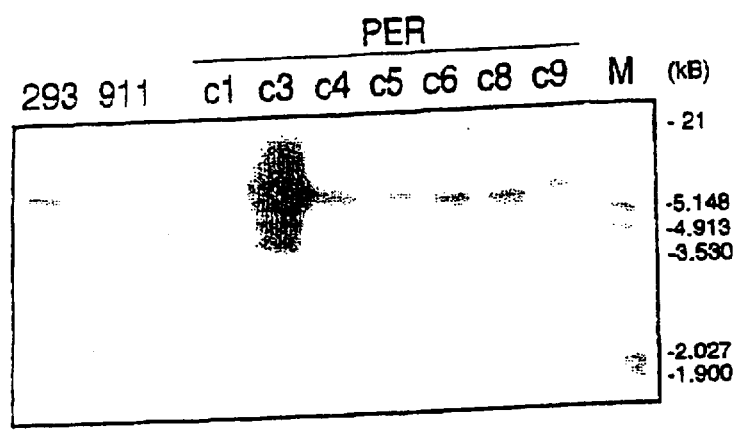
FIG. 8 illustrates a Southern blot analysis of 293, 911 and PER cell lines. Cellular DNA was extracted, Hind III digested, electrophoresed and transferred to Hybond N+ membranes (Amersham) according to the present invention.

To study the arrangement of the Ad5-E1 encoding sequences in the PER clones, Southern analyses were performed. Cellular DNA was extracted from all PER clones, and from 293 and 911 cells. The DNA was digested with HindIII, which cuts once in the Ad5 E1 region. Southern hybridization on HindIII-digested DNA using a radiolabeled Ad5-E1-specific probe revealed the presence of several integrated copies of pIG.E1A.E1B in the genome of the PER clones. FIG. 8 shows the distribution pattern of E1 sequences in the high molecular weight DNA of the different PER cell lines. The copies are concentrated in a single band, which suggests that they are integrated as tandem repeats. In the case of PER.C3, PER.C5, PER.C6™ and PER.C9, we found additional hybridizing bands of low molecular weight that indicate the presence of truncated copies of pIG.E1A.E1B. The number of copies was determined with the use of a Phospho-Imager. We estimated that PER.C1, PER.C3, PER.C4, PER.C5, PER.C6™, PER.C8 and PER.C9 contains 2, 88, 5, 4, 5, 5 and 3 copies of the Ad5 E1 coding region, respectively, and that 911 and 293 cells contains 1 and 4 copies of the Ad5 E1 sequences, respectively.

Figure 9:
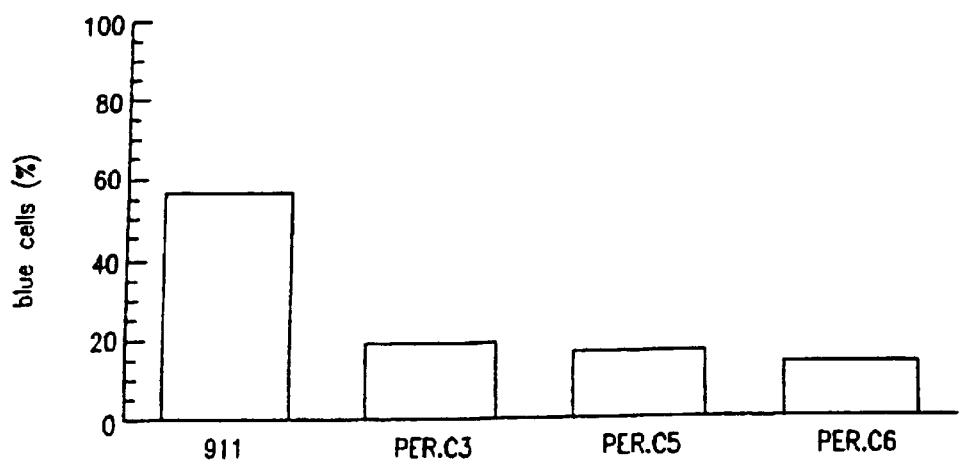
FIG. 9 illustrates the transfection efficiency of PER.C3, PER.C5, PER.C6™ and 911 cells according to the present invention.

Recombinant adenovectors are generated by co-transfection of adaptor plasmids and the large ClaI fragment of Ad5 into 293 cells (see, EPO patent application EP 95202213). The recombinant virus DNA is formed by homologous recombination between the homologous viral sequences that are present in the plasmid and the adenovirus DNA. The efficacy of this method, as well as that of alternative strategies, is highly dependent on the transfectability of the helper cells. Therefore, we compared the transfection efficiencies of some of the PER clones with 911 cells, using the *E. coli* β-galactosidase-encoding lacZ gene as a reporter (see FIG. 9). With regard to FIG. 9, the transfection efficiency of PER.C3, PER.C5, PER.C6™, and 911 cells is illustrated. Cells were cultured in 6-well plates and transfected (n=2) with 5 µg pRSV.lacZ by calcium-phosphate co-precipitation. Forty-eight hours later, the cells were stained with X-GAL. The mean percentage of blue cells is graphed in FIG. 9.

Table 4 details yields of different recombinant adenovirus obtained after inoculation of adenovirus E1 packaging cell lines 293, 911, PER.C3, PER.C5 and PER.C6™ with different adenovirus vectors. The yields are the mean of two different experiments.

The results indicate that the yields obtained on PER cells are at least as high as those obtained on the existing cell lines. In addition, the yields of the novel adenovirus vector IG.Ad.MLPI.TK are similar or higher than the yields obtained for the other viral vectors on all cell lines tested.

It is noted that IG.Ad.CMV.lacZ and IG.Ad.CMV.TK are described in patent application EP 95202213, that the construction of IG.Ad.MLPI.TK is described in this patent application, and that the yields of virus per T80 flask were determined by plaque assay on 911 cells, as described in the Fallaux 1996 article.

TABLE 4

| Cell | Passage number | IG.Ad.CMV. lacZ | IG.Ad. CM V.TK | IG.Ad. MLP I.TK | d1313 | Producer Mean |
|---|---|---|---|---|---|---|
| 293 |  | 6.0 | 5.8 | 24 | 34 | 17.5 |
| 911 |  | 8 | 14 | 34 | 180 | 59.5 |
| PER.C3 | 17 | 8 | 11 | 44 | 40 | 25.8 |
| PER.C5 | 15 | 6 | 17 | 36 | 200 | 64.7 |
| PER.C6 | 36 | 10 | 22 | 58 | 320 | 102 |

Yields × $10^{-8}$ pfu/T175 flask.

Figure 10:
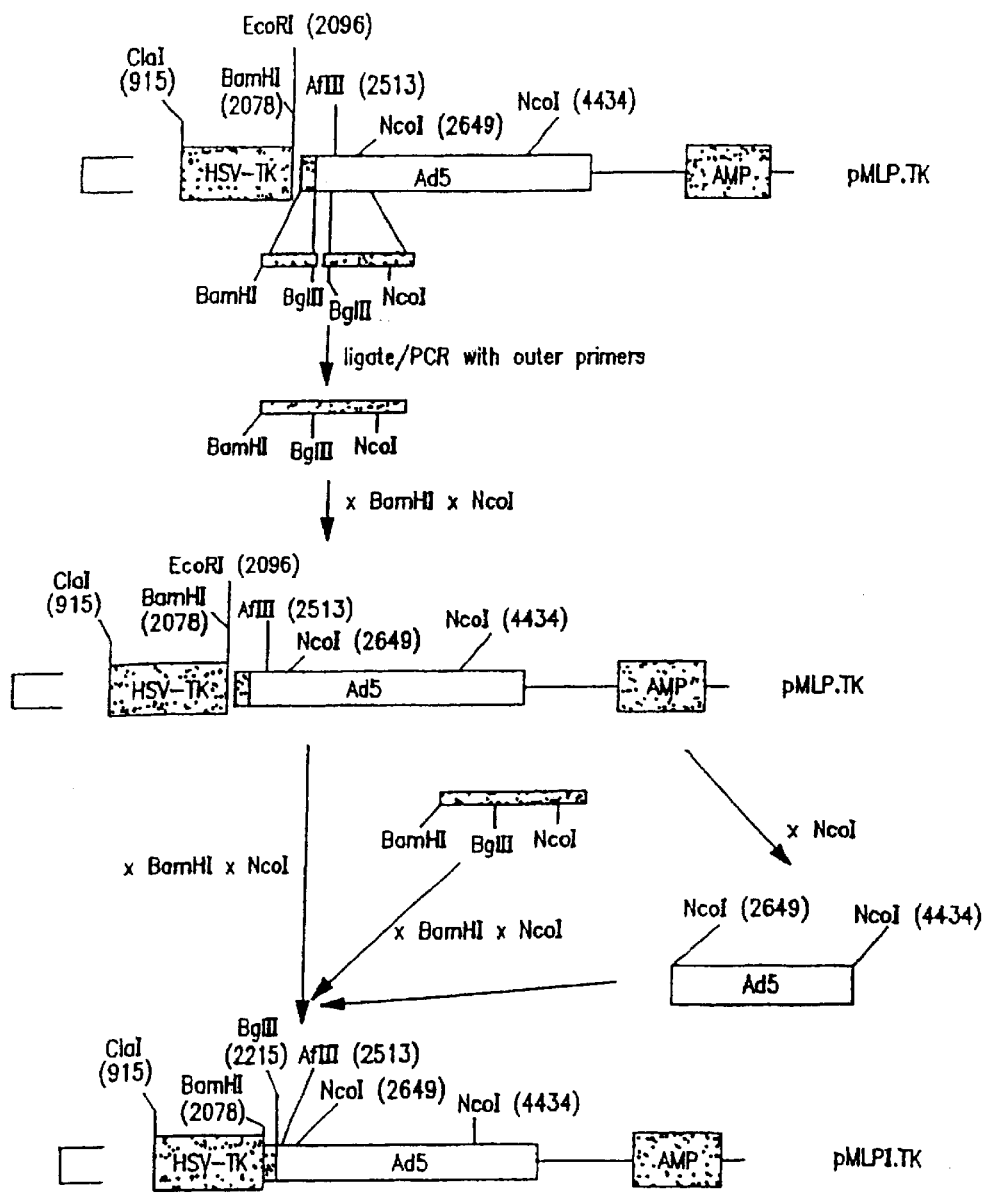
FIG. 10 illustrates construction of adenovirus vector, pMLPI.TK. pMLPI.TK is designed to have no sequence overlap with the packaging construct pIG.E1A.E1B according to the present invention.

The generation of new adenovirus vectors pMLPI.TK are illustrated in FIG. 10. The used recombinant adenovirus vectors (see patent application EP 95202213) are deleted for E1 sequences from nt. 459 to nt. 3328. As construct pE1A.E1B contains Ad5 sequences nt. 459 to nt. 3510, there is a sequence overlap of 183 nt. between E1B sequences in the packaging construct pIG.E1A.E1B and recombinant adenoviruses, such as IG.Ad.MLP.TK. The overlapping sequences were deleted from the new adenovirus vectors. In addition, non-coding sequences derived from lacZ that are present in the original constructs, were deleted as well. This was achieved (see FIG. 10) by PCR amplification of the SV40 poly(A) sequences from pMLP.TK using primers SV40-1 (SEQ ID NO:8) (introduces a BamHI site) and SV40-2 (SEQ ID NO:9) (introduces a BglII site). In addition, Ad5 sequences present in this construct were amplified from nt. 2496 (Ad5-1 (SEQ ID NO:10), introduces a BglII site) to nt. 2779 (Ad5-2 (SEQ ID NO:11)). Both PCR fragments were digested with BglII and were ligated. The ligation product was PCR amplified using primers SV40-1 and Ad5-2. The PCR product obtained was cut with BamHI and AflII and was ligated into pMLP.TK predigested with the same enzymes. The resulting construct, named pMLPI.TK, contains a deletion in adenovirus E1 sequences from nt. 459 to nt. 3510.

The combination of the new packaging construct pIG.E1A.E1B and the recombinant adenovirus pMLPI.TK, which do not have any sequence overlap, are presented in FIGS. 11A and 11B. In FIGS. 11A and 11B, the original situation is also presented, wherein the sequence overlap is indicated. The absence of overlapping sequences between pIG.E1A.E1B and pMLPI.TK (see FIG. 11a) excludes the possibility of homologous recombination between packaging construct and recombinant virus, and is, therefore, a significant improvement for production of recombinant adenovirus as compared to the original situation.

FIG. 11b depicts the situation for pIG.E1A.NEO and IG.Ad.MLPI.TK. pIG.E1A.NEO, when transfected into established cells, is expected to be sufficient to support propagation of E1-deleted recombinant adenovirus. This combination does not have any sequence overlap, thus preventing generation of RCA by homologous recombination. In addition, this convenient packaging system allows the propagation of recombinant adenoviruses that are deleted just for E1A sequences and not for E1B sequences. Recombinant adenoviruses expressing E1B in the absence of E1A are attractive, because the E1B protein, in particular E1B 19 kD, is able to prevent infected human cells from lysis by Tumor Necrosis Factor (TNF) (see Gooding, et al., "The E1B 19,000-molecular-weight Protein of Group C Adenoviruses Prevents Tumor Necrosis Factor Cytolysis of Human Cells but Not of Mouse Cells", J. Virol. 65, pp. 3083–3094 (1991), hereby incorporated herein by reference).

Figure 12:
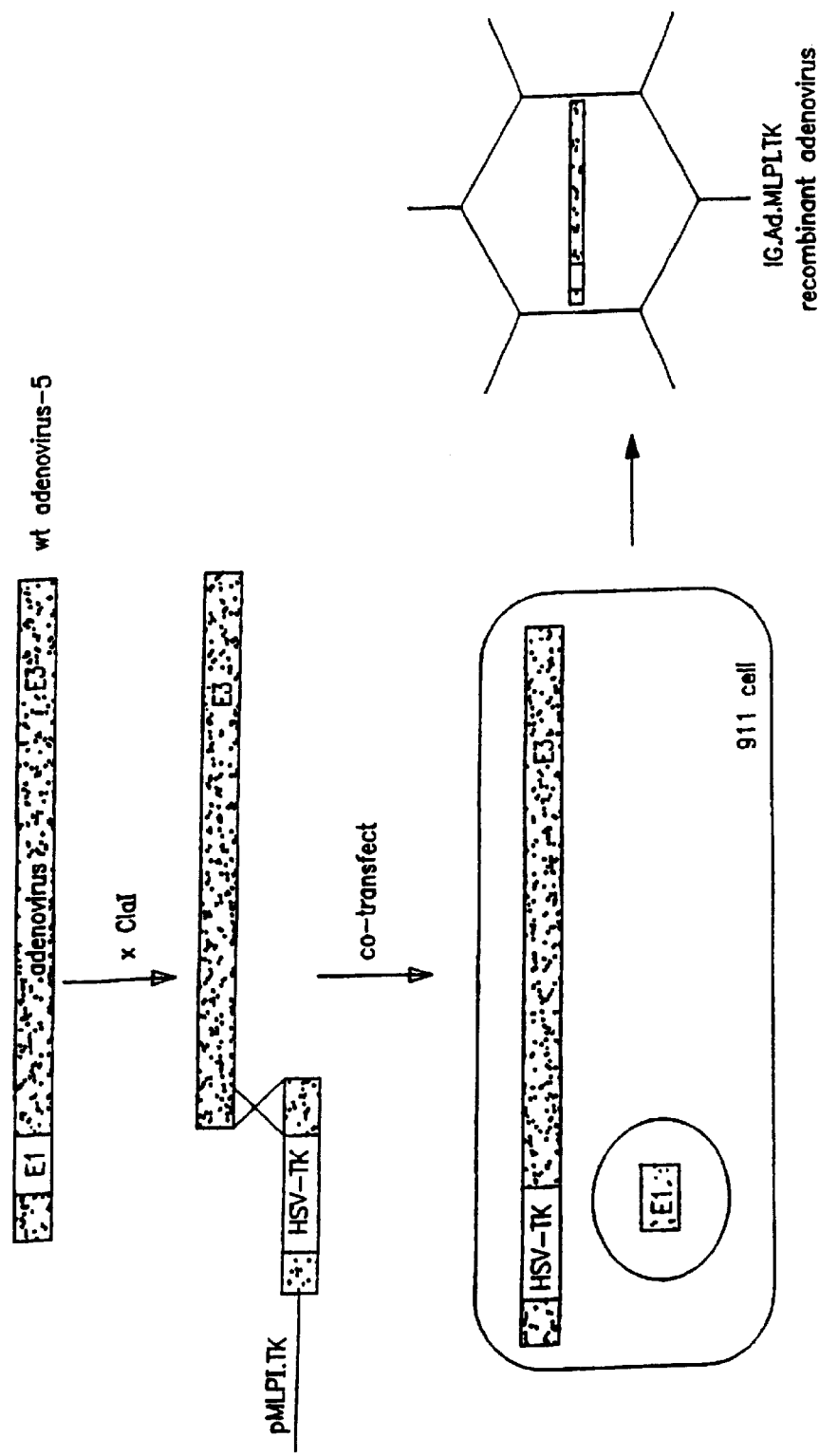
FIG. 12 illustrates the generation of recombinant adenovirus, IG.Ad.MLPI.TK according to the present invention.

Recombinant adenovirus was generated by co-transfection of 293 cells with SalI linearized pMLPI.TK DNA and ClaI linearized Ad5 wt DNA. The procedure is schematically represented in FIG. 12.

The following name convention of the plasmids used will be utilized in the following outline of the strategy to generate packaging systems for minimal adenovirus vector.

p plasmid
I ITR (Adenovirus Inverted Terminal Repeat)
C Cytomegalovirus (CMV) Enhancer/Promoter Combination
L Firefly Luciferase Coding Sequence hac,haw-Potential hairpin that can be formed after digestion with restriction endonuclease Asp718 in its correct and in the reverse orientation, respectively (see FIG. 15 (SEQ ID NO: 22)).

For example, pICLhaw is a plasmid that contains the adenovirus ITR followed by the CMV-driven luciferase gene and the Asp718 hairpin in the reverse (non-functional) orientation.

With regard to FIG. 15, a potential hairpin conformation of a single stranded DNA molecule that contains the HP/asp sequences used in these studies is shown. Restriction with the restriction endonuclease Asp718I of plasmid pICLhac, containing the annealed oligonucleotide pair HP/asp1 and HP/asp2 will yield a linear double-stranded DNA fragment. In cells in which the required adenovirus genes are present, replication can initiate at the terminus that contains the ITR sequence. During the chain elongation, one of the strands will be displaced. The terminus of the single-stranded, displaced-strand molecule can adopt the conformation depicted in FIG. 15. In this conformation, the free 3'-terminus can serve as a primer for the cellular and/or adenovirus DNA polymerase, resulting in conversion of the displaced strand in the double-stranded form.

EXPERIMENT 1

The competence of a synthetic DNA sequence that is capable of forming a hairpin-structure, to serve as a primer for reverse strand synthesis for the generation of double-stranded DNA molecules in cells that contain and express adenovirus genes was demonstrated, as follows. Plasmids pICLhac, pICLhaw, pICLI and pICL were generated using standard techniques. The schematic representation of these plasmids is shown in FIGS. 16–19.

Plasmid pICL is derived from the following plasmids:

nt. 1–457 pMLP10 (see the Levrero article)
nt. 458–1218 pCMVβ (Clontech, EMBL Bank No. U02451)
nt. 1219–3016 pMLP.luc (IntroGene, unpublished)
nt. 3017–5620 pBLCAT5 (see Stein, R. W., and Whelan, J., "Insulin Gene Enhancer Activity is Inhibited by Adenovirus 5 E1A Gene Products", Mol. Cell. Biol. 9, pp. 4531–4534 (1989), hereby incorporated herein by reference).

Figure 19:
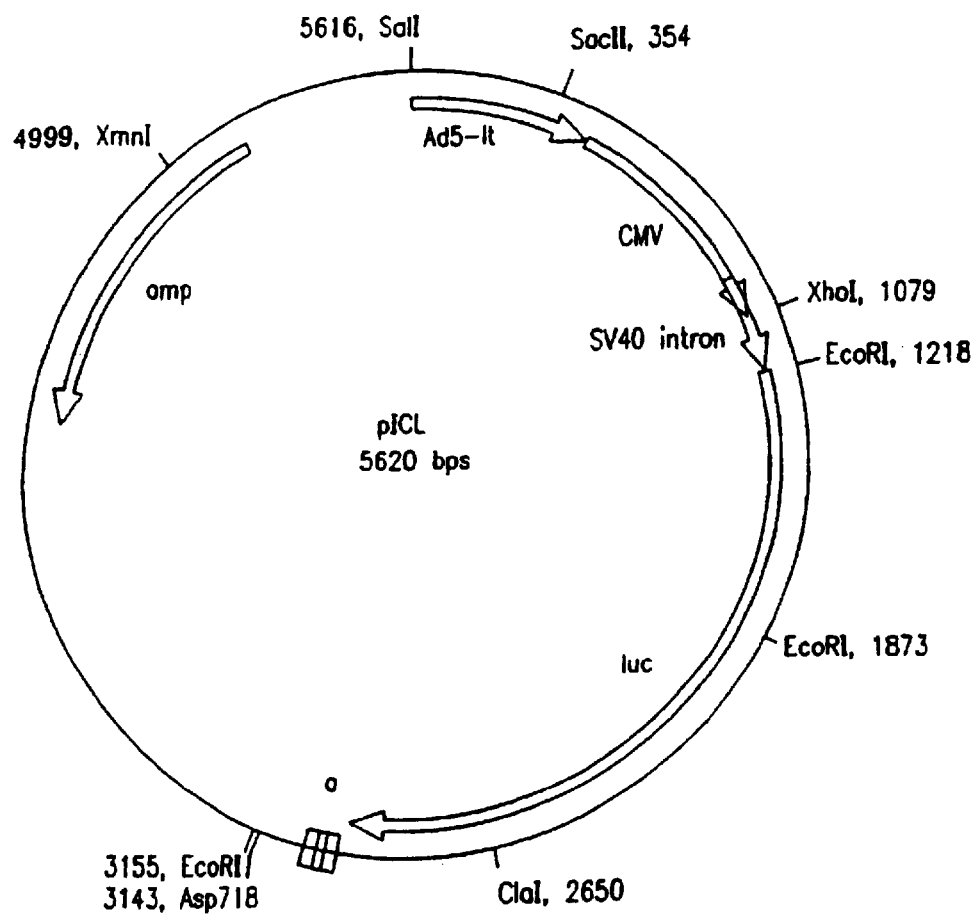
FIG. 19 is a diagram of pICL according to the present invention.

The plasmid was constructed by the method which follows. The tet gene of plasmid pMLP10 has been inactivated by deletion of the BamHI-SalI fragment, to generate pMLP10ΔSB. Using primer set PCR/MLP1 (SEQ ID NO:14) and PCR/MLP3 (SEQ ID NO:16) a 210 bp fragment containing the Ad5-ITR, flanked by a synthetic SalI restriction site, was amplified using pMLP10 DNA as the template. The PCR product was digested with the enzymes EcoRI and SgrAI to generate a 196 bp. fragment. Plasmid pMLP10ΔSB was digested with EcoRI and SgrAI to remove the ITR. This fragment was replaced by the EcoRI-SgrAI-treated PCR fragment to generate pMLP/SAL. Plasmid pCMV-Luc was digested with PvuII to completion and recirculated to remove the SV40-derived poly-adenylation signal and Ad5 sequences with exception of the Ad5 left-terminus. In the resulting plasmid, pCMV-lucΔAd, the Ad5 ITR was replaced by the Sal-site-flanked ITR from plasmid pMLP/SAL by exchanging the XmnI-SacII fragments. The resulting plasmid, pCMV-lucΔAd/SAL, the Ad5 left terminus and the CMV-driven luciferase gene were isolated as an SalI-SmaI fragment and inserted in the SalI and HpaI digested plasmid pBLCATS, to form plasmid pICL. Plasmid pICL is represented in FIG. 19 and its sequence (SEQ ID NO:21) is presented below.

The plasmid pICL contains the following features:

| | |
|---|---|
| nt. 1–457 | Ad5 left terminus (Sequence 1–457 of human adenovirus type 5) |
| nt. 458–969 | Human cytomegalovirus enhancer and immediate early promoter (see Boshart et al., A Very Strong Enhancer is Located Upstream of an Immediate Early Gene of Human Cytomegalovirus", Cell 41, pp. 521–530 (1985), hereby incorporated herein by reference) (from plasmid pCMVβ, Clontech, Palo Alto, USA) |
| nt. 970–1204 | SV40 19S exon and truncated 16/19S intron (from plasmid pCMVβ) |
| nt. 1218–2987 | Firefly luciferase gene (from pMLP.luc) |
| nt. 3018–3131 | SV40 tandem poly-adenylation signals from late transcript, derived from plasmid pBLCAT5) |
| nt. 3132–5620 | pUC12 backbone (derived from plasmid pBLCAT5) |
| nt. 4337–5191 | β-lactamase gene (Amp-resistence gene, reverse orientation) |

```
NAME:         pICL 5620 BPS DNA CIRCULAR UPDATED May 01, 1995
DESCRIPTION:  1 x Ad5-ITR, CMV-luciferase, minimal vector
SEQUENCE:     sequence based on the available information;
              Constructions verified by restriction enzyme
              digests; Sequence of regions derived from amplified
              DNA verified by sequence analyses
```

SEQUENCE

```
   1 CATCATCAAT AATATACCTT ATTTTGGATT GAAGCCAATA TGATAATGAG GGGGTGGAGT
  61 TTGTGACGTG GCGCGGGGCG TGGGAACGGG GCGGGTGACG TAGTAGTGTG GCGGAAGTGT
 121 GATGTTGCAA GTGTGGCGGA ACACATGTAA GCGACGGATG TGGCAAAAGT GACGTTTTTG
 181 GTGTGCGCCG GTGTACACAG GAAGTGACAA TTTTCGCGCG GTTTTAGGCG GATCTTGTAG
 241 TAAATTTGGG CGTAACCGAG TAAGATTTGG CCATTTTCGC GGGAAAACTG AATAAGAGGA
 301 AGTGAAATCT GAATAATTTT GTGTTACTCA TAGCGCGTAA TATTTGTCTA GGGCCGCGGG
 361 GACTTTGACC GTTTACGTGG AGACTCGCCC AGGTGTTTTT CTCAGGTGTT TTCCGCGTTC
 421 CGGGTCAAAG TTGGCGTTTT ATTATTATAG TCAGGGGCTG CAGGTCGTTA CATAACTTAC
 481 GGTAAATGGC CCGCCTGGCT GACCGCCCAA CGACCCCCGC CCATTGACGT CAATAATGAC
 541 GTATGTTCCC ATAGTAACGC CAATAGGGAC TTTCCATTGA CGTCAATGGG TGGAGTATTT
 601 ACGGTAAACT GCCCACTTGG CAGTACATCA AGTGTATCAT ATGCCAAGTA CGCCCCCTAT
 661 TGACGTCAAT GACGGTAAAT GGCCCGCCTG GCATTATGCC CAGTACATGA CCTTATGGGA
 721 CTTTCCTACT TGGCAGTACA TCTACGTATT AGTCATCGCT ATTACCATGG TGATGCGGTT
 781 TTGGCAGTAC ATCAATGGGC GTGGATAGCG GTTTGACTCA CGGGGATTTC CAAGTCTCCA
 841 CCCCATTGAC GTCAATGGGA GTTTGTTTTG GCACCAAAAT CAACGGGACT TTCCAAAATG
 901 TCGTAACAAC TCCGCCCCAT TGACGCAAAT GGGCGGTAGG CGTGTACGGT GGGAGGTCTA
 961 TATAAGCAGA GCTCGTTTAG TGAACCGTCA GATCGCCTGG AGACGCCATC CACGCTGTTT
1021 TGACCTCCAT AGAAGACACC GGGACCGATC CAGCCTCCGG ACTCTAGAGG ATCCGGTACT
1081 CGAGGAACTG AAAAACCAGA AAGTTAACTG GTAAGTTTAG TCTTTTTGTC TTTTATTTCA
1141 GGTCCCGGAT CCGGTGGTGG TGCAAATCAA AGAACTGCTC CTCAGTGGAT GTTGCCTTTA
1201 CTTCTAGTAT CAAGCTTGAA TTCCTTTGTG TTACATTCTT GAATGTCGCT CGCAGTGACA
1261 TTAGCATTCC GGTACTGTTG GTAAAATGGA AGACGCCAAA AACATAAAGA AAGGCCCGGC
1321 GCCATTCTAT CCTCTAGAGG ATGGAACCGC TGGAGAGCAA CTGCATAAGG CTATGAAGAG
1381 ATACGCCCTG GTTCCTGGAA CAATTGCTTT TACAGATGCA CATATCGAGG TGAACATCAC
1441 GTACGCGGAA TACTTCGAAA TGTCCGTTCG GTTGGCAGAA GCTATGAAAC GATATGGGCT
1501 GAATACAAAT CACAGAATCG TCGTATGCAG TGAAAACTCT CTTCAATTCT TTATGCCGGT
1561 GTTGGGCGCG TTATTTATCG GAGTTGCAGT TGCGCCCGCG AACGACATTT ATAATGAACG
1621 TGAATTGCTC AACAGTATGA ACATTTCGCA GCCTACCGTA GTGTTTGTTT CCAAAAGGG
1681 GTTGCAAAAA ATTTTGAACG TGCAAAAAAA ATTACCAATA ATCCAGAAAA TTATTATCAT
1741 GGATTCTAAA ACGGATTACC AGGGATTTCA GTCGATGTAC ACGTTCGTCA CATCTCATCT
1801 ACCTCCCGGT TTTAATGAAT ACGATTTTGT ACCAGAGTCC TTTGATCGTG ACAAAACAAT
1861 TGCACTGATA ATGAATTCCT CTGGATCTAC TGGGTTACCT AAGGGTGTGG CCCTTCCGCA
1921 TAGAACTGCC TGCGTCAGAT TCTCGCATGC CAGAGATCCT ATTTTTGGCA ATCAAATCAT
1981 TCCGGATACT GCGATTTTAA GTGTTGTTCC ATTCCATCAC GGTTTTGGAA TGTTTACTAC
2041 ACTCGGATAT TTGATATGTG GATTTCGAGT CGTCTTAATG TATAGATTTG AAGAAGAGCT
2101 GTTTTTACGA TCCCTTCAGG ATTACAAAAT TCAAAGTGCG TTGCTAGTAC CAACCCTATT
2161 TTCATTCTTC GCCAAAAGCA CTCTGATTGA CAAATACGAT TTATCTAATT TACACGAAAT
2221 TGCTTCTGGG GGCGCACCTC TTTCGAAAGA AGTCGGGGAA GCGGTTGCAA AACGCTTCCA
2281 TCTTCCAGGG ATACGACAAG GATATGGGCT CACTGAGACT ACATCAGCTA TTCTGATTAC
2341 ACCCGAGGGG GATGATAAAC CGGGCGCGGT CGGTAAAGTT GTTCCATTTT TTGAAGCGAA
```

```
-continued
2401 GGTTGTGGAT CTGGATACCG GGAAAACGCT GGGCGTTAAT CAGAGAGGCG AATTATGTGT
2461 CAGAGGACCT ATGATTATGT CCGGTTATGT AAACAATCCG GAAGCGACCA ACGCCTTGAT
2521 TGACAAGGAT GGATGGCTAC ATTCTGGAGA CATAGCTTAC TGGGACGAAG 0ACGAACACTT
2581 CTTCATAGTT GACCGCTTGA AGTCTTTAAT TAAATACAAA GGATATCAGG TGGCCCCCGC
2641 TGAATTGGAA TCGATATTGT TACAACACCC CAACATCTTC GACGCGGGCG TGGCAGGTCT
2701 TCCCGACGAT GACGCCGGTG AACTTCCCGC CGCCGTTGTT GTTTTGGAGC ACGGAAAGAC
2761 GATGACGGAA AAAGAGATCG TGGATTACGT CGCCAGTCAA GTAACAACCG CGAAAAAGTT
2821 GCGCGGAGGA GTTGTGTTTG TGGACGAAGT ACCGAAAGGT CTTACCGGAA AACTCGACGC
2881 AAGAAAAATC AGAGAGATCC TCATAAAGGC CAAGAAGGGC GGAAAGTCCA AATTGTAAAA
2941 TGTAACTGTA TTCAGCGATG ACGAAATTCT TAGCTATTGT AATGGGGGAT CCCCAACTTG
3001 TTTATTGCAG CTTATAATGG TTACAAATAA AGCAATAGCA TCACAAATTT CACAAATAAA
3061 GCATTTTTTT CACTGCATTC TAGTTGTGGT TTGTCCAAAC TCATCAATGT ATCTTATCAT
3121 GTCTGGATCG GATCGATCCC CGGGTACCGA GCTCGAATTC GTAATCATGG TCATAGCTGT
3181 TTCCTGTGTG AAATTGTTAT CCGCTCACAA TTCCACACAA CATACGAGCC GGAAGCATAA
3241 AGTGTAAAGC CTGGGGTGCC TAATGAGTGA GCTAACTCAC ATTAATTGCG TTGCGCTCAC
3301 TGCCCGCTTT CCAGTCGGGA AACCTGTCGT GCCAGCTGCA TTAATGAATC GGCCAACGCG
3361 CGGGGAGAGG CGGTTTGCGT ATTGGGCGCT CTTCCGCTTC CTCGCTCACT GACTCGCTGC
3421 GCTCGGTCGT TCGGCTGCGG CGAGCGGTAT CAGCTCACTC AAAGGCGGTA ATACGGTTAT
3481 CCACAGAATC AGGGGATAAC GCAGGAAAGA ACATGTGAGC AAAAGGCCAG CAAAAGGCCA
3541 GGAACCGTAA AAAGGCCGCG TTGCTGGCGT TTTTCCATAG GCTCCGCCCC CCTGACGAGC
3601 ATCACAAAAA TCGACGCTCA AGTCAGAGGT GGCGAAACCC GACAGGACTA TAAAGATACC
3661 AGGCGTTTCC CCCTGGAAGC TCCCTCGTGC GCTCTCCTGT TCCGACCCTG CCGCTTACCG
3721 GATACCTGTC CGCCTTTCTC CCTTCGGGAA GCGTGGCGCT TTCTCATAGC TCACGCTGTA
3781 GGTATCTCAG TTCGGTGTAG GTCGTTCGCT CCAAGCTGGG CTGTGTGCAC GAACCCCCCG
3841 TTCAGCCCGA CCGCTGCGCC TTATCCGGTA ACTATCGTCT TGAGTCCAAC CCGGTAAGAC
3901 ACGACTTATC GCCACTGGCA GCAGCCACTG GTAACAGGAT TAGCAGAGCG AGGTATGTAG
3961 GCGGTGCTAC AGAGTTCTTG AAGTGGTGGC CTAACTACGG CTACACTAGA AGGACAGTAT
4021 TTGGTATCTG CGCTCTGCTG AAGCCAGTTA CCTTCGGAAA AAGAGTTGGT AGCTCTTGAT
4081 CCGGCAAACA AACCACCGCT GGTAGCGGTG GTTTTTTTGT TTGCAAGCAG CAGATTACGC
4141 GCAGAAAAAA AGGATCTCAA GAAGATCCTT TGATCTTTTC TACGGGGTCT GACGCTCAGT
4201 GGAACGAAAA CTCACGTTAA GGGATTTTGG TCATGAGATT ATCAAAAAGG ATCTTCACCT
4261 AGATCCTTTT AAATTAAAAA TGAAGTTTTA AATCAATCTA AAGTATATAT GAGTAAACTT
4321 GGTCTGACAG TTACCAATGC TTAATCAGTG AGGCACCTAT CTCAGCGATC TGTCTATTTC
4381 GTTCATCCAT AGTTGCCTGA CTCCCCGTCG TGTAGATAAC TACGATACGG GAGGGCTTAC
4441 CATCTGGCCC CAGTGCTGCA ATGATACCGC GAGACCCACG CTCACCGGCT CCAGATTTAT
4501 CAGCAATAAA CCAGCCAGCC GGAAGGGCCG AGCGCAGAAG TGGTCCTGCA ACTTTATCCG
4561 CCTCCATCCA GTCTATTAAT TGTTGCCGGG AAGCTAGAGT AAGTAGTTCG CCAGTTAATA
4621 GTTTGCGCAA CGTTGTTGCC ATTGCTACAG GCATCGTGGT GTCACGCTCG TCGTTTGGTA
4681 TGGCTTCATT CAGCTCCGGT TCCCAACGAT CAAGGCGAGT TACATGATCC CCCATGTTGT
4741 GCAAAAAAGC GGTTAGCTCC TTCGGTCCTC CGATCGTTGT CAGAAGTAAG TTGGCCGCAG
4801 TGTTATCACT CATGGTTATG GCAGCACTGC ATAATTCTCT TACTGTCATG CCATCCGTAA
4861 GATGCTTTTC TGTGACTGGT GAGTACTCAA CCAAGTCATT CTGAGAATAG TGTATGCGGC
4921 GACCGAGTTG CTCTTGCCCG GCGTCAATAC GGGATAATAC CGCGCCACAT AGCAGAACTT
4981 TAAAAGTGCT CATCATTGGA AAACGTTCTT CGGGGCGAAA ACTCTCAAGG ATCTTACCGC
5041 TGTTGAGATC CAGTTCGATG TAACCCACTC GTGCACCCAA CTGATCTTCA GCATCTTTTA
5101 CTTTCACCAG CGTTTCTGGG TGAGCAAAAA CAGGAAGGCA AAATGCCGCA AAAAAGGGAA
5161 TAAGGGCGAC ACGGAAATGT TGAATACTCA TACTCTTCCT TTTTCAATAT TATTGAAGCA
5221 TTTATCAGGG TTATTGTCTC ATGAGCGGAT ACATATTTGA ATGTATTTAG AAAAATAAAC
5281 AAATAGGGGT TCCGCGCACA TTTCCCCGAA AAGTGCCACC TGACGTCTAA GAAACCATTA
5341 TTATCATGAC ATTAACCTAT AAAAATAGGC GTATCACGAG GCCCTATGCGG TGTGAAATAC
5401 CGCACAGATG CGTAAGGAGA AAATACCGCA TCAGGCGCCA TTCGCCATTC AGGCTGCGCA
5461 ACTGTTGGGA AGGGCGATCG GTGCGGGCCT CTTCGCTATT ACGCCAGCTG GCGAAAGGGG
5521 GATGTGCTGC AAGGCGATTA AGTTGGGTAA CGCCAGGGTT TTCCCAGTCA CGACGTTGTA
5581 AAACGACGGC CAGTGCCAAG CTTGCATGCC TGCAGGTCGA
```

Plasmids pICLhac and pICLhaw were derived from plasmid pICL by digestion of the latter plasmid with the restriction enzyme Asp718. The linearized plasmid was treated with Calf-Intestine Alkaline Phosphatase to remove the 51 phosphate groups. The partially complementary synthetic single-stranded oligonucleotide Hp/asp1 (SEQ ID NO:17) and Hp/asp2 (SEQ ID NO:18) were annealed and phosphorylated on their 5' ends using T4-polynucleotide kinase.

Figure 16:
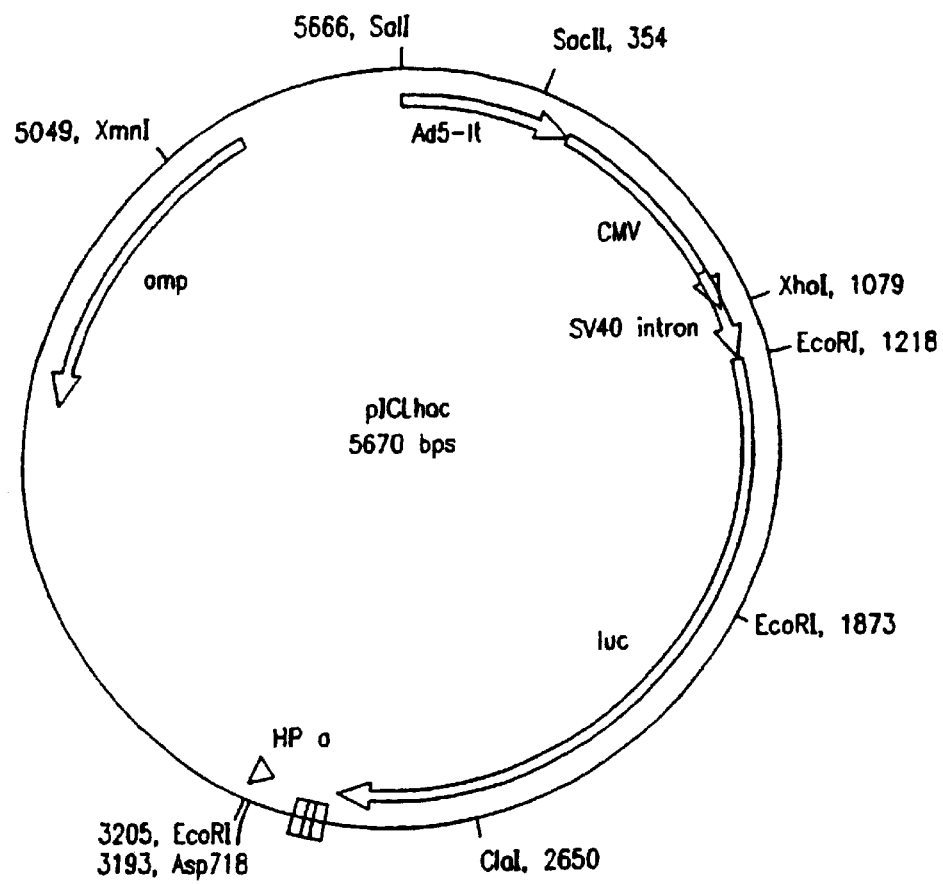
FIG. 16 illustrates a diagram of pICLhac according to the present invention.
Figure 17:
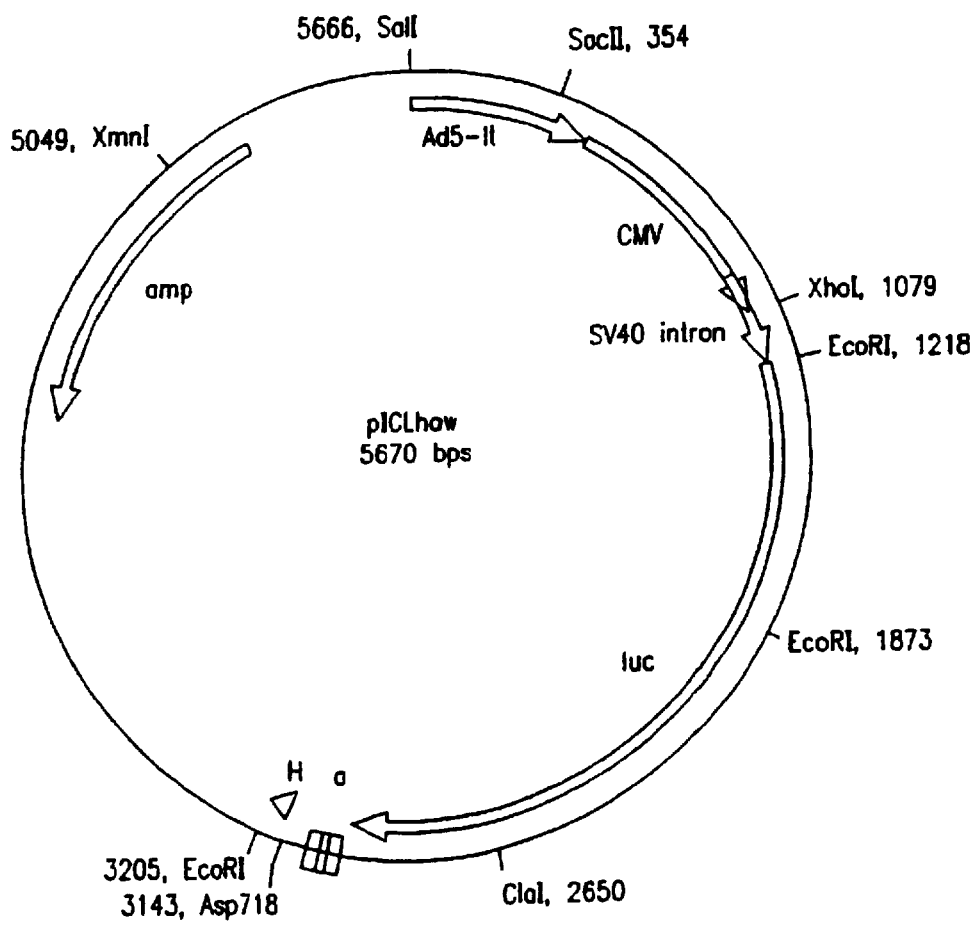
FIG. 17 illustrates a diagram of pICLhaw according to the present invention.
Figure 18:
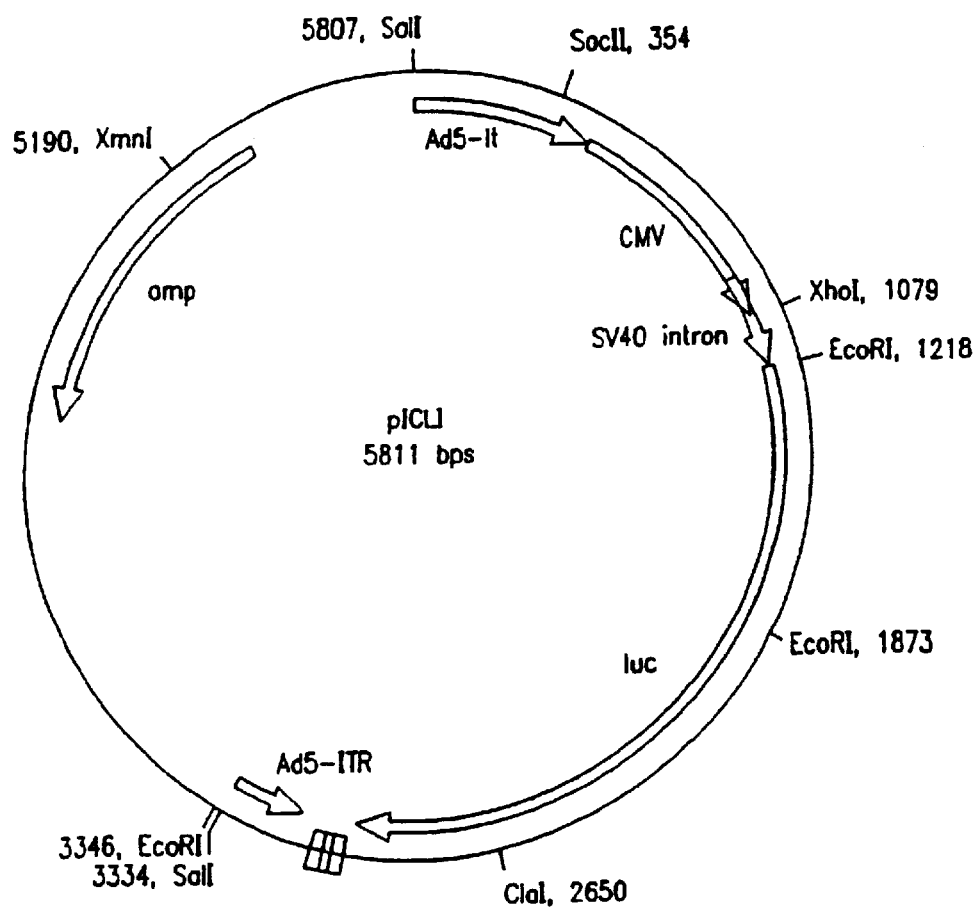
FIG. 18 illustrates a schematic representation of pICLI according to the present invention.

The phosphorylated double-stranded oligomers were mixed with the dephosphorylated pICL fragment and ligated. Clones containing a single copy of the synthetic oligonucleotide inserted into the plasmid were isolated and characterized using restriction enzyme digests. Insertion of the oligonucleotide into the Asp718 site will at one junction recreate an Asp718 recognition site, whereas at the other junction the recognition site will be disrupted. The orientation and the integrity of the inserted oligonucleotide was verified in selected clones by sequence analyses. A clone containing the oligonucleotide in the correct orientation (the Asp718 site close to the 3205 EcoRI site) was denoted pICLhac. A clone with the oligonucleotide in the reverse orientation (the Asp718 site close to the SV40 derived poly signal) was designated pICLhaw. Plasmids pICLhac and pICLhaw are represented in FIGS. 16 and 17.

Plasmid pICLI was created from plasmid pICL by insertion of the SalI-SgrAI fragment from pICL, containing the Ad5-ITR into the Asp718 site of pICL. The 194 bp SalI-SgrAI fragment was isolated from pICL, and the cohesive ends were converted to blunt ends using E. coli DNA polymerase I (Klenow fragment) and dNTP's. The Asp718 cohesive ends were converted to blunt ends by treatment with mungbean nuclease. By ligation, clones were generated that contain the ITR in the Asp718 site of plasmid pICL. A clone that contained the ITR fragment in the correct orientation was designated pICLI (see FIG. 18).

Recombinant adenovirus was constructed according to the method described in European Patent application 95202213. Two components are required to generate a recombinant adenovirus. First, an adaptor-plasmid containing the left terminus of the adenovirus genome containing the ITR and the packaging signal, an expression cassette with the gene of interest, and a portion of the adenovirus genome which can be used for homologous recombination. Second, adenovirus DNA is needed for recombination with the aforementioned adaptor plasmid. In the case of Ad-CMV-hcTK, the plasmid PCMV.TK was used as a basis. This plasmid contains nt. 1–455 of the adenovirus type 5 genome, nt. 456–1204 derived from pCMVβ (Clontech, the PstI-StuI fragment that contains the CMV enhancer promoter and the 16S/19S intron from Simian Virus 40), the Herpes Simplex Virus thymidine kinase gene (described in Patent application 95202213), the SV40-derived polyadenylation signal (nt. 2533–2668 of the SV40 sequence), followed by the BglII-ScaI fragment of Ad5 (nt. 3328–6092 of the Ad5 sequence). These fragments are present in a pMLP10-derived backbone (see the Levrero article). To generate plasmid pAD-CMVhc-TK, plasmid pCMV.TK was digested with ClaI (the unique ClaI-site is located just upstream of the TK open reading frame) and dephosphorylated with Calf-Intestine Alkaline Phosphate. To generate a hairpin-structure, the synthetic oligonucleotides HP/cla1 (SEQ ID NO:19) and HP/cla2 (SEQ ID NO:20) were annealed and phosphorylated on their 5-OH groups with T4-polynucleotide kinase and ATP. The double-stranded oligonucleotide was ligated with the linearized vector fragment and used to transform E. coli strain "Sure". Insertion of the oligonucleotide into the ClaI site will disrupt the ClaI recognition sites. In the oligonucleotide contains a new ClaI site near one of its termini. In selected clones, the orientation and the integrity of the inserted oligonucleotide was verified by sequence analyses. A clone containing the oligonucleotide in the correct orientation (the ClaI site at the ITR side) was denoted pAD-CMV-hcTK. This plasmid was co-transfected with ClaI digested wild-type Adenovirus-type 5 DNA into 911 cells. A recombinant adenovirus in which the CMV-hcTK expression cassette replaces the E1 sequences was isolated and propagated using standard procedures.

To study whether the hairpin can be used as a primer for reverse strand synthesis on the displaced strand after replication had started at the ITR, the plasmid pICLhac is introduced into 911 cells (human embryonic retinoblasts transformed with the adenovirus E1 region). The plasmid pICLhaw serves as a control, which contains the oligonucleotide pair HP/asp 1 (SEQ ID NO:17) and 2 (SEQ ID NO:18) in the reverse orientation, but is otherwise completely identical to plasmid pICLhac. Also included in these studies are plasmids pICLI and pICL. In the plasmid pICLI, the hairpin is replaced by an adenovirus ITR. Plasmid pICL contains neither a hairpin, nor an ITR sequence. These plasmids serve as controls to determine the efficiency of replication by virtue of the terminal-hairpin structure. To provide the viral products other than the E1 proteins (these are produced by the 911 cells) required for DNA replication, the cultures are infected with the virus IG.Ad.MLPI.TK after transfection. Several parameters are being studied to demonstrate proper replication of the transfected DNA molecules. First, DNA extracted from the cell cultures transfected with the aforementioned plasmids and infected with IG.Ad.MLPI.TK virus, is being analyzed by Southern blotting for the presence of the expected replication intermediates, as well as for the presence of the duplicated genomes. Furthermore, from the transfected and IG.Ad.MLPI.TK-infected cell populations, virus is isolated, which is able to transfer and express a luciferase marker gene into luciferase negative cells.

Plasmid DNA of plasmids pICLhac, pICLhaw, pICLI and pICL have been digested with restriction endonuclease SalI and treated with mungbean nuclease to remove the 4 nucleotide single-stranded extension of the resulting DNA fragment. In this manner, a natural adenovirus 5'ITR terminus on the DNA fragment is created. Subsequently, both the pICLhac and pICLhaw plasmids were digested with restriction endonuclease Asp718 to generate the terminus capable of forming a hairpin structure. The digested plasmids are introduced into 911 cells, using the standard calcium phosphate co-precipitation technique with four dishes for each plasmid. During the transfection for each plasmid, two of the cultures are infected with the IG.Ad.MLPI.TK virus using 5 infectious IG.Ad.MLPI.TK particles per cell. At twenty hours post-transfection and forty hours post-transfection, one Ad.tk-virus-infected and one uninfected culture were used to isolate small molecular-weight DNA using the procedure devised by Hirt, as described in Einerhand, et al., "Regulated High-Level Human Beta-Globin Gene Expression in Erythroid Cells Following Recombinant Adeno-Associated Virus-Mediated Gene Transfer", Gene Therapy 2, pp. 336–343 (1995). Aliquots of isolated DNA were used for Southern analysis. After digestion of the samples with restriction endonuclease EcoRI using the luciferase gene as a probe, a hybridizing fragment of approximately 2.6 kb was detected only in the samples from the adenovirus-infected cells transfected with plasmid pICLhac. The size of this fragment was consistent with the anticipated duplication of the luciferase marker gene. This supports the conclusion that the inserted hairpin is capable to serve as a primer for reverse strand synthesis. The hybridizing fragment is absent if the IG.Ad.MLPI.TK virus is omitted, or if the hairpin oligonucleotide has been inserted in the reverse orientation.

The restriction endonuclease DpnI recognizes the tetranucleotide sequence 5'-GATC-3', but cleaves only methylated DNA (that is, only (plasmid) DNA propagated in, and derived, from E. coli, not DNA that has been replicated in mammalian cells). The restriction endonuclease MboI recognizes the same sequences, but cleaves only unmethylated DNA (viz. DNA propagated in mammalian cells). DNA samples isolated from the transfected cells are incubated with MboI and DpnI and analyzed with Southern blots. These results demonstrate that only in the cells transfected with the pICLhac and the pICLI plasmids, large DpnI-resistant fragments are present that are absent in the MboI treated samples. These data demonstrate that only after transfection of plasmids pICLI and pICLhac, replication and duplication of the fragments occur.

These data demonstrate that in adenovirus-infected cells linear DNA fragments that have on one terminus an adenovirus-derived inverted terminal repeat (ITR) and at the other terminus a nucleotide sequence that can anneal to sequences on the same strand, when present in single-stranded form, thereby generate a hairpin structure, and will be converted to structures that have inverted terminal repeat sequences on both ends. The resulting DNA molecules will replicate by the same mechanism as the wild type adenovirus genomes.

EXPERIMENT 2

Experimentation was conducted to demonstrate that the DNA molecules which contain a luciferase marker gene, a single copy of the ITR, the encapsidation signal and a synthetic DNA sequence, that is capable of forming a hairpin structure, are sufficient to generate DNA molecules that can be encapsidated into virions.

To demonstrate that the above DNA molecules containing two copies of the CMV-luc marker gene can be encapsidated into virions, virus was harvested from the remaining two cultures from Experiment 1 via three cycles of freeze-thaw crushing and was used to infect murine fibroblasts. Forty-eight hours after infection, the infected cells were assayed for luciferase activity. To exclude the possibility that the luciferase activity was been induced by transfer of free DNA, rather than via virus particles, virus stocks were treated with DNaseI to remove DNA contaminants. Furthermore, as an additional control, aliquots of the virus stocks were incubated for 60 minutes at 56° C. The heat treatment will not affect the contaminating DNA, but will activate the viruses. Significant luciferase activity was only found in the cells after infection with the virus stocks derived from IG.Ad.MLPI.TK-infected cells transfected with the pICLhc and pICLI plasmids. Neither in the non-infected cells, nor in the infected cells transfected with the pICLhw and pICL, significant luciferase activity were demonstrated. Heat inactivation, but not DNaseI treatment, completely eliminates luciferase expression, demonstrating that adenovirus particles, and not free (contaminating) DNA fragments, were responsible for transfer of the luciferase reporter gene.

These results demonstrate that these small viral genomes can be encapsidated into adenovirus particles and suggest that the ITR and the encapsidation signal are sufficient for encapsidation of linear DNA fragments into adenovirus particles. These adenovirus particles can be used for efficient gene transfer. When introduced into cells that contain and express at least part of the adenovirus genes (viz. E1, E2, E4, and L, and VA), recombinant DNA molecules that consist of at least one ITR, at least part of the encapsidation signal as well as synthetic DNA sequence, that is capable of forming a hairpin structure, have the intrinsic capacity to autonomously generate recombinant genomes which can be encapsidated into virions. Such genomes and vector system can be used for gene transfer.

EXPERIMENT 3

Experimentation was conducted to demonstrate that DNA molecules which contain nucleotides 3510–35953 (viz. 9.7–100 map units) of the adenovirus type 5 genome (thus lack the E1 protein-coding regions, the right-hand ITR and the encapsidation sequences) and a terminal DNA sequence that is complementary to a portion of the same strand of the DNA molecule when present in single-stranded form other than the ITR, and as a result is capable of forming a hairpin structure, can replicate in 911 cells.

In order to develop a replicating DNA molecule that can provide the adenovirus products required to allow the above mentioned ICLhac vector genome and alike minimal adenovectors to be encapsidated into adenovirus particles by helper cells, the Ad-CMV-hcTK adenoviral vector was developed. Between the CMV enhancer/promoter region and the thymidine kinase gene, the annealed oligonucleotide pair HP/cla 1 (SEQ ID NO:19) and 2 (SEQ ID NO:20) is inserted. The vector Ad/CMV-hcTK can be propagated and produced in 911 cells using standard procedures. This vector was grown and propagated exclusively as a source of DNA used for transfection. DNA of the adenovirus Ad-CMV-hcTK was isolated from virus particles that had been purified using CsCl density-gradient centrifugation by standard techniques. The virus DNA was digested with restriction endonuclease ClaI. The digested DNA was size-fractionated on an 0.7% agarose gel and the large fragment was isolated and used for further experiments. Cultures of the 911 cells were transfected large ClaI-fragment of the Ad-CMV-hcTK DNA using the standard calcium phosphate co-precipitation technique. Much like in the previous experiments with plasmid pICLhac, the AD-CMV-hc will replicate starting at the right-hand ITR. Once the 1-strand is displaced, a hairpin can be formed at the left-hand terminus of the fragment. This facilitates the DNA polymerase to elongate the chain towards the right-hand-side. The process will proceed until the displaced strand is completely converted to its double-stranded form. Finally, the right-hand ITR will be recreated, and in this location the normal adenovirus replication-initiation and elongation will occur. Note that the polymerase will read through the hairpin, thereby duplicating the molecule. The input DNA molecule of 33250 bp, that had on one side an adenovirus ITR sequence and at the other side a DNA sequence that had the capacity to form a hairpin structure, has now been duplicated, in a way that both ends contain an ITR sequence. The resulting DNA molecule will consist of a palindromic structure of approximately 66500 bp.

This structure was detected in low-molecular weight DNA extracted from the transfected cells using Southern analysis. The palindromic nature of the DNA fragment was demonstrated by digestion of the low-molecular weight DNA with suitable restriction endonucleases and Southern blotting with the HSV-TK gene as the probe. This molecule can replicate itself in the transfected cells by virtue of the adenovirus gene products that are present in the cells. In part, the adenovirus genes are expressed from templates that are integrated in the genome of the target cells (viz. the E1 gene products). The other genes reside in the replicating DNA fragment itself. Note, however, that this linear DNA fragment cannot be encapsidated into virions. Not only does it lack all the DNA sequences required for encapsidation, but also its size is much too large to be encapsidated.

EXPERIMENT 4

Experimentation was conducted to demonstrate that DNA molecules which contain nucleotides 3503–35953 (viz. 9.7–100 map units) of the adenovirus type 5 genome (thus lack the E1 protein-coding regions, the right-hand ITR and the encapsidation sequences) and a terminal DNA sequence that is complementary to a portion of the same strand of the DNA molecule other than the ITR, and as a result is capable of forming a hairpin structure, can replicate in 911 cells and can provide the helper functions required to encapsidate the pICLI and pICLhac-derived DNA fragments. This experiment demonstrated that the DNA molecule described in Experiment 3 could be used to encapsidate the minimal adenovectors described in Experiment 1 and Experiment 2.

The large fragment isolated after endonuclease ClaI-digestion of Ad-CMV-hcTK DNA were introduced into 911 cells (see, Experiment 3), together with endonuclease SalI, mungbean nuclease, endonuclease Asp718-treated plasmid pICLhac, or as a control, similarly treated plasmid pICLhaw. After 48 hours, the virus was isolated by freeze-thaw crushing of the transfected cell population. The virus-preparation was treated with DNaseI to remove contaminating free DNA. The virus was used subsequently to infect Rat2 fibroblasts. Forty-eight hours post-infection, the cells are assayed for luciferase activity. Only in the cells infected with virus isolated from the cells transfected with the pICLhac plasmid, and not with the pICLhaw plasmid, demonstrated significant luciferase activity. Heat inactivation of the virus prior to infection completely abolishes the luciferase activity, indicating that the luciferase gene is transferred by a viral particle. Infection of the 911 cells with the virus stock did not result in any cytopathological effects, demonstrating that the pICLhac was produced without any infectious helper virus that can be propagated on 911 cells. These results demonstrated that the proposed method can be used to produce stocks of minimal adenoviral vectors that are completely devoid of infectious helper viruses which are able to replicate autonomously on adenovirus-transformed human cells or on non-adenovirus transformed human cells.

Beside the system described in this application, another approach for the generation of minimal adenovirus vectors has been disclosed in WO 94/12649. The method described in WO 94/12649 exploits the function of the protein IX for the packaging of minimal adenovirus vectors (Pseudo Adenoviral Vectors (PAV) in the terminology of WO 94/12649). PAVs are produced by cloning an expression plasmid with the gene of interest between the left-hand (including the sequences required for encapsidation) and the right-hand adenoviral ITRs. The PAV is propagated in the presence of a helper virus. Encapsidation of the PAV is preferred, compared to the helper virus, because the helper virus is partially defective for packaging, either by virtue of mutations in the packaging signal or by virtue of its size (virus genomes greater than 37.5 kb package inefficiently). In addition, the authors propose that in the absence of the protein IX gene, the PAV will be preferentially packaged. However, neither of these mechanisms appear to be sufficiently restrictive to allow packaging of only PAVs/minimal vectors. The mutations proposed in the packaging signal diminish packaging but do not provide an absolute block, as the same packaging-activity is required to propagate the helper virus. Also, neither an increase in the size of the helper virus nor the mutation of the protein IX gene will ensure that PAV is packaged exclusively. Thus, the method described in WO 94/12649 is unlikely to be useful for the production of helper-free stocks of minimal adenovirus vectors/PAVs.

What is claimed is:

1. A method for producing a recombinant adenovirus comprising a gene of interest, said method not producing an adenovirus having a functional E1 region, said method comprising:

providing a complementing cell, said complementing cell harboring a first nucleic acid comprising adenoviral nucleic acid encoding functional E1A protein and E1B protein but not pIX protein;

transferring recombinant nucleic acid into said complementing cell, said recombinant nucleic acid comprising:

a second nucleic acid containing adenoviral nucleic acid including at least one encapsidation signal, and functional Inverted Terminal Repeats at or near both termini, said second nucleic acid further comprising a gene of interest and all sequences required for replication of said second nucleic acid which are not provided by said complementing cell; said recombinant nucleic acid lacking overlapping sequences with the first nucleic acid, which overlap could otherwise lead to homologous recombination resulting in the formation of adenovirus having a functional E1 region;

culturing said complementing cell; and harvesting the recombinant adenovirus produced from said complementing cell.

2. The method according to claim 1 wherein said recombinant nucleic acid is one nucleic acid molecule in linear form.

3. The method according to claim 1 wherein said complementing cell is derived from a primary cell.

4. The method according to claim 1 wherein said recombinant nucleic acid is DNA.

5. A method of producing, in a producer cell, recombinant adenovirus comprising a gene of interest, said method comprising:

culturing a producer cell comprising a first nucleic acid sequence encoding at least adenoviral E1A region gene product but not encoding pIX protein and a second nucleic acid containing adenoviral nucleic acid including at least one encapsidation signal and functional Inverted Terminal Repeats at or near both termini, said second nucleic acid further comprising a gene of interest and all sequences required for replication of said second nucleic acid which are not provided by said producer cell, said second nucleic acid having no overlapping sequences with respect to said first nucleic acid sequence which overlap could otherwise lead to homologous recombination resulting in the formation of adenovirus having a functional E1 region; and harvesting recombinant adenovirus produced from said cell.

6. The method according to claim 5 wherein said producer cell further comprises a sequence encoding adenoviral E2A region gene product, wherein said sequence encoding adenoviral E2A region gene product is selected from the group consisting of a DNA sequence encoding the wild-type E2A region operably linked to an inducible promoter and a DNA sequence encoding a temperature sensitive 125 mutation.

7. The method according to claim 1, wherein said recombinant nucleic acid comprises at least two nucleic acid molecules that upon homologous recombination are capable of forming said second nucleic acid.

8. The method according to claim 1, wherein said first nucleic acid is integrated into the genome of said complementing cell.

9. The method according to claim 5, wherein said first nucleic acid sequence is integrated into the genome of said producer cell.

10. The method according to claim 5, wherein said first nucleic acid sequence further encodes an adenoviral E1B region gene product.

11. The method according to claim 6, wherein said sequence encoding adenoviral E2A region gene product is integrated into the genome of the producer cell.

12. The method according to claim 6, wherein the recombinant adenovirus produced has a deletion in the E2A region.

* * * * *